(12) United States Patent
Balzarini et al.

(10) Patent No.: US 9,278,958 B2
(45) Date of Patent: Mar. 8, 2016

(54) ANTI-CANCER COMPOUNDS

(71) Applicants: KATHOLIEKE UNIVERSITEIT LEUVEN, Leuven (BE); UNIVERSITA DEGLI STUDI DI FERRARA, Ferrara (IT)

(72) Inventors: Jan Balzarini, Heverlee (BE); Wim Dehaen, Heverlee (BE); Joice Thomas, Leuven (BE); Sandra Liekens, Begijnendijk (BE); Romeo Romagnoli, Ferrara (IT); Pier Giovanni Baraldi, Ferrara (IT)

(73) Assignees: Katholieke Universiteit Leuven K.U. Leuven R&D, Leuven (BE); Universita Degli Studi Di Ferrara, Ferrara (IT)

( * ) Notice: Subject to any disclaimer, the term of this patent is extended or adjusted under 35 U.S.C. 154(b) by 0 days.

(21) Appl. No.: 14/403,620

(22) PCT Filed: Jun. 21, 2013

(86) PCT No.: PCT/EP2013/063082
§ 371 (c)(1),
(2) Date: Nov. 25, 2014

(87) PCT Pub. No.: WO2013/190137
PCT Pub. Date: Dec. 27, 2013

(65) Prior Publication Data
US 2015/0126559 A1    May 7, 2015

(30) Foreign Application Priority Data

Jun. 22, 2012  (GB) .................................. 1211086.2
Dec. 10, 2012  (GB) .................................. 1222113.1

(51) Int. Cl.
| | |
|---|---|
| *C07D 409/06* | (2006.01) |
| *C07D 333/36* | (2006.01) |
| *C07D 333/38* | (2006.01) |
| *C07D 401/12* | (2006.01) |
| *C07D 405/12* | (2006.01) |
| *C07D 409/12* | (2006.01) |
| *A61K 31/381* | (2006.01) |
| *A61K 31/4436* | (2006.01) |
| *A61K 45/06* | (2006.01) |
| *C07D 307/54* | (2006.01) |
| *C07D 307/66* | (2006.01) |
| *C07D 409/04* | (2006.01) |

(52) U.S. Cl.
CPC ............ *C07D 409/06* (2013.01); *A61K 31/381* (2013.01); *A61K 31/4436* (2013.01); *A61K 45/06* (2013.01); *C07D 307/54* (2013.01); *C07D 307/66* (2013.01); *C07D 333/36* (2013.01); *C07D 333/38* (2013.01); *C07D 401/12* (2013.01); *C07D 405/12* (2013.01); *C07D 409/04* (2013.01); *C07D 409/12* (2013.01)

(58) Field of Classification Search
CPC ............................ C07D 333/36; C07D 409/06
USPC ............................................ 514/336; 549/71
See application file for complete search history.

(56) References Cited

U.S. PATENT DOCUMENTS

| | | | |
|---|---|---|---|
| 2005/0085531 | A1 | 4/2005 | Hodge et al. |
| 2005/0165087 | A1 | 7/2005 | Callahan et al. |
| 2010/0273815 | A1 | 10/2010 | Borate et al. |

FOREIGN PATENT DOCUMENTS

| | | |
|---|---|---|
| WO | 03104218 A1 | 12/2003 |
| WO | 2005033102 A2 | 4/2005 |
| WO | 2009109983 A1 | 9/2009 |

OTHER PUBLICATIONS

International Search Report dated Oct. 1, 2013 in connection with PCT International Patent Application No. PCT/EP2013/063082, 7 pages.
Romagnoli R et al., entitled "Synthesis of novel antimitotic agents based on 2-amino-3-aroyl-5-(hetero)arylethynyl thiophene derivatives," Bioorganic & Medicinal Chemistry Letters, vol. 21, No. 9, May 1, 2011, pp. 2746-2751.
Rosowsky A et al., entitled "2,4-Diaminothieno[2,3-d]pyrimidines as Antifolates and Antimalarials. 3. Synthesis of 5,6-Disubstituted Derivatives and Related Tetracyclic Analogs," J. Med. Chem., Jan. 1, 1973, vol. 16, No. 3, pp. 191-194.
Rosowsky A et al., entitled "2,4-Diaminothieno[2,3-d]pyrimidine Analogues of Trimetrexate and Piritrexim as Potential Inhibitors of Pneumocystis carinii and Toxoplasma gondii Dihydrofolate Reductase," Journal of Medicinal Chemistry, vol. 36, Jan. 1, 1993, pp. 3103-3112.
Huang, X-G et al., entitled "A facile and practical one-pot synthesis of multisubstituted 2-aminothiophenes via imidazole-catalyzed Gewald reaction," Tetrahedron, vol. 67, No. 34, Jun. 21, 2011, pp. 6202-6205.

(Continued)

*Primary Examiner* — Taofiq A Solola
(74) *Attorney, Agent, or Firm* — Amster, Rothstein & Ebenstein LLP

(57) ABSTRACT

The present invention relates to compounds having cytostatic activity against tumor cells. The compounds of the invention are of formula (I), or derivatives hereof, wherein $R^0$, $R^1$, $R^2$, A, and X have defined meanings as described in claim 1.

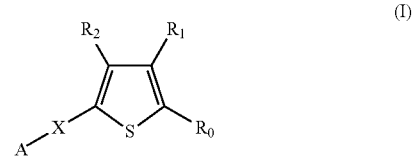

(I)

24 Claims, 4 Drawing Sheets

(56) References Cited

OTHER PUBLICATIONS

Donker I O et al., entitled "Synthesis and DHFR inhibitory activity of a series of 6-substituted-2,4-diaminothieno[2,3-d]pyrimidines," European Journal of Medicinal Chemistry, vol. 38, No. 6, Jun. 1, 2003, pp. 605-611.

Deng Y et al., entitled "Synthesis and Biological Activity of a Novel Series of 6-Substituted Thieno[2,3-d]pyrimidine Antifolate Inhibitors of Purine Biosynthesis with Selectivity for High Affinity Folate Receptors over the Reduced Folate Carrier and Proton-Coupled Folate Transporter for Cellular Entry," Journal of Medicinal Chemistry, vol. 52, No. 9, May 14, 2009, pp. 2940-2951.

Wang K et al., entitled "Cyanoacetamide MCR (III): Three-Coponent Geward Reactions Revisited," Journal of Combinatorial Chemistry, vol. 12, No. 1, Jan. 11, 2010, pp. 111-118.

PCT Notification Concerning Transmittal of International Preliminary Report on Patentability and Written Opinion of the International Searching Authority dated Dec. 23, 2014 in connection with PCT International Patent Application No. PCT/EP2013/063082, 13 pages.

ANTI-CANCER COMPOUNDS

CROSS-REFERENCE TO RELATED APPLICATIONS

This application is a U.S. national stage entry under 35 U.S.C. §371 of PCT International Patent Application No. PCT/EP2013/063082, filed Jun. 21, 2013, which claims priority to Great Britain Patent Application No. 1222113.1, filed Dec. 10, 2012 and Great Britain Patent Application No. 1211086.2, filed Jun. 22, 2012, the contents of all of which are incorporated herein by reference in their entirety.

FIELD OF THE INVENTION

The invention relates to compounds and compositions containing said compounds having cytostatic (antiproliferative) activity against tumor cells, more specifically against T-cell lymphoma, hepatoma and prostate cancer cells. The invention also provides processes for the preparation of the disclosed compounds and compositions containing said compounds. The invention further relates to the use of said compounds as biologically active ingredients, more specifically as a medicine for the treatment of cancer.

BACKGROUND OF THE INVENTION

2-Aminothiophene-3-carboxylic acid esters and their 3-carbonitrile analogues are commonly used for the synthesis of 2-unsubstituted thieno[2,3-d]pyrimidines. These compounds were endowed with biological activity). A variety of 2-aminothiophene-3-carboxylates and carboxamides, in particular 2-amino-4,5,6,7-tetrahydrobenzo[b]thiophene and 2-amino-5,6,7,8-tetrahydrocyclohepta[b]thiophenes with 3-carboxylate and 3-carboxamide substituents were found to behave as adenosine A1 receptor allosteric enhancers and 2-amino-4,5,6,7-tetrahydro N-phenylbenzo[b]thiophene-3-carboxamides were endowed with anti-arrhythmic, serotonin antagonist and anti-anxiety activities. Several 2-aminothiophene analogues were also shown to exhibit anti-inflammatory potential. All above-mentioned compound classes were synthesized starting from 2-aminothiophene-3-carboxylic acids which resulted in the formation of thiophenes containing a fixed ring system. Interestingly, the fluorophenyl derivative of the thiophene 2-ureido-3-carboxylic acid amide TPCA-1 has recently been identified as a small molecule IKB kinase β (IKKβ) inhibitor.

Recently, we have synthesized a series of 2-amino-3-aroyl-4-substituted thiophene derivatives as anti-proliferative agents. They seem to inhibit tubulin polymerization, resulting in an accumulation of a proportion of the drug-exposed cells in the G2/M and sub-G1 phases of the cell cycle (Romagnoli et al., 2010) (1). However the compounds discovered in Romagnoli et al., 2010 showed no selectivity. Thus there is still a big need for very active and selective anti-proliferative compounds in this field and such selective and active compounds are useful for treating hyperproliferative disorders.

SUMMARY OF THE INVENTION

The present invention is based on the unexpected finding that certain combinations of substituents at different positions of 2-amino,3-carboxylic ester thiophenes and their derivatives, said combinations not being suggested by the prior art, are able to meet one or more of the medical needs, and to show unexpected biological properties, in particular have significant and selective anticancer activity.

The present invention concerns a compound of formula I, Ia, or Ib:

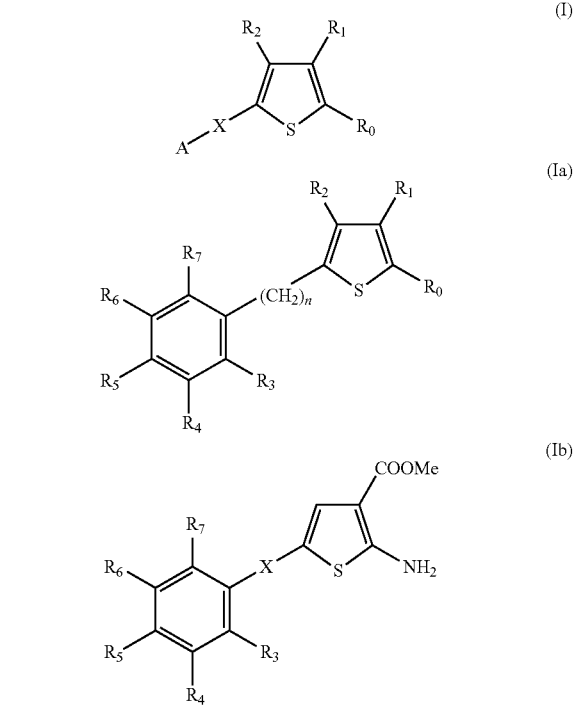

wherein,
A is selected from the group consisting of $C_{1-7}$ alkyl; $C_{2-7}$ alkenyl; $C_{2-7}$ alkynyl; halo $C_{1-7}$ alkyl; $C_{3-10}$ cycloalkyl; $C_{1-7}$ alkoxy; $C_{3-10}$ cycloalkoxy; aryloxy; arylalkyloxy; oxyheterocyclic; thio $C_{1-7}$ alkyl; thio $C_{3-10}$ cycloalkyl; arylthio; arylalkylthio; heterocyclic-substituted alkyl; heterocyclic-substituted alkyloxy; heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, and wherein said alkyl is optionally substituted with one or more substituents selected from the group consisting of halogen, nitro, hydroxyl, sulfhydryl, amino, azido;

$R^0$ is independently selected from the group consisting of amino; (mono- or di) $C_{1-7}$ alkylamino; (mono- or di) arylamino; azido; 1H-Isoindole-1,3(2H)-dione,2-methyl-;

$R^1$ is independently selected from the group consisting of carboxy$C_{1-7}$ alkyl; cyano; —COOH; CONR$^a$R$^b$; SO$_2$R; SO$_2$NHR; SO$_2$NR$^a$R$^b$, SO$_2$OR; PO(XR)$_2$; and $C_{3-10}$ cycloalkyl, wherein R, R$^a$ and R$^b$ are each independently selected from the group consisting of H and $C_{1-7}$alkyl and $C_{3-10}$ cycloalkyl;

$R^2$ is independently selected from the group consisting of hydrogen; carboxy$C_{1-7}$ alkyl, $C_{1-7}$alkyl; cyano; —CONHMe; —COOH; —CONH$_2$ X is independently selected from the group consisting of —(CH$_2$)$_n$, —(CH$_2$)$_m$-acetylene, -acetylene-(CH$_2$)$_m$—, —(CH$_2$)$_m$-ethylene, -ethylene-(CH$_2$)$_m$—, —S(CH$_2$)$_m$—, —(CH$_2$)$_m$S—, —O(CH$_2$)$_m$—, —(CH$_2$)$_m$O—, —NH(CH$_2$)$_m$—; —(CH$_2$)$_m$NH—, —(CH$_2$)$_m$S(CH$_2$)$_p$—, —(CH$_2$)$_m$O(CH$_2$)$_p$, wherein m is 0, 1, 2, 3, 4, 5, 6 or 7, and wherein p is 0, 1, 2, 3, 4, 5, 6 or 7, and wherein n is 2, 3, 4, 5, 6 or 7;

R$^3$, R$^4$, R$^5$, R$^6$ and R$^7$ are independently selected from the group consisting of hydrogen; C$_{1-7}$alkyl; C$_{1-7}$ alkoxy; halogen; amino; (mono- or di) C$_{1-7}$ alkylamino, (mono- or di) arylamino; azido; hydroxyl; C$_{3-10}$ cycloalkyl, and wherein said alkyl is optionally substituted with one or more substituents selected from the group consisting of halogen, nitro, hydroxyl, sulfhydryl, amino, azido;

and/or a pharmaceutical acceptable addition salt thereof and/or a stereoisomer thereof and/or a solvate thereof.

In some embodiments, said compound is not Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitrile; 2-Amino-5-benzylthiophene-3-carbonitrile; 2-Amino-5-isopropylthiophene-3-carbonitrile; 2-Amino-5-(tert-butyl) thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl) thiophene-3-carboxamide; 2-Amino-3-cyano-5-[2-(2',5'-dimethoxyphenyl)ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile.

The present invention also concerns a compound having formula I, Ia or Ib, for use as a medicine.

The present invention also concerns a compound having formula I, Ia or Ib, for use as a medicine for the prevention or treatment of a proliferative disorder, including cancer in an animal, preferably in a mammal. In an embodiment, said mammal is a human being.

The present invention also concerns the use of a compound having formula I, Ia or Ib for use as a medicine for the prevention or treatment of proliferative disorders, including cancer, in an animal, preferably a mammal, and more preferably a human. The present invention also concerns the use of a compound having formula I, Ia or Ib for the manufacture of a medicament for the prevention or treatment of a proliferative disorder such as cancer in an animal, preferably a mammal, and more preferably a human.

In more specific embodiments of the invention, said proliferative disorder is cancer. In a more particular embodiment of the invention, said cancer is a hematological malignancy, such as leukemia (e.g. Lymphoblastic T cell leukemia, Chronic myelogenous leukemia (CML), Chronic lymphocytic/lymphoid leukemia (CLL), Hairy-cell leukemia, acute lymphoblastic leukemia (ALL), acute myelogenous leukemia (AML), myelodysplastic syndrome, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, Acute megakaryocytic leukemia, promyelocytic leukemia and Erythroleukemia) and lymphoma, more specifically malignant lymphoma, Hodgkin's lymphoma, non-Hodgkin's lymphoma, lymphoblastic T cell lymphoma, Burkitt's lymphoma and follicular lymphoma, MALT1 lymphomas, Hodgkin lymphomas, B-cell non-Hodgkin lymphoma- and marginal zone lymphoma. In a more particular embodiment of the invention, said cancer is selected from the group of hematological malignancies comprising acute leukemia, chronic leukemia, lymphoma, multiple myeloma, myelodysplastic syndrome. In a more particular embodiment of the invention, said chronic leukemia is myeloid or lymphoid. In another more particular embodiment of the invention, said lymphoma is Hodgkin's or non-Hodgkin's lymphoma.

In another particular embodiment of the present invention, said cancer is a non-hematological cancer or solid tumor cancer such as cancer of the prostate, lung, breast, rectal, colon, lymph node, bladder, kidney, pancreatic, liver, ovarian, uterine, brain, skin, sarcoma, meningioma, glioblastoma, multiforme, skin, stomach, including all kinds of neuroblastoma, gastric carcinoma, renal cell carcinoma, neuroblastoma, gastric carcinoma, renal cell carcinoma, uterine cancer and muscle cancer. In another more particular embodiment of the present invention, said cancer is prostate cancer. In yet another more particular embodiment of the present invention, said cancer is liver cancer.

The present invention also concerns a pharmaceutical composition comprising a therapeutically effective amount of a compound having formula I, Ia or Ib, and one or more pharmaceutically acceptable excipients for use as a medicine for the prevention or treatment of a proliferative disorder such as cancer in an animal, mammal or human. Said composition may further comprise one or more biologically active drugs being selected from the group consisting of antineoplastic drugs and/or immunosuppressant and/or immunomodulator drugs.

The present invention also concerns a method of prevention or treatment of proliferative disorder, including cancer such as hematological malignancies, including acute leukemia, chronic leukemia (myeloid or lymphoid), lymphoma (Hodgkin's or non-Hodgkin's), multiple myeloma, myelodysplastic syndrome, or non-hematological cancers such as prostate carcinoma or liver carcinoma, in an animal, comprising the administration of a therapeutically effective amount of a compound having formula I, Ia or Ib, optionally in combination with one or more pharmaceutically acceptable excipients.

The present invention also concerns a process for preparation of the compounds of formula I, Ia or Ib comprising the steps of:

(a) a Gewald reaction of an enolizable compound (aldehyde or ketone), sulfur and an active methylene containing a cyano group;

(b) protection of the 5-amino group as phthalimide and further transformations at the 2-position of the thiophene starting from bromo or 2-bromomethyl derivatives; thus introducing the aromatic, heterocyclic or lipophilic side chain; and (c) deprotection of the phthalimide function by hydrazine or methylhydrazine to liberate the 5-aminothiophene.

Numbered statements of this invention are:
1. A compound having the general formula I, Ia, or Ib:

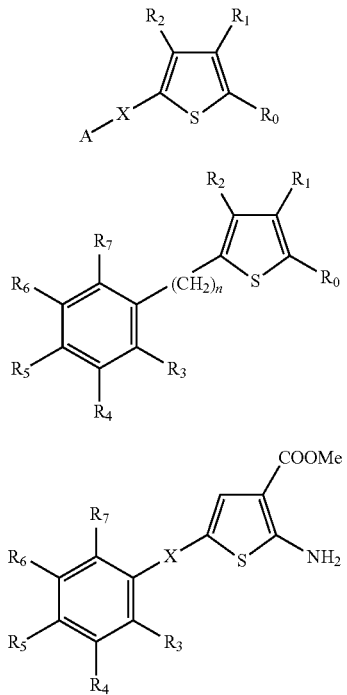

wherein
A is selected from the group consisting of $C_{1-7}$ alkyl; $C_{2-7}$ alkenyl; $C_{2-7}$ alkynyl; halo $C_{1-7}$ alkyl; $C_{3-10}$ cycloalkyl; $C_{1-7}$ alkoxy; $C_{3-10}$ cycloalkoxy; aryloxy; arylalkyloxy; oxyheterocyclic; thio $C_{1-7}$ alkyl; thio $C_{3-10}$ cycloalkyl; arylthio; arylalkylthio; heterocyclic-substituted alkyl; heterocyclic-substituted alkyloxy; heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, and wherein said alkyl is optionally substituted with one or more substituents selected from the group consisting of halogen, nitro, hydroxyl, sulfhydryl, amino, azido;
$R^0$ is independently selected from the group consisting of amino; (mono- or di) $C_{1-7}$ alkylamino; (mono- or di) arylamino; azido; 1H-Isoindole-1,3(2H)-dione,2-methyl-;
$R^1$ is independently selected from the group consisting of carboxy$C_{1-7}$ alkyl; cyano; —COOH; CONR$^a$R$^b$; SO2R; SO$_2$NHR; SO$_2$NR$^a$R$^b$, SO$_2$OR; PO(XR)$_2$; and $C_{3-10}$ cycloalkyl, wherein R, R$^a$ and R$^b$ are each independently selected from the group consisting of H and $C_{1-7}$alkyl and $C_{3-10}$ cycloalkyl;
$R^2$ is independently selected from the group consisting of hydrogen; carboxy$C_{1-7}$ alkyl, $C_{1-7}$alkyl; cyano; —CONHMe; —COOH; —CONH$_2$
X is independently selected from the group consisting of —(CH$_2$)$_n$—, —(CH$_2$)$_m$-acetylene, -acetylene-(CH$_2$)$_m$—, —(CH$_2$)$_m$-ethylene, -ethylene-(CH$_2$)$_m$—, —S(CH$_2$)$_m$—, —(CH$_2$)$_m$S—, —O(CH$_2$)$_m$—, —(CH$_2$)$_m$O—, —NH(CH$_2$)$_m$—; —(CH$_2$)$_m$NH—, —(CH$_2$)$_m$S(CH$_2$)$_p$—, —(CH$_2$)$_m$O(CH$_2$)$_p$, wherein m is 0, 1, 2, 3, 4, 5, 6 or 7, and wherein p is 0, 1, 2, 3, 4, 5, 6 or 7, and wherein n is 2, 3, 4, 5, 6 or 7;
$R^3$, $R^4$, $R^5$, $R^6$ and $R^7$ are independently selected from the group consisting of hydrogen; $C_{1-7}$alkyl; $C_{1-7}$ alkoxy; halogen; amino; (mono- or di) $C_{1-7}$ alkylamino, (mono- or di) arylamino; azido; hydroxyl; $C_{3-10}$ cycloalkyl, and wherein said alkyl is optionally substituted with one or more substituents selected from the group consisting of halogen, nitro, hydroxyl, sulfhydryl, amino, azido;
and/or a pharmaceutical acceptable addition salt thereof and/or a stereoisomer thereof and/or a solvate thereof;
with the proviso that said compound is not Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitrile; 2-Amino-5-benzylthiophene-3-carbonitrile; 2-Amino-5-isopropylthiophene-3-carbonitrile; 2-Amino-5-(tert-butyl)thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl)thiophene-3-carboxamide; 2-Amino-3-cyano-5-[2-(2', 5'-dimethoxyphenyl)ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile.
2. The compound according to statement 1, wherein A is $C_{1-7}$ alkyl or $C_{2-7}$ alkenyl.
3. The compound according to statement 1, wherein A is phenyl or thiophene.
4. The compound according to any of statements 1 to 3, wherein $R^1$ is carboxy$C_{1-7}$alkyl, preferably a carboxymethyl or carboxyethyl group.
5. The compound according to any of statements 1, 3 and 4, wherein A is an aryl group substituted with 1 or 2 substituents selected from the group consisting of a methoxy group and a methyl group.
6. The compound according to any of statements 1 to 5, wherein X is selected from the group consisting of a —(CH$_2$)$_2$, an ethylene and an acetylene group.
7. The compound according to any of statements 1 to 6, wherein n is 2.
8. The compound according to any of statements 1 to 7, wherein $R^0$ is amino.
9. The compound according to any of statements 1 to 8, wherein $R^2$ is hydrogen.
10. The compound according to statement 1, wherein the compound is selected from the group consisting of: Methyl-2-amino-5-(2-(4-methoxyphenyl)ethyl) thiophene-3-carboxylate; Methyl-2-amino-5-(2-(phenyl-ethyl)thiophene-3-carboxylate; Methyl-2-amino-5-(2-(2- methoxyphenyl)ethyl)thiophene-3-carboxylate; Methyl-2-amino-5-(2-(4-methoxy-2-methylphenyl)ethyl) thiophene-3-carboxylate; Methyl-2-amino-5-(2-(2-thienyl)ethyl)thiophene-3-carboxylate; Ethyl-2-amino-5-(2-(4-methoxyphenyl)ethynyl)thiophene-3-carboxylate; Ethyl-2-amino-5-(2-(4-methoxyphenyl)ethyl)thiophene-3-carboxylate; Ethyl-2-amino-5-(4-methoxyphenyl)thiophene-3-carboxylate; Ethyl-2-amino-5-(2-methoxyphenyl)thiophene-3-carboxylate; Ethyl-2-amino-5-(2-(2-methoxyphenyl)ethyl)thiophene-3-carboxylate; Ethyl-2-amino-4-ethoxycarbonyl 5-(2-(4-methoxyphenyl)ethyl) thiophene-3-carboxylate; Methyl-2-amino-5-(4-methoxyphenyl)thiophene-3-carboxylate; Methyl-2-amino-5-((2-methoxyphenyl)thiophene-3-carboxylate; 2-Amino-3-cyano-5-(4-methoxyphenyl)thiophene; Methyl-2-amino-5-(2,5-dimethoxyphenyl)thiophene-3-carboxylate; 2-Amino-3-cyano-5-(2-(2-methoxyphenyl)ethyl)thiophene; 2-Amino-3-cyano-5-(2-(4-methoxyphenyl)ethyl)thiophene; Ethyl-2-amino-5-(2-(2,5-dimethoxyphenyl)ethyl)thiophene-3-carboxylate; 2-Amino-3-cyano-5-(2-(phenyl)ethyl)thiophene; 2-Amino-3-cyano-5-(2-(2,5-dimethoxyphenyl)ethyl) thiophene; Ethyl-2-amino-4-ethoxycarbonyl-5-(2-(2,5-dimethoxymethoxyphenyl)ethyl)thiophene-3-carboxylate; Methyl-2-amino-5-(2-(2-pyridyl)ethyl)thiophene-3-carboxylate; Methyl-2-amino-5-(2-(3-pyridyl)ethyl) thiophene-3-carboxylate; Methyl-2-amino-4-methyl-5-(2-(2,5-dimethoxyphenyl)ethyl)thiophene-3-carboxylate; Methyl-2-amino-5-(2,5-dimethoxyphenyl)thiophene-3-carboxylate; N-Methyl-2-amino-5-(2-(4-methoxyphenyl)ethyl)thiophene-3-carboxamide; 2-Amino-5-(2-(4-methoxyphenyl)ethyl)thiophene-3-carboxylate; 2-Amino-5-(2-(4-methoxyphenyl)ethyl)thiophene-3-carboxamide; Methyl-2-methylamino-5-(2-(4-methoxyphenyl)ethyl) thiophene-3-carboxylate; Methyl-2-dimethylamino-5-(2-(4-methoxyphenyl)ethyl)thiophene-3-carboxylate; Methyl-5-(2-(4-methoxyphenyl)ethyl)thiophene-3-carboxylate; Methyl-2-amino-5-(2-(4-methoxyphenyl)sulfanylmethyl)thiophene-3-carboxylate; Methyl-2-amino-5-(2-(4-methoxyphenyl)oxymethyl)thiophene-3-carboxylate; Methyl-2-amino-5-(2-(4-methoxyphenyl)aminomethyl)thiophene-3-carboxylate; Methyl-2-amino-5-(2-(4-methylphenyl)sulfanylmethyl)thiophene-3-carboxylate; Methyl-2-amino-5-(2-(3-methylphenyl) sulfanylmethyl)thiophene-3-carboxylate; Methyl-2-amino-5-(2-(phenyl)methylsulfanylmethyl)thiophene-3-carboxylate; Methyl-2-amino-5-(2-(phenyl) sulfanylmethyl)thiophene-3-carboxylate; Methyl-2-phthalimido-5-(2-(4-methoxyphenyl)sulfanylmethyl) thiophene-3-carboxylate; and Methyl-2-phthalimido-5-(2-(3-methylphenyl)sulfanylmethyl)thiophene-3-carboxylate.

11. The compound according to statements 1 or 10 wherein the compound is selected from the group consisting of: Methyl-2-amino-5-(2-(4-methoxyphenyl)ethyl) thiophene-3-carboxylate; Methyl-2-amino-5-(2-(phenyl)ethyl)thiophene-3-carboxylate; Methyl-2-amino-5-(2-(2-methoxyphenyl)ethyl)thiophene-3-carboxylate; Methyl-2-amino-5-(2-(4-methoxy-2-methyl phenyl)ethyl) thiophene-3-carboxylate; Methyl-2-amino-5-(2-(2-thienyl)ethyl)thiophene-3-carboxylate; Ethyl-2-amino-5-(2-(4-methoxyphenyl)ethynyl)thiophene-3-carboxylate; and Ethyl-2-amino-5-(2-(4-methoxyphenyl)ethyl) thiophene-3-carboxylate.

12. A compound according to any of statements 1 to 11 or a compound selected from Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitrile; 2-Amino-5-benzylthiophene-3-carbonitrile; 2-Amino-5-isopropylthiophene-3-carbonitrile; 2-Amino-5-(tert-butyl)thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl) thiophene-3-carboxamide; 2-Amino-3-cyano-5-[2-(2',5'-dimethoxyphenyl)ethyl]-4-methylthiophene; 2-Amino-3-cyano-5-[2-(3',4',5'-trimethoxyphenyl) ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile; for use as a medicine.

13. A compound according to any of statements 1 to 12, or a compound selected from Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitile; 2-Amino-5-benzythiophene-3-carbonitrile; 2-Amino-5-isopropylthiophene-3-carbonitrile; 2-Amino-5-(tert-butyl)thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl)thiophene-3-carboxamide; 2-Amino-3-cyano-5-[2-(2',5'-dimethoxyphenyl) ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile; for use as a medicine for the prevention or treatment of cancer in a subject.

14. A compound according to statement 13, wherein said cancer is a lymphoma, liver cancer or prostate cancer.

15. A compound according to statement 14, wherein said lymphoma is a T-cell lymphoma.

16. A compound according to any of statements 13 to 15, wherein said subject is an animal or a human.

17. A pharmaceutical composition comprising a therapeutically effective amount of a compound according to any of statements 1 to 11 or a compound selected from Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitile; 2-Amino-5-benzythiophene-3-carbonitrile; 2-Amino-5-isopropylthiophene-3-carbonitrile; 2-Amino-5-(tert-butyl)thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl)thiophene-3-carboxamide; 2-Amino-3-cyano-5-[2-(2',5'-dimethoxyphenyl)ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile; and one or more pharmaceutically acceptable excipients.

18. A pharmaceutical composition for the prevention or treatment of cancer comprising a pharmaceutically acceptable carrier and as active ingredients a compound according to any of statements 1 to 11 or a compound selected from
Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitile; 2-Amino-5-benzythiophene-3-carbonitrile; 2-Amino-5-isopropylthiophene-3-carbonitrile; 2-Amino-5-(tert-butyl)thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl)thiophene-3-carboxamide; 2-Amino-3-cyano-5-[2-(2',5'-dimethoxyphenyl)ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile.

19. The pharmaceutical composition according to statement 17 or 18, further comprising one or more biologically active drugs being selected from the group consisting of antineoplastic drugs and/or immunosuppressant and/or immunomodulator drugs.

20. A method of prevention or treatment of cancer in an animal, comprising the administration of a therapeutically effective amount of a compound according to any of statements 1 to 11, or a compound selected from
Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitile; 2-Amino-5-benzythiophene-3-carbonitrile; 2-Amino-5-isopropylthiophene-3-carbonitrile; 2-Amino-5-(tert-butyl)thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl)thiophene-3-carboxamide; 2-Amino-3-cyano-5-[2-(2',5'-dimethoxyphenyl)ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile; optionally in combination with one or more pharmaceutically acceptable excipients.

21. A process for preparing a compound of formula I, Ia and Ib, comprising the steps of:
(a) a Gewald reaction of an enolizable compound (aldehyde or ketone), sulfur and an active methylene containing a cyano group;
(b) protection of the 5-amino group as phthalimide and further transformations at the 2-position of the thiophene starting from bromo or 2-bromomethyl derivatives; thus introducing the aromatic, heterocyclic or lipophilic side chain; and
(c) deprotection of the phthalimide function by hydrazine or methylhydrazine to liberate the 5-aminothiophene.

22. A compound selected from the group consisting of:
methyl 2-amino-5-propyl-thiophene-3-carboxylate; methyl 2-amino-5-(3-chloropropyl)thiophene-3-carboxylate; methyl 2-amino-5-butyl-thiophene-3-carboxylate; methyl 2-amino-5-pentyl-thiophene-3-carboxylate; methyl 2-amino-5-hexyl-thiophene-3-carboxylate; methyl 2-amino-5-heptyl-thiophene-3-carboxylate; methyl 2-amino-5-octyl-thiophene-3-carboxylate; methyl 2-amino-5-(1,5-dimethylhex-4-enyl)thiophene-3-carboxylate; 2-amino-5-non-8-enyl-thiophene-3-carbonitrile; methyl 2-amino-4-methyl-5-octyl-thiophene-3-carboxylate; methyl 2-amino-5-nonyl-thiophene-3-carboxylate; methyl 2-amino-5-decyl-thiophene-3-carboxylate; methyl 2-amino-5-dodecyl-thiophene-3-carboxylate; methyl 2-amino-5-tridecyl-thiophene-3-carboxylate; methyl 2-amino-5-tetradecyl-thiophene-3-carboxylate; methyl 2-amino-5-pentadecyl-thiophene-3-carboxylate; methyl 2-amino-5-hexadecyl-thiophene-3-carboxylate; methyl 2-amino-5-(butylthiomethyl)thiophene-3-carboxylate; methyl 2-amino-5-(pentylthiomethyl)thiophene-3-carboxylate; methyl 2-amino-5-(isopentylthiomethyl)thiophene-3-carboxylate; methyl 2-amino-5-(hexylthiomethyl)thiophene-3-carboxylate; methyl 2-amino-5-

(heptylthiomethyl)thiophene-3-carboxylate; methyl 2-amino-5-(octylthiomethyl)thiophene-3-carboxylate; methyl 2-amino-5-(cyclopentylthiomethyl)thiophene-3-carboxylate; methyl 2-amino-5-(cyclohexylthiomethyl)thiophene-3-carboxylate; methyl 2-amino-5-(phenylthiomethyl)thiophene-3-carboxylate; methyl 2-amino-5-(p-tolylthiomethyl)thiophene-3-carboxylate; methyl 2-amino-5-(o-tolylthiomethyl)thiophene-3-carboxylate; methyl 2-amino-5-(m-tolylthiomethyl)thiophene-3-carboxylate; methyl 2-amino-5-[(2-aminophenyl)thiomethyl]thiophene-3-carboxylate; methyl 2-amino-5-[(4-methoxyphenyl)thiomethyl]thiophene-3-carboxylate; methyl 2-amino-5-[(2-methoxyphenyl)thiomethyl]thiophene-3-carboxylate; methyl 2-amino-5-[(2-methoxycarbonylphenyl)thiomethyl]thiophene-3-carboxylate; 3-((5-amino-4-(methoxycarbonyl)thiophen-2-yl)methylthio)benzoic acid; methyl 2-amino-5-[(4-fluorophenyl)thiomethyl]thiophene-3-carboxylate; methyl 2-amino-5-[(4-chlorophenyl)thiomethyl]thiophene-3-carboxylate; methyl 2-amino-5-[(4-nitrophenyl)thiomethyl]thiophene-3-carboxylate; methyl 2-amino-5-[(4-ethylphenyl)thiomethyl]thiophene-3-carboxylate; methyl 2-amino-5-[(4-isopropylphenyl)thiomethyl]thiophene-3-carboxylate; methyl 2-amino-5-[(4-methoxyphenyl)methylthiomethyl]thiophene-3-carboxylate; methyl 2-amino-5-[(phenyl)methylthiomethyl]thiophene-3-carboxylate; methyl 2-amino-5-(phenethylthiomethyl)thiophene-3-carboxylate; methyl 2-amino-5-[(biphenyl-4-yl)thiomethyl]thiophene-3-carboxylate; methyl 2-amino-5-(2-naphthylthiomethyl)thiophene-3-carboxylate; methyl 2-amino-5-(4-pyridylthiomethyl)thiophene-3-carboxylate; methyl 2-amino-5-(2-thienylmethylthiomethyl)thiophene-3-carboxylate; methyl 2-amino-5-(2-furylmethylthiomethyl)thiophene-3-carboxylate; methyl 2-amino-5-(3-cyclohexylthiopropyl)thiophene-3-carboxylate; methyl 2-amino-5-[3-(4-methoxyphenyl)thiopropyl]thiophene-3-carboxylate.

23. A pharmaceutical composition comprising a therapeutically effective amount of a compound according to statement 22 and one or more pharmaceutically acceptable excipients.

24. The pharmaceutical composition according to statement 23, further comprising one or more biologically active drugs being selected from the group consisting of antineoplastic drugs and/or immunosuppressant and/or immunomodulator drugs.

25. A compound according to statement 22, or a pharmaceutical composition according to statement 23 or 24 for use as a medicine.

26. A compound according to statement 22, or a pharmaceutical composition according to statement 23 or 24, for use as a medicine for the prevention or treatment of cancer in a subject, preferably wherein said subject is an animal or human.

27. A compound according to statement 22, or a pharmaceutical composition according to statement 23 or 24, for use as a medicine for the prevention or treatment of cancer in a subject, wherein said cancer is a lymphoma, liver cancer or prostate cancer; preferably a T-cell lymphoma, preferably wherein said subject is an animal or human.

28. A compound having the general formula I, Ia, or Ib: wherein
A is selected from the group consisting of heteroaryl and aryl groups; $C_{1-7}$ alkyl; $C_{2-7}$ alkenyl; $C_{2-7}$ alkynyl; halo $C_{1-7}$ alkyl; $C_{3-10}$ cycloalkyl; $C_{1-7}$ alkoxy; $C_{3-10}$ cycloalkoxy; aryloxy; arylalkyloxy; oxyheterocyclic; thio $C_{1-7}$ alkyl; thio $C_{3-10}$ cycloalkyl; arylthio; arylalkylthio; heterocyclic-substituted alkyl; heterocyclic-substituted alkyloxy, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, and wherein said alkyl is optionally substituted with one or more substituents selected from the group consisting of halogen, nitro, hydroxyl, sulfhydryl, amino, azido;

$R^0$ is independently selected from the group consisting of hydrogen, amino, (mono- or di) $C_{1-7}$ alkylamino, (mono- or di) arylamino; azido; 1H-Isoindole-1,3(2H)-dione,2-methyl-;

$R^1$ is independently selected from the group consisting of hydrogen; carboxy$C_{1-7}$ alkyl; cyano; —COOH; CON-$R^aR^b$; SO$_2$R; SO$_2$NHR; SO$_2$NR$^a$R$^b$, SO$_2$OR; PO(XR)$_2$; and $C_{3-10}$ cycloalkyl, wherein R, $R^a$ and $R^b$ are each independently selected from the group consisting of H and $C_{1-7}$alkyl and $C_{3-10}$ cycloalkyl;

$R^2$ is independently selected from the group consisting of hydrogen; carboxy$C_{1-7}$ alkyl, $C_{1-7}$alkyl; cyano; —CONHMe; —COOH; —CONH$_2$ X is independently selected from the group consisting of —(CH$_2$)$_n$, —(CH$_2$)$_n$-acetylene, —(CH$_2$)$_n$-ethylene, —S(CH$_2$)$_n$—, —O(CH$_2$)$_n$—, —NH(CH$_2$)$_n$—; —(CH$_2$)$_n$S(CH$_2$)$_n$—, wherein n is 0, 1, 2, 3, 4, 5, 6 or 7;

$R^3$, $R^4$, $R^5$, $R^6$ and $R^7$ are independently selected from the group consisting of hydrogen; $C_{1-7}$alkyl; $C_{1-7}$ alkoxy; halogen; amino; (mono- or di) $C_{1-7}$ alkylamino, (mono- or di) arylamino; azido; hydroxyl; $C_{3-10}$ cycloalkyl, and wherein said alkyl is optionally substituted with one or more substituents selected from the group consisting of halogen, nitro, hydroxyl, sulfhydryl, amino, azido;

and/or a pharmaceutical acceptable addition salt thereof and/or a stereoisomer thereof and/or a solvate thereof.

29. The compound according to statement 28, wherein A is phenyl or thiophene.

30. The compound according to statement 28 or 29, wherein $R^1$ is a carboxymethyl or carboxyethyl group.

31. The compound according to any of statements 28 to 30, wherein A is an aryl group substituted with 1 or 2 substituents selected from the group consisting of a methoxy group and a methyl group.

32. The compound according to any of statements 28 to 31, wherein X is selected from the group consisting of a —(CH$_2$)$_2$—, an ethylene and an acetylene group.

33. The compound according to any of statements 28 to 32, wherein n is 2.

34. The compound according to any of statements 28 to 33, wherein $R^0$ is amino.

35. The compound according to any of statements 28 to 34, wherein $R^2$ is hydrogen.

36. The compound according to statement 28, wherein the compound is selected from the group consisting of: Methyl-2-amino-5-(2-(4-methoxyphenyl)ethyl)thiophene-3-carboxylate; Methyl-2-amino-5-(2-(phenyl-ethyl)thiophene-3-carboxylate; Methyl-2-amino-5-(2-(2-methoxyphenyl)ethyl)thiophene-3-carboxylate; Methyl-2-amino-5-(2-(4-methoxy-2-methyl phenyl)ethyl)thiophene-3-carboxylate; Methyl-2-amino-5-(2-(2-thienyl)ethyl)thiophene-3-carboxylate; Ethyl-2-amino-5-(2-(4-methoxyphenyl)ethynyl)thiophene-3-carboxylate; Ethyl-2-amino-5-(2-(4-methoxyphenyl)ethyl)thiophene-3-carboxylate; Ethyl 2-amino-5-(4-methoxyphenyl)

thiophene-3-carboxylate; Ethyl-2-amino-5-(2-methoxyphenyl)thiophene-3-carboxylate; Ethyl-2-amino-5-(2-(2-methoxyphenyl)ethyl)thiophene-3-carboxylate; Ethyl-2-amino-4-ethoxycarbonyl 5-(2-(4-methoxyphenyl)ethyl)thiophene-3-carboxylate; Methyl-2-amino-5-(4-methoxyphenyl)thiophene-3-carboxylate; Methyl-2-amino-5-((2-methoxyphenyl)thiophene-3-carboxylate; 2-Amino-3-cyano-5-(4-methoxyphenyl)thiophene; Methyl-2-amino-5-(2,5-dimethoxyphenyl)thiophene-3-carboxylate; 2-Amino-3-cyano-5-(2-(2-methoxyphenyl)ethyl)thiophene; 2-Amino-3-cyano-5-(2-(4-methoxyphenyl)ethyl)thiophene; Ethyl 2-amino-5-(2-(2,5-dimethoxyphenyl)ethyl)thiophene-3-carboxylate; 2-Amino-3-cyano-5-(2-(phenyl)ethyl)thiophene; 2-Amino-3-cyano-5-(2-(2,5-dimethoxyphenyl)ethyl)thiophene; Ethyl 2-amino-4-ethoxycarbonyl 5-(2-(2,5-dimethoxymethoxyphenyl)ethyl)thiophene-3-carboxylate; Methyl-2-amino-5-(2-(2-pyridyl)ethyl)thiophene-3-carboxylate; Methyl-2-amino-5-(2-(3-pyridyl)ethyl)thiophene-3-carboxylate; Methyl-2-amino-4-methyl-5-(2-(2,5-dimethoxyphenyl)ethyl)thiophene-3-carboxylate; Methyl-2-amino-5-(2,5-dimethoxyphenyl)thiophene-3-carboxylate; N-Methyl 2-amino-5-(2-(4-methoxyphenyl)ethyl)thiophene-3-carboxamide; 2-Amino-5-(2-(4-methoxyphenyl)ethyl)thiophene-3-carboxylate; 2-Amino-5-(2-(4-methoxyphenyl)ethyl)thiophene-3-carboxamide; Methyl-2-methylamino-5-(2-(4-methoxyphenyl)ethyl)thiophene-3-carboxylate; Methyl-2-dimethylamino-5-(2-(4-methoxyphenyl)ethyl)thiophene-3-carboxylate; Methyl-5-(2-(4-methoxyphenyl)ethyl)thiophene-3-carboxylate; Methyl-2-amino-5-(2-(4-methoxyphenyl)sulfanylmethyl)thiophene-3-carboxylate; Methyl-2-amino-5-(2-(4-methoxyphenyl)oxymethyl)thiophene-3-carboxylate; Methyl-2-amino-5-(2-(4-methoxyphenyl)aminomethyl)thiophene-3-carboxylate; Methyl-2-amino-5-(2-(4-methylphenyl)sulfanylmethyl)thiophene-3-carboxylate; Methyl-2-amino-5-(2-(3-methylphenyl)sulfanylmethyl)thiophene-3-carboxylate; Methyl-2-amino-5-(2-(phenyl)methylsulfanylmethyl)thiophene-3-carboxylate; Methyl-2-amino-5-(2-(phenyl)sulfanylmethyl)thiophene-3-carboxylate; Methyl-2-phthalimido-5-(2-(4-methoxyphenyl)sulfanylmethyl)thiophene-3-carboxylate; and Methyl-2-phthalimido-5-(2-(3-methylphenyl)sulfanylmethyl)thiophene-3-carboxylate.

37. The compound according to statement 28 or 36 wherein the compound is selected from the group consisting of: Methyl-2-amino-5-(2-(4-methoxyphenyl)ethyl)thiophene-3-carboxylate; Methyl-2-amino-5-(2-(phenyl-ethyl)thiophene-3-carboxylate; Methyl-2-amino-5-(2-(2-methoxyphenyl)ethyl)thiophene-3-carboxylate; Methyl-2-amino-5-(2-(4-methoxy-2-methylphenyl)ethyl)thiophene-3-carboxylate; Methyl-2-amino-5-(2-(2-thienyl)ethyl)thiophene-3-carboxylate; Ethyl-2-amino-5-(2-(4-methoxyphenyl)ethynyl)thiophene-3-carboxylate; and Ethyl-2-amino-5-(2-(4-methoxyphenyl)ethyl)thiophene-3-carboxylate.

38. A compound according to any of statements 28 to 37 for use as a medicine.

39. A compound according to any of statements 28 to 38 for use as a medicine for the prevention or treatment of cancer in a subject.

40. A compound according to statement 39, wherein said cancer is a lymphoma, liver cancer or prostate cancer.

41. A compound according to statement 40, wherein said lymphoma is a T-cell lymphoma.

42. A compound according to any of statements 39 to 41, wherein said subject is an animal or a human.

43. A pharmaceutical composition comprising a therapeutically effective amount of a compound according to any of statements 28 to 37 and one or more pharmaceutically acceptable excipients.

44. A pharmaceutical composition for the prevention or treatment of cancer comprising a pharmaceutically acceptable carrier and as active ingredients a compound according to any of statements 28 to 37.

45. The pharmaceutical composition according to statement 43 or 44, further comprising one or more biologically active drugs being selected from the group consisting of antineoplastic drugs and/or immunosuppressant and/or immunomodulator drugs.

46. A method of prevention or treatment of cancer in an animal, comprising the administration of a therapeutically effective amount of a compound according to any of statements 28 to 37, optionally in combination with one or more pharmaceutically acceptable excipients.

47. A process for preparing a compound of formula I, Ia and Ib according to any of statements 28 to 37, comprising the steps of:
   (a) a Gewald reaction of an enolizable compound (aldehyde or ketone), sulfur and an active methylene containing a cyano group;
   (b) protection of the 5-amino group as phthalimide and further transformations at the 2-position of the thiophene starting from bromo or 2-bromomethyl derivatives; thus introducing the aromatic, heterocyclic or lipophilic side chain; and
   (c) deprotection of the phthalimide function by hydrazine or methylhydrazine to liberate the 5-aminothiophene.

48. A compound having the general formula I, Ia, or Ib:

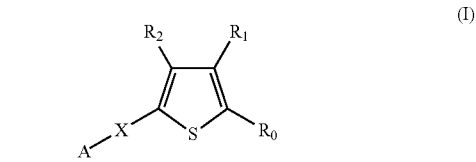

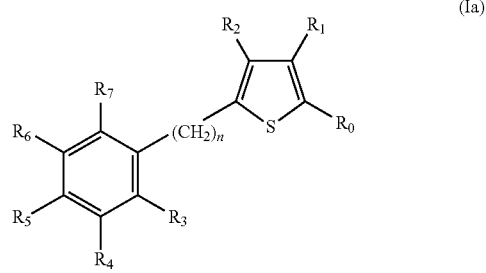

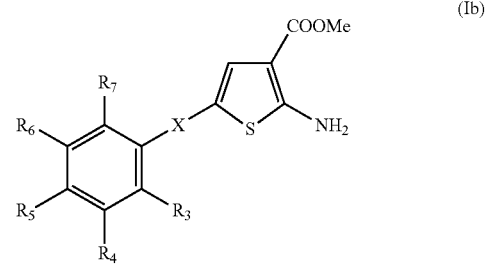

wherein
- A is selected from the group consisting of $C_{1-7}$ alkyl; $C_{2-7}$ alkenyl; $C_{2-7}$ alkynyl; halo-$C_{1-7}$ alkyl; $C_{3-10}$ cycloalkyl; $C_{1-7}$ alkoxy; $C_{3-10}$ cycloalkoxy; aryloxy; arylalkyloxy; oxyheterocyclic; thio $C_{1-7}$ alkyl; thio $C_{3-10}$ cycloalkyl; arylthio; arylalkylthio; heterocyclic-substituted alkyl; heterocyclic-substituted alkyloxy; heteroaryl and aryl groups, wherein said heteroaryl or aryl groups are optionally substituted with one or more substituents selected from the group consisting of halogen, $C_{1-7}$ alkyl, $C_{2-7}$-alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, and wherein said alkyl is optionally substituted with one or more substituents selected from the group consisting of halogen, nitro, hydroxyl, sulfhydryl, amino, azido;
- $R^0$ is independently selected from the group consisting of amino; (mono- or di) $C_{1-7}$ alkylamino; (mono- or di) arylamino; azido; 1H-Isoindole-1,3(2H)-dione,2-methyl-;
- $R^1$ is independently selected from the group consisting of carboxy$C_{1-7}$ alkyl; cyano; —COOH; CONR$^a$R$^b$; SO2R; SO2NHR; SO2NR$^a$R$^b$, SO2OR; PO(XR)2; and $C_{3-10}$ cycloalkyl, wherein R, R$^a$ and R$^b$ are each independently selected from the group consisting of H and $C_{1-7}$alkyl and $C_{3-10}$ cycloalkyl;
- wherein when X is $C_2$ alkynyl (acetylene bridge) in formula I, then $R^1$ is carboxy$C_{1-7}$ alkyl;
- $R^2$ is independently selected from the group consisting of hydrogen; carboxy$C_{1-7}$ alkyl, $C_{1-7}$alkyl; cyano; —CONHMe; —COOH; —CONH$_2$
- X is independently selected from the group consisting of —(CH$_2$)$_n$, —(CH$_2$)$_m$-acetylene, -acetylene-(CH$_2$)$_m$—, —(CH$_2$)$_m$-ethylene, -ethylene-(CH$_2$)$_m$—, —S(CH$_2$)$_m$—, —(CH$_2$)$_m$S—, —O(CH$_2$)$_m$—, —(CH$_2$)$_m$O—, —NH(CH$_2$)$_m$—; —(CH$_2$)$_m$NH—, —(CH$_2$)$_m$S(CH$_2$)$_p$—, —(CH$_2$)$_m$O(CH$_2$)$_p$, wherein m is 0, 1, 2, 3, 4, 5, 6 or 7, and wherein p is 0, 1, 2, 3, 4, 5, 6 or 7, and wherein n is 2, 3, 4, 5, 6 or 7;
- $R^3$, $R^4$, $R^5$, $R^6$ and $R^7$ are independently selected from the group consisting of hydrogen; $C_{1-7}$alkyl; $C_{1-7}$ alkoxy; halogen; amino; (mono- or di) $C_{1-7}$ alkylamino, (mono- or di) arylamino; azido; hydroxyl; $C_{3-10}$ cycloalkyl, and wherein said alkyl is optionally substituted with one or more substituents selected from the group consisting of halogen, nitro, hydroxyl, sulfhydryl, amino, azido;

and/or a pharmaceutical acceptable addition salt thereof and/or a stereoisomer thereof and/or a solvate thereof.

49. The compound according to statement 48, wherein A is $C_{1-7}$ alkyl or $C_{2-7}$ alkenyl.
50. The compound according to statement 48, wherein A is phenyl or thiophene.
51. The compound according to any of statements 48 to 50, wherein $R^1$ is a carboxymethyl or carboxyethyl group.
52. The compound according to any of statements 48, 50 and 51, wherein A is an aryl group substituted with 1 or 2 substituents selected from the group consisting of a methoxy group and a methyl group.
53. The compound according to any of statements 48 to 52, wherein X is selected from the group consisting of a —(CH$_2$)$_2$—, an ethylene and an acetylene group.
54. The compound according to any of statements 48 to 53, wherein n is 2.
55. The compound according to any of statements 48 to 54, wherein $R^0$ is amino.
56. The compound according to any of statements 48 to 55, wherein $R^2$ is hydrogen.
57. The compound according to statement 48, wherein the compound is selected from the group consisting of: Methyl-2-amino-5-(2-(4-methoxyphenyl)ethyl) thiophene-3-carboxylate; Methyl-2-amino-5-(2-(phenyl-ethyl)thiophene-3-carboxylate; Methyl-2-amino-5-(2-(2-methoxyphenyl)ethyl)thiophene-3-carboxylate; Methyl-2-amino-5-(2-(4-methoxy-2-methyl phenyl)ethyl) thiophene-3-carboxylate; Methyl-2-amino-5-(2-(2-thienyl)ethyl)thiophene-3-carboxylate; Ethyl-2-amino-5-(2-(4-methoxyphenyl)ethynyl)thiophene-3-carboxylate; Ethyl-2-amino-5-(2-(4-methoxyphenyl)ethyl)thiophene-3-carboxylate; Ethyl-2-amino-5-(4-methoxyphenyl) thiophene-3-carboxylate; Ethyl-2-amino-5-(2-methoxyphenyl)thiophene-3-carboxylate; Ethyl-2-amino-5-(2-(2-methoxyphenyl)ethyl)thiophene-3-carboxylate; Ethyl-2-amino-4-ethoxycarbonyl-5-(2-(4-methoxyphenyl) ethyl)thiophene-3-carboxylate; Methyl-2-amino-5-(4-methoxyphenyl)thiophene-3-carboxylate; Methyl-2-amino-5-((2-methoxyphenyl)thiophene-3-carboxylate; 2-Amino-3-cyano-5-(4-methoxyphenyl)thiophene; Methyl-2-amino-5-(2,5-dimethoxyphenyl)thiophene-3-carboxylate; 2-Amino-3-cyano-5-(2-(2-methoxyphenyl) ethyl)thiophene; 2-Amino-3-cyano-5-(2-(4-methoxyphenyl)ethyl)thiophene; Ethyl-2-amino-5-(2-(2,5-dimethoxyphenyl)ethyl)thiophene-3-carboxylate; 2-Amino-3-cyano-5-(2-(phenyl)ethyl)thiophene; 2-Amino-3-cyano-5-(2-(2,5-dimethoxyphenyl)ethyl) thiophene; Ethyl-2-amino-4-ethoxycarbonyl-5-(2-(2,5-dimethoxymethoxyphenyl)ethyl)thiophene-3-carboxylate; Methyl-2-amino-5-(2-(2-pyridyl)ethyl)thiophene-3-carboxylate; Methyl-2-amino-5-(2-(3-pyridyl)ethyl) thiophene-3-carboxylate; Methyl-2-amino-4-methyl-5-(2-(2,5-dimethoxyphenyl)ethyl)thiophene-3-carboxylate; Methyl-2-amino-5-(2,5-dimethoxyphenyl)thiophene-3-carboxylate; N-Methyl-2-amino-5-(2-(4-methoxyphenyl) ethyl)thiophene-3-carboxamide; 2-Amino-5-(2-(4-methoxyphenyl)ethyl)thiophene-3-carboxylate; 2-Amino-5-(2-(4-methoxyphenyl)ethyl)thiophene-3-carboxamide; Methyl-2-methylamino-5-(2-(4-methoxyphenyl)ethyl) thiophene-3-carboxylate; Methyl-2-dimethylamino-5-(2-(4-methoxyphenyl)ethyl)thiophene-3-carboxylate; Methyl-5-(2-(4-methoxyphenyl)ethyl)thiophene-3-carboxylate; Methyl-2-amino-5-(2-(4-methoxyphenyl)sulfanylmethyl)thiophene-3-carboxylate; Methyl-2-amino-5-(2-(4-methoxyphenyl)oxymethyl)thiophene-3-carboxylate; Methyl-2-amino-5-(2-(4-methoxyphenyl) aminomethyl)thiophene-3-carboxylate; Methyl-2-amino-5-(2-(4-methylphenyl)sulfanylmethyl)thiophene-3-carboxylate; Methyl-2-amino-5-(2-(3-methylphenyl) sulfanylmethyl)thiophene-3-carboxylate; Methyl-2-amino-5-(2-(phenyl)methylsulfanylmethyl)thiophene-3-carboxylate; Methyl-2-amino-5-(2-(phenyl) sulfanylmethyl)thiophene-3-carboxylate; Methyl-2-phthalimido-5-(2-(4-methoxyphenyl)sulfanylmethyl) thiophene-3-carboxylate; and Methyl-2-phthalimido-5-(2-(3-methylphenyl)sulfanylmethyl)thiophene-3-carboxylate.
58. The compound according to statement 48 or 57 wherein the compound is selected from the group consisting of: Methyl-2-amino-5-(2-(4-methoxyphenyl)ethyl) thiophene-3-carboxylate; Methyl-2-amino-5-(2-(phenyl-ethyl)thiophene-3-carboxylate; Methyl-2-amino-5-(2-(2-methoxyphenyl)ethyl)thiophene-3-carboxylate; Methyl-2-amino-5-(2-(4-methoxy-2-methyl phenyl)ethyl) thiophene-3-carboxylate; Methyl-2-amino-5-(2-(2- thienyl)ethyl)thiophene-3-carboxylate; Ethyl-2-amino-5-(2-(4-methoxyphenyl)ethynyl)thiophene-3-carboxylate; and Ethyl-2-amino-5-(2-(4-methoxyphenyl)ethyl)thiophene-3-carboxylate.

59. A compound according to any of statements 48 to 58 for use as a medicine.
60. A compound according to any of statements 48 to 58 for use as a medicine for the prevention or treatment of cancer in a subject.
61. A compound according to statement 60, wherein said cancer is a lymphoma, liver cancer or prostate cancer.
62. A compound according to statement 61, wherein said lymphoma is a T-cell lymphoma.
63. A compound according to any of statements 60 to 62, wherein said subject is an animal or a human.
64. A pharmaceutical composition comprising a therapeutically effective amount of a compound according to any of statements 48 to 58 and one or more pharmaceutically acceptable excipients.
65. A pharmaceutical composition for the prevention or treatment of cancer comprising a pharmaceutically acceptable carrier and as active ingredients a compound according to any of statements 48 to 58.
66. The pharmaceutical composition according to statement 64 or 65, further comprising one or more biologically active drugs being selected from the group consisting of antineoplastic drugs and/or immunosuppressant and/or immunomodulator drugs.
67. A method of prevention or treatment of cancer in an animal, comprising the administration of a therapeutically effective amount of a compound according to any of statements 48 to 58, optionally in combination with one or more pharmaceutically acceptable excipients.
68. A process for preparing a compound of formula I, Ia and Ib, comprising the steps of:
(a) a Gewald reaction of an enolizable compound (aldehyde or ketone), sulfur and an active methylene containing a cyano group;
(b) protection of the 5-amino group as phthalimide and further transformations at the 2-position of the thiophene starting from bromo or 2-bromomethyl derivatives; thus introducing the aromatic, heterocyclic or lipophilic side chain; and
(c) deprotection of the phthalimide function by hydrazine or methylhydrazine to liberate the 5-aminothiophene.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION OF THE INVENTION

Figure 1A:
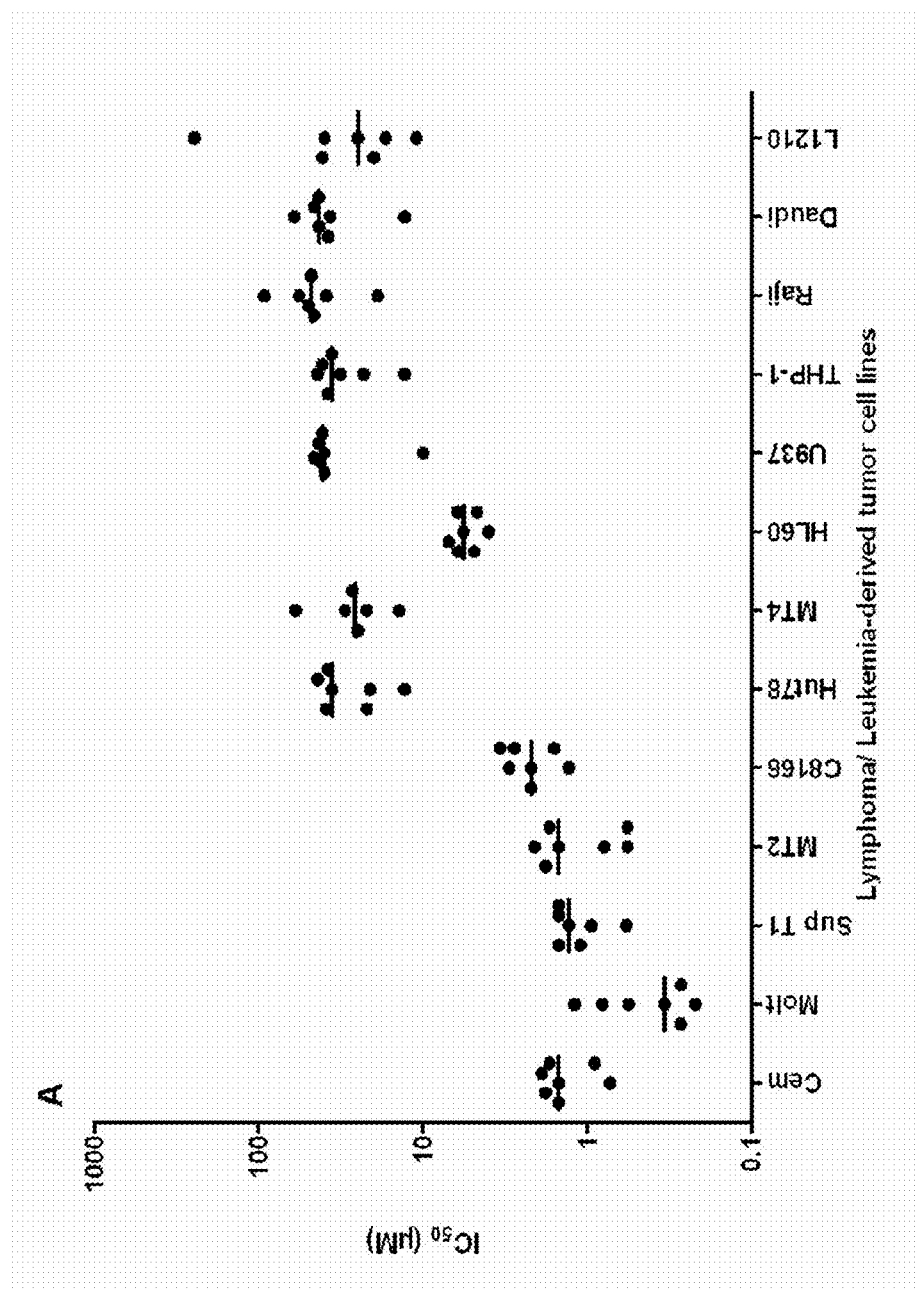
FIG. 1. Cytostatic activity of 2-aminothiophene derivatives against a variety of tumor and non-tumorigenic cell lines.

One aspect of this invention concerns the compounds of formula I, Ia and Ib:

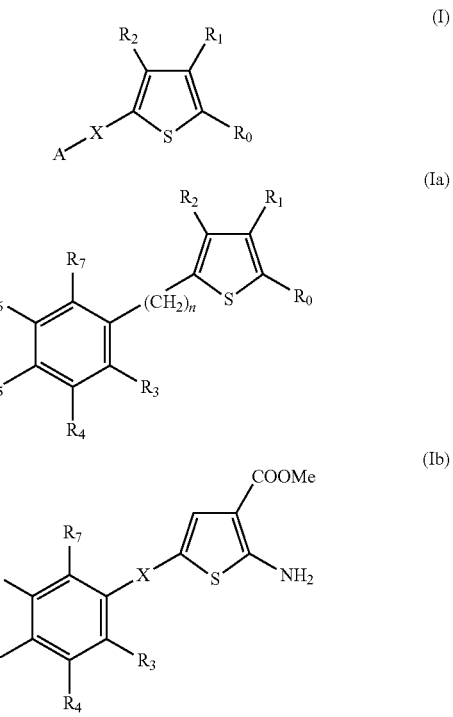

wherein,
A is selected from the group consisting of $C_{1-7}$ alkyl; $C_{2-7}$ alkenyl; $C_{2-7}$ alkynyl; halo $C_{1-7}$ alkyl; $C_{3-10}$ cycloalkyl; $C_{1-7}$ alkoxy; $C_{3-10}$ cycloalkoxy; aryloxy; arylalkyloxy; oxyheterocyclic; thio $C_{1-7}$ alkyl; thio $C_{3-10}$ cycloalkyl; arylthio; arylalkylthio; heterocyclic-substituted alkyl; heterocyclic-substituted alkyloxy; heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, and wherein said alkyl is optionally substituted with one or more substituents selected from the group consisting of halogen, nitro, hydroxyl, sulfhydryl, amino, azido; for example A is selected from the group consisting of $C_{1-7}$ alkyl; $C_{2-7}$ alkenyl; $C_{2-7}$ alkynyl; halo $C_{1-7}$ alkyl; $C_{3-10}$ cycloalkyl; thio $C_{1-7}$ alkyl; thio $C_{3-10}$ cycloalkyl; arylthio; arylalkylthio; heterocyclic-substituted alkyl; heterocyclic-substituted alkyloxy; heteroaryl and aryl groups, wherein said heteroaryl or aryl groups are optionally substituted with one or more substituents, for example 1, 2, or 3 substituents each independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, and wherein said alkyl is optionally substituted with one or more substituents selected from the group consisting of halogen, nitro, hydroxyl, sulfhydryl, amino; for example A is selected from the group consisting of $C_{1-7}$ alkyl; $C_{2-7}$ alkenyl; $C_{2-7}$ alkynyl; halo $C_{1-7}$ alkyl; $C_{3-10}$ cycloalkyl; thio $C_{1-7}$ alkyl; thio$C_{3-10}$cycloalkyl; arylthio; arylalkylthio; heterocyclic-substituted alkyl; heteroaryl and aryl groups, wherein said heteroaryl or aryl groups are optionally substituted with 1, 2, or 3 substituents each independently selected from the group consisting of halogen, $C_{1-7}$ alkyl, halo $C_{1-7}$ alkyl, nitro, hydroxyl, amino, $C_{1-7}$ alkoxy, and wherein said alkyl is optionally substituted with one or more substituents selected from the group consisting of halogen, nitro, hydroxyl, amino;

$R^0$ is independently selected from the group consisting of amino; (mono- or di) $C_{1-7}$ alkylamino; (mono- or di) arylamino; azido; 1H-Isoindole-1,3(2H)-dione,2-methyl-; preferably $R^0$ is independently selected from the group consisting of amino; (mono- or di) $C_{1-4}$ alkylamino; (mono- or di) arylamino; preferably $R^0$ is independently selected from the group consisting of amino; (mono- or di) $C_{1-4}$ alkylamino; more preferably $R^0$ is amino;

$R^1$ is independently selected from the group consisting of carboxy$C_{1-7}$ alkyl; cyano; —COOH; CONR$^a$R$^b$; SO$_2$R; SO$_2$NHR; SO$_2$NR$^a$R$^b$, SO$_2$OR; PO(XR)$_2$; and $C_{3-10}$ cycloalkyl, wherein R, R$^a$ and R$^b$ are each independently selected from the group consisting of H and $C_{1-7}$ alkyl and $C_{3-10}$ cycloalkyl; preferably $R^1$ is independently selected from the group consisting of carboxy$C_{1-7}$ alkyl; cyano; —COOH; CONR$^a$R$^b$; SO$_2$R; SO$_2$NHR; SO$_2$NR$^a$R$^b$, SO$_2$OR; PO(XR)$_2$; and $C_{3-10}$ cycloalkyl, wherein R, R$^a$ and R$^b$ are each independently selected from the group consisting of H and $C_{1-7}$ alkyl; preferably $R^1$ is independently selected from the group consisting of carboxy$C_{1-7}$ alkyl; cyano; —COOH; CONR$^a$R$^b$, wherein R, R$^a$ and R$^b$ are each independently selected from the group consisting of H and $C_{1-7}$ alkyl; preferably $R^1$ is independently selected from carboxy$C_{1-6}$alkyl; or cyano; preferably $R^1$ is independently selected from carboxy$C_{1-4}$alkyl; or cyano; preferably $R^1$ is independently selected from carboxy$C_{1-2}$alkyl; or cyano;

$R^2$ is independently selected from the group consisting of hydrogen; carboxy$C_{1-7}$ alkyl, $C_{1-7}$alkyl; cyano; —CONHMe; —COOH; —CONH$_2$; preferably $R^2$ is independently selected from the group consisting of hydrogen; carboxy$C_{1-7}$ alkyl, $C_{1-7}$alkyl; COOH; preferably $R^2$ is independently selected from the group consisting of hydrogen; carboxy$C_{1-7}$ alkyl, $C_{1-7}$alkyl; preferably $R^2$ is independently selected from the group consisting of hydrogen; carboxy$C_{1-6}$ alkyl, $C_{1-6}$alkyl; preferably $R^2$ is independently selected from the group consisting of hydrogen; carboxy$C_{1-4}$ alkyl, $C_{1-4}$alkyl; preferably $R^2$ is independently selected from the group consisting of hydrogen; carboxy$C_{1-2}$ alkyl, $C_{1-2}$alkyl;

X is independently selected from the group consisting of —(CH$_2$)$_n$, —(CH$_2$)$_m$-acetylene, -acetylene-(CH$_2$)$_m$—, —(CH$_2$)$_m$-ethylene, -ethylene-(CH$_2$)$_m$—, —S(CH$_2$)$_m$—, —(CH$_2$)$_m$S—, —O(CH$_2$)$_m$—, —(CH$_2$)$_m$O—, —NH(CH$_2$)$_m$—; —(CH$_2$)$_m$NH—, —(CH$_2$)$_m$S(CH$_2$)$_p$—, —(CH$_2$)$_m$O(CH$_2$)$_p$, wherein m is 0, 1, 2, 3, 4, 5, 6 or 7, and wherein p is 0, 1, 2, 3, 4, 5, 6 or 7, and wherein n is 2, 3, 4, 5, 6 or 7; preferably X is independently selected from the group consisting of —(CH$_2$)$_n$, —(CH$_2$)$_m$-acetylene, -acetylene-(CH$_2$)$_m$—, —(CH$_2$)$_m$-ethylene, -ethylene-(CH$_2$)$_m$—, —S(CH$_2$)$_m$—, —(CH$_2$)$_m$S—, —(CH$_2$)$_m$S(CH$_2$)$_p$—, wherein m is 0, 1, 2, 3, 4, 5, 6 or 7, and wherein p is 0, 1, 2, 3, 4, 5, 6 or 7, and wherein n is 2, 3, 4, 5, 6 or 7; preferably X is independently selected from the group consisting of —(CH$_2$)$_n$, —(CH$_2$)$_m$-acetylene, -acetylene-(CH$_2$)$_m$—, —(CH$_2$)$_m$-ethylene, -ethylene-(CH$_2$)$_m$—, —S(CH$_2$)$_m$—, —(CH$_2$)$_m$S—, —(CH$_2$)$_m$S(CH$_2$)$_p$—, wherein m is 0, 1, 2, 3, 4, 5, or 6, and wherein p is 0, 1, 2, 3, 4, 5, or 6, and wherein n is 2, 3, 4, 5, or 6; preferably wherein m is 0, 1, 2, 3, 4, or 5, and wherein p is 0, 1, 2, 3, 4, or 5, and wherein n is 2, 3, 4, or 5;

$R^3$, $R^4$, $R^5$, $R^6$ and $R^7$ are independently selected from the group consisting of hydrogen; $C_{1-7}$alkyl; $C_{1-7}$ alkoxy; halogen; amino; (mono- or di) $C_{1-7}$ alkylamino, (mono- or di) arylamino; azido; hydroxyl; $C_{3-10}$ cycloalkyl, and wherein said alkyl is optionally substituted with one or more substituents selected from the group consisting of halogen, nitro, hydroxyl, sulfhydryl, amino, azido; preferably $R^3$, $R^4$, $R^5$, $R^6$ and $R^7$ are independently selected from the group consisting of hydrogen; $C_{1-7}$alkyl; $C_{1-7}$ alkoxy; halogen; amino; (mono- or di) $C_{1-7}$ alkylamino, hydroxyl; $C_{3-10}$ cycloalkyl, and wherein said alkyl is optionally substituted with one or more substituents selected from the group consisting of halogen, nitro, hydroxyl, sulfhydryl, amino; preferably $R^3$, $R^4$, $R^5$, $R^6$ and $R^7$ are independently selected from the group consisting of hydrogen; $C_{1-6}$alkyl; $C_{1-6}$alkoxy; halogen; amino; hydroxyl; and wherein said alkyl is optionally substituted with one or more substituents selected from the group consisting of halogen, nitro, or hydroxyl; preferably $R^3$, $R^4$, $R^5$, $R^6$ and $R^7$ are independently selected from the group consisting of hydrogen; $C_{1-6}$alkyl; $C_{1-6}$alkoxy; halogen; preferably $R^3$, $R^4$, $R^5$, $R^6$ and $R^7$ are independently selected from the group consisting of hydrogen; $C_{1-4}$alkyl; $C_{1-4}$alkoxy; and halogen;

and/or a pharmaceutical acceptable addition salt thereof and/or a stereoisomer thereof and/or a solvate thereof.

In an embodiment, said compounds of formula (I), (Ia) or (Ib) is not Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitile; 2-Amino-5-benzythiophene-3-carbonitrile; 2-Amino-5-isopropylthiophene-3-carbonitrile; 2-Amino-5-(tert-butyl)thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl) thiophene-3-carboxamide; 2-Amino-3-cyano-5-[2-(2',5'-dimethoxyphenyl)ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile.

One embodiment of the present invention concerns the compounds of formula I, wherein said group A can be any lipophilic moiety as these moieties are well known to the skilled person, including optionally substituted aryl heteroaryl cycloalkyl groups and the like.

One embodiment of the present invention concerns the compounds of formula I, wherein said group A is $C_{1-7}$ alkyl, $C_{2-7}$ alkenyl, $C_{2-7}$ alkynyl, halo $C_{1-7}$ alkyl, $C_{3-10}$ cycloalkyl or heterocyclic-substituted alkyl. In another embodiment said group A is $C_{1-7}$ alkyl. In another embodiment said group A is $C_{2-7}$ alkenyl. In another embodiment said group A is $C_{2-7}$ alkynyl. In another embodiment said group A is halo $C_{1-7}$ alkyl. In another embodiment said group A is $C_{3-10}$ cycloalkyl. In another embodiment said group A is heterocyclic-substituted alkyl.

One embodiment of the present invention concerns the compounds of formula I, wherein said group A is thio $C_{1-7}$ alkyl, thio $C_{3-10}$ cycloalkyl, arylthio or arylalkylthio. In another embodiment said group A is thio $C_{1-7}$ alkyl. In another embodiment said group A is thio $C_{3-10}$ cycloalkyl. In another embodiment said group A is arylthio. In another embodiment said group A is arylalkylthio.

One embodiment of the present invention concerns the compounds of formula I, wherein said group A is phenyl, thiophene, cyclohexyl or cyclohexenyl. One embodiment of the present invention concerns the compounds of formula I, wherein said group A is phenyl, naphthlyl, biphenylyl, thiophene, cyclohexyl or cyclohexenyl. In another embodiment said group A is phenyl. In another embodiment said group A is cyclohexenyl. In another embodiment said group A is cyclohexyl. In another embodiment said group A is a thiophene. In another embodiment, said group A is an aryl group optionally substituted with 1 or 2 substituents selected from the group consisting of a methoxy group and a methyl group. In another embodiment, said group A is an aryl group substituted with 1 or 2 substituents selected from the group consisting of a methoxy group and a methyl group; and in a further more specified embodiment said substituent is a methoxy group; and in an even more specified embodiment said methoxy group is on the $R^5$ or $R^3$ position of said aryl or phenyl ring. In another embodiment said 1 or 2 substituents are on the $R^5$ and/or $R^3$ position of said aryl or phenyl ring.

Another embodiment of the present invention concerns the compounds of this invention, including the compounds of formula I and Ia, wherein $R^1$ is independently selected from the group consisting of hydrogen; carboxy$C_{1-7}$ alkyl; cyano; —COOH; CONR$^a$R$^b$; SO$_2$R; SO$_2$NHR; SO$_2$NR$^a$R$^b$, SO$_2$OR; PO(XR)$_2$, heteroaryl and aryl groups; and $C_{3-10}$ cycloalkyl groups, wherein R, R$^a$ and R$^b$ are each independently selected from the group consisting of H, $C_{1-7}$alkyl, $C_{3-10}$ cycloalkyl and aryl.

One embodiment of the present invention concerns the compounds of this invention, including the compounds of formula I and Ia, wherein said $R^1$ is a carboxy$C_{1-7}$alkyl. One more specific embodiment of the present invention concerns the compounds of this invention, including the compounds of formula I and Ia, wherein said $R^1$ is a carboxymethyl or a carboxy-ethyl group. In another embodiment said $R^1$ is a carboxymethyl group. In another embodiment said $R^1$ is a carboxyethyl group.

One embodiment of the present invention concerns the compounds of this invention, including the compounds of formula I and Ia, wherein said $R^0$ is selected from the group consisting of hydrogen; amino; (mono- or di) $C_{1-7}$alkylamino, including —NHCH$_3$, and —N(CH$_3$)$_2$; (mono- or di) arylamino, and 1H-Isoindole-1,3(2H)-dione,2-methyl-. In a more specific embodiment said $R^0$ is amino.

One embodiment of the present invention concerns the compounds of this invention, including the compounds of formula I and Ia, wherein said $R^2$ is selected from the group consisting of hydrogen, carboxyethyl and methyl. In a more specific embodiment said $R^2$ is hydrogen.

One embodiment of the present invention concerns the compounds of this invention, including the compounds of formula I and Ia, wherein said $R^1$ is a carboxymethyl or a carboxy-ethyl group, and wherein said $R^0$ is amino. A more specific embodiment of the present invention concerns the compounds of this invention, including the compounds of formula I and Ia, wherein said $R^1$ is a carboxymethyl or a carboxy-ethyl group, and wherein said $R^0$ is amino, and wherein said $R^2$ is hydrogen.

One embodiment of the present invention concerns the compounds of this invention, including the compounds of formula I, Ia and Ib, wherein said $R^3$, $R^4$, $R^5$, $R^6$ and $R^7$ are independently selected from the group consisting of hydrogen; $C_{1-7}$alkyl; $C_{1-7}$ alkoxy; halogen; amino; (mono- or di) $C_{1-7}$ alkylamino, (mono- or di) arylamino, azido; hydroxyl; $C_{3-10}$ cycloalkyl; heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, and wherein said alkyl is optionally substituted with one or more substituents selected from the group consisting of halogen, nitro, hydroxyl, sulfhydryl, amino, azido.

One embodiment of the present invention concerns the compounds of this invention, including the compounds of formula Ia, wherein n is 2, 3, 4, 5, 6 or 7. In a more specific embodiment said n is 2 or 3. In an even more specific embodiment said n is 2.

One embodiment of the present invention concerns the compounds of this invention, including the compounds of formula I and Ib, wherein X is a spacer or a linker consisting of 1, 2, or 3, 4, 5, 6 or 7 carbon atoms. In a more specific embodiment said X is a spacer or a linker consisting of 1, 2, or 3 carbon atoms. In an even more specific embodiment said X is a spacer or a linker consisting of 2 carbon atoms. In another specific embodiment, said X is selected from the group consisting of —(CH$_2$)$_2$—, acetylene, ethylene, —SCH$_2$—, —OCH$_2$—, —NHCH$_2$— and —CH$_2$SCH$_2$—.

The present invention also encompasses a compound having the general formula I, Ia, or Ib: wherein A is selected from the group consisting of $C_{1-10}$ alkyl; $C_{2-7}$ alkenyl; $C_{2-7}$ alkynyl; halo $C_{1-7}$alkyl; $C_{3-10}$ cycloalkyl; $C_{1-7}$ alkoxy; $C_{3-10}$ cycloalkoxy; aryloxy; arylalkyloxy; oxyheterocyclic; thio $C_{1-7}$ alkyl; thio $C_{3-10}$ cycloalkyl; arylthio; arylalkylthio; heterocyclic-substituted alkyl; heterocyclic-substituted alkyloxy; heteroaryl and aryl groups, and wherein said $C_{1-10}$alkyl is optionally substituted with one or more substituents selected from the group consisting of halogen, nitro, hydroxyl, sulfhydryl, amino, azido;

wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, carboxyl, $C_{1-7}$alkyloxycarbonyl; halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, and wherein said $C_{1-7}$alkyl is optionally substituted with one or more substituents selected from the group consisting of halogen, nitro, hydroxyl, sulfhydryl, amino, azido;

$R^0$ is independently selected from the group consisting of amino; (mono- or di) $C_{1-7}$ alkylamino; (mono- or di) arylamino; azido; 1H-Isoindole-1,3(2H)-dione,2-methyl-;

$R^1$ is independently selected from the group consisting of carboxy$C_{1-7}$ alkyl; cyano; —COOH; CONR$^a$R$^b$; SO2R; SO$_2$NHR; SO$_2$NR$^a$R$^b$, SO$_2$OR; PO(XR)$_2$; and $C_{3-10}$ cycloalkyl, wherein R, R$^a$ and R$^b$ are each independently selected from the group consisting of H and $C_{1-7}$alkyl and $C_{3-10}$ cycloalkyl;

$R^2$ is independently selected from the group consisting of hydrogen; carboxy$C_{1-7}$ alkyl, $C_{1-7}$alkyl; cyano; —CONHMe; —COOH; —CONH$_2$ X is independently selected from the group consisting of —(CR$^e$R$^f$)$_n$—, —(CR$^e$R$^f$)$_m$-acetylene, -acetylene-(CR$^e$R$^f$)$_m$—, —(CR$^e$R$^f$)$_m$— ethylene, -ethylene-(CR$^e$R$^f$)$_m$—, —S(CR$^e$R$^f$)$_m$—, —(CR$^e$R$^f$)$_m$S—, —O(CR$^e$R$^f$)$_m$—, —(CR$^e$R$^f$)$_m$O—, —NH(CR$^e$R$^f$)$_m$—; —(CR$^e$R$^f$)$_m$NH—, —(CR$^e$R$^f$)$_m$S(CR$^e$R$^f$)$_p$—, —(CR$^e$R$^f$)$_m$O(CR$^e$R$^f$)$_p$, wherein m is 0, 1, 2, 3, 4, 5, 6 or 7, and wherein p is 0, 1, 2, 3, 4, 5, 6 or 7, and wherein n is 2, 3, 4, 5, 6 or 7; wherein each R$^e$ and R$^f$ is independently selected from hydrogen or C$_{1-7}$alkyl; preferably X is independently selected from the group consisting of —(CH$_2$)$_n$, —(CH$_2$)$_m$-acetylene, -acetylene-(CH$_2$)$_m$—, —(CH$_2$)$_m$-ethylene-, -ethylene-(CH$_2$)$_m$—, —S(CH$_2$)$_m$—, —(CH$_2$)$_m$S—, —O(CH$_2$)$_m$—, —(CH$_2$)$_m$O—, —NH(CH$_2$)$_m$—; —(CH$_2$)$_m$NH—, —(CH$_2$)$_m$S(CH$_2$)$_p$—, —(CH$_2$)$_m$O(CH$_2$)$_p$, wherein m is 0, 1, 2, 3, 4, 5, 6 or 7, and wherein p is 0, 1, 2, 3, 4, 5, 6 or 7, and wherein n is 2, 3, 4, 5, 6 or 7;

R$^3$, R$^4$, R$^5$, R$^6$ and R$^7$ are independently selected from the group consisting of hydrogen; C$_{1-7}$alkyl; C$_{1-7}$ alkoxy; halogen; amino; (mono- or di) C$_{1-7}$ alkylamino, (mono- or di) arylamino; azido; hydroxyl; C$_{3-10}$ cycloalkyl, and wherein said alkyl is optionally substituted with one or more substituents selected from the group consisting of halogen, nitro, hydroxyl, sulfhydryl, amino, azido;

and/or a pharmaceutical acceptable addition salt thereof and/or a stereoisomer thereof and/or a solvate thereof;

with the proviso that said compound is not Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitile; 2-Amino-5-benzythiophene-3-carbonitrile; 2-Amino-5-isopropylthiophene-3-carbonitrile; 2-Amino-5-(tert-butyl)thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl)thiophene-3-carboxamide; 2-Amino-3-cyano-5-[2-(2',5'-dimethoxyphenyl) ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile.

In some embodiments, A is C$_{1-7}$ alkyl or C$_{2-7}$ alkenyl. In some embodiments, A is phenyl or thiophene. In some embodiments, R$^1$ is carboxyC$_{1-7}$alkyl, preferably a carboxymethyl or carboxyethyl group. In some embodiments, A is an aryl group optionally substituted with 1 or 2 substituents selected from the group consisting of C$_{1-6}$alkoxy and C$_{1-6}$alkyl. In some embodiments, A is an aryl group optionally substituted with 1 or 2 substituents selected from the group consisting of a methoxy group and a methyl group. In some embodiments, X is selected from the group consisting of a —(CH$_2$)$_2$—, an ethylene and an acetylene group. In some embodiments, n is 2. In some embodiments, R$^0$ is amino. In some embodiments, R$^2$ is hydrogen.

The present invention also encompasses a compound selected from the group consisting of: Methyl-2-amino-5-(2-(4-methoxyphenyl)ethyl)thiophene-3-carboxylate; Methyl-2-amino-5-(2-(phenylethyl)thiophene-3-carboxylate; Methyl-2-amino-5-(2-(2-methoxyphenyl)ethyl)thiophene-3-carboxylate; Methyl-2-amino-5-(2-(4-methoxy-2-methylphenyl)ethyl)thiophene-3-carboxylate; Methyl-2-amino-5-(2-(2-thienyl)ethyl)thiophene-3-carboxylate; Ethyl-2-amino-5-(2-(4-methoxyphenyl)ethynyl)thiophene-3-carboxylate; Ethyl-2-amino-5-(2-(4-methoxyphenyl)ethyl)thiophene-3-carboxylate; Ethyl-2-amino-5-(4-methoxyphenyl)thiophene-3-carboxylate; Ethyl-2-amino-5-(2-methoxyphenyl)thiophene-3-carboxylate; Ethyl-2-amino-5-(2-(2-methoxyphenyl)ethyl)thiophene-3-carboxylate; Ethyl-2-amino-4-ethoxycarbonyl 5-(2-(4-methoxyphenyl)ethyl)thiophene-3-carboxylate; Methyl-2-amino-5-(4-methoxyphenyl)thiophene-3-carboxylate; Methyl-2-amino-5-((2-methoxyphenyl)thiophene-3-carboxylate; 2-Amino-3-cyano-5-(4-methoxyphenyl) thiophene; Methyl-2-amino-5-(2,5-dimethoxyphenyl)thiophene-3-carboxylate; 2-Amino-3-cyano-5-(2-(2-methoxyphenyl)ethyl)thiophene; 2-Amino-3-cyano-5-(2-(4-methoxyphenyl)ethyl)thiophene; Ethyl-2-amino-5-(2-(2,5-dimethoxyphenyl)ethyl)thiophene-3-carboxylate; 2-Amino-3-cyano-5-(2-(phenyl)ethyl)thiophene; 2-Amino-3-cyano-5-(2-(2,5-dimethoxyphenyl)ethyl)thiophene; Ethyl-2-amino-4-ethoxycarbonyl-5-(2-(2,5-dimethoxymethoxyphenyl) ethyl)thiophene-3-carboxylate; Methyl-2-amino-5-(2-(2-pyridyl)ethyl)thiophene-3-carboxylate; Methyl-2-amino-5-(2-(3-pyridyl)ethyl)thiophene-3-carboxylate; Methyl-2-amino-4-methyl-5-(2-(2,5-dimethoxyphenyl)ethyl) thiophene-3-carboxylate; Methyl-2-amino-5-(2,5-dimethoxyphenyl)thiophene-3-carboxylate; N-Methyl-2-amino-5-(2-(4-methoxyphenyl)ethyl)thiophene-3-carboxamide; 2-Amino-5-(2-(4-methoxyphenyl)ethyl) thiophene-3-carboxylate; 2-Amino-5-(2-(4-methoxyphenyl) ethyl)thiophene-3-carboxamide; Methyl-2-methylamino-5-(2-(4-methoxyphenyl)ethyl)thiophene-3-carboxylate; Methyl-2-dimethylamino-5-(2-(4-methoxyphenyl)ethyl) thiophene-3-carboxylate; Methyl-5-(2-(4-methoxyphenyl) ethyl)thiophene-3-carboxylate; Methyl-2-amino-5-(2-(4-methoxyphenyl)sulfanylmethyl)thiophene-3-carboxylate; Methyl-2-amino-5-(2-(4-methoxyphenyl)oxymethyl) thiophene-3-carboxylate; Methyl-2-amino-5-(2-(4-methoxyphenyl)aminomethyl)thiophene-3-carboxylate; Methyl-2-amino-5-(2-(4-methylphenyl)sulfanylmethyl)thiophene-3-carboxylate; Methyl-2-amino-5-(2-(3-methylphenyl) sulfanylmethyl)thiophene-3-carboxylate; Methyl-2-amino-5-(2-(phenyl)methylsulfanylmethyl)thiophene-3-carboxylate; Methyl-2-amino-5-(2-(phenyl)sulfanylmethyl) thiophene-3-carboxylate; Methyl-2-phthalimido-5-(2-(4-methoxyphenyl)sulfanylmethyl)thiophene-3-carboxylate; and Methyl-2-phthalimido-5-(2-(3-methylphenyl)sulfanylmethyl)thiophene-3-carboxylate; methyl 2-amino-5-propyl-thiophene-3-carboxylate; methyl 2-amino-5-(3-chloropropyl)thiophene-3-carboxylate; methyl 2-amino-5-butyl-thiophene-3-carboxylate; methyl 2-amino-5-pentyl-thiophene-3-carboxylate; methyl 2-amino-5-hexyl-thiophene-3-carboxylate; methyl 2-amino-5-heptyl-thiophene-3-carboxylate; methyl 2-amino-5-octyl-thiophene-3-carboxylate; methyl 2-amino-5-(1,5-dimethylhex-4-enyl)thiophene-3-carboxylate; 2-amino-5-non-8-enyl-thiophene-3-carbonitrile; methyl 2-amino-4-methyl-5-octyl-thiophene-3-carboxylate; methyl 2-amino-5-nonyl-thiophene-3-carboxylate; methyl 2-amino-5-decylthiophene-3-carboxylate; methyl 2-amino-5-dodecylthiophene-3-carboxylate; methyl 2-amino-5-tridecylthiophene-3-carboxylate; methyl 2-amino-5-tetradecylthiophene-3-carboxylate; methyl 2-amino-5-pentadecylthiophene-3-carboxylate; methyl 2-amino-5-hexadecylthiophene-3-carboxylate; methyl 2-amino-5-(butylthiomethyl)thiophene-3-carboxylate; methyl 2-amino-5-(pentylthiomethyl)thiophene-3-carboxylate; methyl 2-amino-5-(isopentylthiomethyl)thiophene-3-carboxylate; methyl 2-amino-5-(hexylthiomethyl)thiophene-3-carboxylate; methyl 2-amino-5-(heptylthiomethyl)thiophene-3-carboxylate; methyl 2-amino-5-(octylthiomethyl)thiophene-3-carboxylate; methyl 2-amino-5-(cyclopentylthiomethyl)thiophene-3-carboxylate; methyl 2-amino-5-(cyclohexylthiomethyl)thiophene-3-carboxylate; methyl 2-amino-5-(phenylthiomethyl)thiophene-3-carboxylate; methyl 2-amino-5-(p-tolylthiomethyl)thiophene-3-carboxylate; methyl 2-amino-5-(o-tolylthiomethyl)thiophene-3-carboxylate; methyl 2-amino-5-(m-tolylthiomethyl)thiophene-3-carboxylate; methyl 2-amino-5-[(2-aminophenyl)thiomethyl]thiophene-3-carboxylate; methyl 2-amino-5-[(4-methoxyphenyl)thiomethyl]thiophene-3-carboxylate; methyl 2-amino-5-[(2-methoxyphenyl)thiomethyl]thiophene-3-carboxylate; methyl 2-amino-5-[(2-methoxycarbonylphenyl)thiomethyl]thiophene-3-carboxylate; 3-((5-amino-4-(methoxycarbonyl)thiophen-2-yl)methylthio)benzoic acid; methyl 2-amino-5-[(4-fluorophenyl)thiomethyl]thiophene-3-carboxylate; methyl 2-amino-5-[(4-chlorophenyl)thiomethyl]thiophene-3-carboxylate; methyl 2-amino-5-[(4-nitrophenyl)thiomethyl]thiophene-3-carboxylate; methyl 2-amino-5-[(4-ethylphenyl)thiomethyl]thiophene-3-carboxylate; methyl 2-amino-5-[(4-isopropylphenyl)thiomethyl]thiophene-3-carboxylate; methyl 2-amino-5-[(4-methoxyphenyl)methylthiomethyl]thiophene-3-carboxylate; methyl 2-amino-5-[(phenyl)methylthiomethyl]thiophene-3-carboxylate; methyl 2-amino-5-(phenethylthiomethyl)thiophene-3-carboxylate; methyl 2-amino-5-[(biphenyl-4-yl)thiomethyl]thiophene-3-carboxylate; methyl 2-amino-5-(2-naphthylthiomethyl)thiophene-3-carboxylate; methyl 2-amino-5-(4-pyridylthiomethyl)thiophene-3-carboxylate; methyl 2-amino-5-(2-thienylmethylthiomethyl)thiophene-3-carboxylate; methyl 2-amino-5-(2-furylmethylthiomethyl)thiophene-3-carboxylate; methyl 2-amino-5-(3-cyclohexylthiopropyl)thiophene-3-carboxylate; methyl 2-amino-5-[3-(4-methoxyphenyl)thiopropyl]thiophene-3-carboxylate.

The present invention also concerns the compounds of the present invention, including the compounds of formula I, Ia, and Ib, for use as a medicine.

One aspect of this invention relates to the compounds of this invention and their use as a medicament for the treatment of cancer, including lymphoma, hepatoma and prostate cancer.

In certain embodiments of this invention, the compounds of this invention are used as a medicament for the treatment or prevention of lymphomas. In certain more specific embodiments of the present invention, said lymphoma is a T-cell lymphoma.

In certain embodiments of this invention, the compounds of this invention are used as a medicament for the treatment or prevention of hepatomas or liver cancer.

One aspect of the disclosure relates to treatment or prevention of prostate disease. In some embodiments, the compounds of this invention are used as a medicament for treatment or prevention of abnormal prostatic growths in a subject. The growths may be benign, such as benign prostatic hyperplasia, or may be associated with prostate cancer, for example, as an early or precursor stage of prostate cancer. One exemplary condition associated with development of prostate cancer is prostatic intraepithelial neoplasia.

In certain embodiments, the compounds of formula (I) are used as a medicament for treatment or prevention of prostate cancer. In certain embodiments, the prostate cancer is a metastatic and/or aggressive form of prostate cancer. In some embodiments, the prostate cancer is adenocarcinoma. Adenocarcinoma is the most common form of prostate cancer, and is typically characterized by its origin in the peripheral zone (main glandular zone) of the prostate, and its development from epithelial cells. In further embodiments, the prostate cancer is a basal cell carcinoma, small cell carcinoma, squamous cell carcinoma, sarcoma, transitional cell carcinoma, or any combination of these. In addition, the prostate cancer may have developed from primary tumors that arose in other locations such as the bladder or urethra, and spread to the prostate.

In some embodiments, the prostate cancer is in stage T1 or T2, according to the four-stage Tumor/Nodes/Metastasis (TNM) system. In certain embodiments, the prostate cancer may have spread outside of the prostate, and may be a stage T3 or T4 cancer. For example, a prostate cancer may have spread to the lymph nodes, bladder, urethra, rectum, bones, or other organs. In some embodiments, the medicaments described herein may prevent and/or slow a prostate cancer's progression to the next stage.

In some embodiments, the prostate cancer has taken a form that does not respond to treatment and/or has become refractory. Often, prostate cancer is treated by administering compounds that disrupt the androgen signaling pathways essential for growth and survival of prostate cancer cells. For example, androgen receptor (AR) antagonists, also called anti-androgens, are administered in order to block binding of testosterone (T) and dihydrotestosterone (DHT) to the AR on prostate cancer cells. Initially, treatment with AR antagonists can prove successful in reducing the growth of prostate cancer cells. However, the prostate cancer can become refractive, and resume growth in spite of the treatment. When this occurs, the prostate cancer is known as a castration-resistant prostate cancer. This form of prostate cancer has also been previously termed "hormone refractory prostate cancer" and "androgen-independent prostate cancer." Castration-resistant prostate cancer may emerge at any time after initiating treatment of prostate cancer. In some embodiments, the castration-resistant prostate cancer emerges within at least 3, 4, 5, 6, 7, 8, 9, 10, or 11 months of treatment, or may emerge within 12, 13, 14, 15, 16, 17, 18, 19, 20, 21, 22 months, or within 2, 3, 4, or 5 years of treatment.

Thus, in certain embodiments, the compounds of formula I and/or formula Ia and/or Ib are used as a medicament for treatment or prevention of castration-resistant prostate cancer. In some embodiments, the castration-resistant prostate cancer was previously treated with at least one AR antagonist, for example, at least one steroidal and/or at least one nonsteroidal AR antagonist. Exemplary nonsteroidal AR antagonists include but are not limited to Bicalutamide (Bic), Hydroxyflutamide (HOFl), Nilutamide, MDV3100, or its variant RD-162, and ARN-509. Accordingly, the prostate cancer may no longer respond to the dosages of an AR antagonist such as Bic, HOFl, Nilutamide, MDV3100, RD-162 and/or ARN-509 that had been therapeutically effective in the past.

The present invention also concerns a pharmaceutical composition comprising a therapeutically effective amount of a compound of the present invention, including a compound of formula I, Ia or Ib, and one or more pharmaceutically acceptable excipients for use as a medicine for the prevention or treatment of a proliferative disorder such as cancer in an animal, mammal or human. Said composition may further comprise one or more biologically active drugs being selected from the group consisting of antineoplastic drugs and/or immunosuppressant and/or immunomodulator drugs.

The present invention also concerns a method of prevention or treatment of proliferative disorder, including cancer such as hematological malignancies, including acute leukemia, chronic leukemia (myeloid or lymphoid), lymphoma (Hodgkin's or non-Hodgkin's), multiple myeloma, myelodysplastic syndrome, or non-hematological cancers such as prostate carcinoma or liver carcinoma, in an animal, comprising the administration of a therapeutically effective amount of a compound of the present invention, including a compound of formula I, Ia or Ib, optionally in combination with one or more pharmaceutically acceptable excipients.

The present invention also encompasses processes for the preparation of compounds of Formula I, Ia, and Ib. In a certain embodiment of the present invention said process for preparation of the compounds of formula I, Ia or Ib comprises the steps of:
(a) a Gewald reaction of an enolizable compound (aldehyde or ketone), sulfur and an active methylene containing a cyano group
(b) protection of the 5-amino group as phthalimide and further transformations at the 2-position of the thiophene starting from bromo or 2-bromomethyl derivatives; thus introducing the aromatic, heterocyclic or lipophilic side chain and
(c) deprotection of the phthalimide function by hydrazine or methylhydrazine to liberate the 5-aminothiophene.

DEFINITIONS

When describing the compounds of the invention, the terms used are to be construed in accordance with the following definitions, unless a context dictates otherwise.

As used herein with respect to a substituting radical, and unless otherwise stated, the term "$C_{1-7}$ alkyl" means straight and branched chain saturated acyclic hydrocarbon monovalent radicals having from 1 to 7 carbon atoms such as, for example, methyl, ethyl, propyl, n-butyl, 1-methylethyl (isopropyl), 2-methylpropyl (isobutyl), 1,1-dimethylethyl (ter-butyl), 2-methylbutyl, n-pentyl, dimethylpropyl, n-hexyl, 2-methylpentyl, 3-methylpentyl, n-heptyl and the like. When a subscript is used herein following a carbon atom, the subscript refers to the number of carbon atoms that the named group may contain. Thus, for example, $C_{1-6}$alkyl groups include all linear, or branched alkyl groups having 1 to 6 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers.

As used herein with respect to a substituting radical, and unless otherwise stated, the term "$C_{1-7}$ alkylene" means the divalent hydrocarbon radical corresponding to the above defined $C_{1-7}$ alkyl, such as methylene, bis(methylene), tris(methylene), tetramethylene, hexamethylene and the like.

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "aryl" designate any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_4$-$\beta$ cycloalkyl radicals (the latter being as defined above) such as, for instance, indanyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting radical (including the combination of substituents in certain positions of the compounds of formula I, Ia, Ib, or group A), and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepine, benzodioxepinyl, benzodithiepinyl, berrzoxazocinyl, benzo-thiazocinyl, benzodiazocinyl, benzoxathiocinyl, benzodioxocinyl, benzotrioxepinyl, benzoxathiazepinyl, benzoxadiazepinyl, benzothia-diazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzo-carbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphtindazolyl, naphtindolyl, naphtothiazolyl, naphtothioxolyl, naphtoxindolyl, naphto-triazolyl, naphtopyranyl, oxabicycloheptyl, azabenzimidazolyl, azacycloheptyl, azacyclooctyl, azacyclononyl, azabicyclononyl, tetrahydrofuryl, tetrahydropyrarryl, tetrahydro-pyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofutyl, furoyl, hydantoinyl, dioxolanyl, dioxolyl, dithianyl, dithienyl, dithiinyl, thienyl, indolyl, indazolyl, benzofutyl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, pheno-metoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsulfinyl, benzylsulfanyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkyl-amino, hydroxylalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, tricarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituting radical, and unless otherwise stated, the terms "$C_{1-7}$ alkoxy", "$C_{3-10}$ cycloalkoxy", "aryloxy", "arylalkyloxy", "oxyheterocyclic", "thio $C_{1-7}$ alkyl", "thio $C_{3-10}$ cycloalkyl", "arylthio", "arylalkylthio" and "thioheterocyclic" refer to substituents wherein a carbon atom of a $C_{1-7}$ alkyl, respectively a $C_{3-10}$ cycloalkyl, aryl, arylalkyl or heterocyclic radical (each of them such as defined herein), is attached to an oxygen atom or a divalent sulfur atom through a single bond such as, but not limited to, methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl, cresoxy, and the like.

As used herein with respect to a substituting atom, and unless otherwise stated, the term "halogen" or "halo" means any atom selected from the group consisting of fluorine, chlorine, bromine and iodine.

As used herein with respect to a substituting radical, and unless otherwise stated, the term "halo $C_{1-7}$ alkyl" means a $C_{1-7}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl and the like.

As used herein with respect to a substituting radical, and unless otherwise stated, the terms "$C_{2-7}$ alkenyl" designate a straight and branched acyclic hydrocarbon monovalent radical having one or more ethylenic unsaturations and having from 2 to 7 carbon atoms such as, for example, vinyl, 1-propenyl, 2-propenyl (allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein with respect to a substituting radical, and unless otherwise stated, the term "$C_{2-7}$ alkynyl" defines straight and branched chain hydrocarbon radicals containing one or more triple bonds and optionally at least one double bond and having from 2 to 7 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein with respect to a substituting radical, and unless otherwise stated, the terms "arylalkyl", "arylalkenyl" and "heterocyclic-substituted alkyl" refer to an aliphatic saturated or ethylenically unsaturated hydrocarbon monovalent radical (preferably a $C_{1-7}$ alkyl or $C_{2-7}$ alkenyl radical such as defined above) onto which an aryl or heterocyclic radical (such as defined above) is already bonded via a carbon atom, and wherein the said aliphatic radical and/or the said aryl or heterocyclic radical may be optionally substituted with one or more substituents independently selected from the group consisting of halogen, amino, hydroxyl, sulfhydryl, $C_{1-7}$ alkyl, $C_{1-7}$ alkoxy, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl]ethyl, 1-amino-2-[indol-2-yl]ethyl, styryl, pyridylmethyl (including all isomers thereof), pyridylethyl, 2-(2-pyridyl)isopropyl, oxazolylbutyl, 2-thienylmethyl, pyrrolylethyl, morpholinylethyl, imidazol-1-yl-ethyl, benzodioxolylmethyl and 2-furylmethyl.

As used herein with respect to a substituting radical, and unless otherwise stated, the term "carboxyC$_{1-7}$ alkyl" refers to a group of formula —C(=O)—O—R$^d$, wherein R$^d$ is C$_{1-7}$ alkyl such as defined above. As used herein with respect to a substituting radical, and unless otherwise stated, the term "carboxymethyl" refers to —C(=O)—O—CH$_3$. As used herein with respect to a substituting radical, and unless otherwise stated, the term "carboxyethyl" refers to —C(=O)—O—CH$_2$—CH$_3$.

As used herein with respect to a substituting radical, and unless otherwise stated, the term "ethylene" refers to the group —CH=CH—.

As used herein with respect to a substituting radical, and unless otherwise stated, the term "—(CH$_2$)$_m$-ethylene" refers to the group of formula —(CH$_2$)$_m$—CH=CH—, wherein m has the same meaning as that defined herein.

As used herein with respect to a substituting radical, and unless otherwise stated, the term "-ethylene-(CH$_2$)$_m$—" refers to the group of formula —CH=CH—(CH$_2$)$_m$—, wherein m has the same meaning as that defined herein.

As used herein with respect to a substituting radical, and unless otherwise stated, the term "acetylene" refers to the group —C≡C—.

As used herein with respect to a substituting radical, and unless otherwise stated, the term "—(CH$_2$)$_m$-acetylene" refers to the group of formula —(CH$_2$)$_m$—C≡C—, wherein m has the same meaning as that defined herein.

As used herein with respect to a substituting radical, and unless otherwise stated, the term "-acetylene-(CH$_2$)$_m$—" refers to the group of formula —C≡C—(CH$_2$)$_m$—, wherein m has the same meaning as that defined herein.

"Lymphoma" is a cancer of the lymphocytes. Typically, lymphoma is present as a solid tumor of lymphoid cells. The malignant cells often originate in lymph nodes, presenting as an enlargement of the node (a tumor). It can also affect other organs, in which case it is referred to as extranodal lymphoma. Extranodal sites include the skin, brain, bowels and bone. Lymphomas are closely related to lymphoid leukemias, which are also contemplated by the cancers to be prevented or treated by pharmaceutical compositions of this invention or these lymphoid leukemias also originate in lymphocytes but typically involve only circulating blood and the bone marrow and do not usually form static tumors. There are many types of lymphomas, and in turn, lymphomas are a part of the broad group of diseases called hematological neoplasms. Lymphomas can be divided in four broad groups: mature B-cell neoplasms, mature T-cell and natural killer cell neoplasms, Hodgkin lymphoma, and immunodeficiency-associated lymphoproliferative disorders. Lymphomas include but are not limited to T-cell lymphomas and B-Cell lymphomas.

"T-cell lymphoma" is a disease in which cells in the lymphoid system called T cells (or T lymphocytes) become malignant. They can be associated with Epstein Barr virus and human T-cell leukemia virus-1. The T-cell proliferative disease can be peripheral T-cell lymphoma, (precursor T-cell) lymphoblastic lymphoma, cutaneous T-cell lymphoma, extranodal natural killer T-cell lymphoma, adult T-cell leukemia/lymphoma, T-cell acute lymphoblastic leukemia (T-ALL), T-cell chronic lymphoblastic leukemia (T-CLL), anaplastic large cell lymphoma, angioimmunoblastic T-cell lymphoma, enteropathy-type T-cell lymphoma, hepatosplenic T-cell lymphoma, mycosis fungoides or cutaneous T-cell lymphoma (CTCL), Sezary syndrome (the leukemic phase of CTCL), or subcutaneous panniculitis-like T-cell lymphoma.

"Hepatoma" or "liver cancer" can occur in many forms, although many cancers found in the liver are metastases from other tumors, frequently of the GI tract (like colon cancer, carcinoid tumors mainly of the appendix, etc.), but also from breast cancer, ovarian cancer, lung cancer, renal cancer, prostate cancer, etc. Liver cancers include but are not limited to the following examples. Hepatocellular carcinoma (HCC, also called malignant hepatoma) is the most common type of liver cancer. Most cases of HCC are secondary to either a viral hepatitis infection (hepatitis B or C) or cirrhosis. This tumor also has a variant type that consists of both HCC and cholangiocarcinoma components. Cancers which arise from the blood vessel cells in the liver are known as hemangioendotheliomas. As well as mixed tumors, rarer forms of liver cancer include: mesenchymal tissue; sarcoma; hepatoblastoma (a rare malignant tumor, primarily developing in children); cholangiocarcinoma (bile duct cancers); angiosarcoma and hemangiosarcoma; and lymphoma of liver.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, and/or materials and combinations thereof, as would be known to one of ordinary skill in the art. Except insofar as any conventional carrier is incompatible with the active ingredient, its use in the therapeutic or pharmaceutical composition is contemplated.

As used herein, "treating" or "treat" includes (i) preventing a pathologic condition from occurring (e.g. prophylaxis); (ii) inhibiting the pathologic condition or arresting its development; (iii) relieving the pathologic condition; and/or diminishing symptoms associated with the pathologic condition.

EXAMPLES

Example 1

Experimental Procedures

Radiochemicals.

The radiolabeled precursors [$^3$H-methyl]dThd (49 Ci/mmol), [5-$^3$H]Urd (27 Ci/mmol) and [4,5-$^3$H]leu (140 Ci/mmol) were obtained from Moravek Biochemicals (Brea, Calif.).

Cytostatic Assays.

To each well of a 96-well microtiter plate were added 5-7.5×10$^4$ cells and a given amount of the test compound. The cells were allowed to proliferate for 48 h to 96 h (depending on the nature of the cell line) at 37° C. in a humidified CO$_2$-controlled atmosphere. At the end of the incubation period, the cells were counted in a Coulter Counter (Coulter Electronics Ltd, Harpenden Herts, United Kingdom). The IC$_{50}$ (50% inhibitory concentration) was defined as the concentration of compound that reduced the number of viable cells by 50%.

Flow Cytometric Analysis of the Cell Cycle.

CEM cells were seeded at 25,000 cells/cm$^2$ in DMEM with 10% FBS in the presence of different concentrations of TR560 (100-10-1 µM) were added. At different time points, the DNA of the cells was stained with propidium iodide (PI) using the CycleTEST PLUS DNA Reagent Kit (BD Biosciences, San Jose, Calif.). Within 3 h after staining, the DNA content of the cells was measured by flow cytometry on a FACSCalibur flow cytometer and analyzed with the CellQuest software (BD Biosciences). Cell debris and clumps were excluded from the analysis by appropriate dot plot gating. Percentages of sub-G1, G1, S, and G2/M cells were quantified using appropriate region markers.

Fluorescence Detection of Caspase-3 Activity in Live Cells.

The sequence DEVD is cleaved by caspase-3 during cell death by apoptosis. NucViewTM 488-DEVD is a cell membrane-permeable fluorogenic caspase substrate designed for detecting caspase-3 activity within live cells in real time. This probe is a non-fluorescent substrate until it is cleaved by caspase-3 and allows the real-time imaging of caspase-3 activity in the nucleus of living cells. PC-3M, HeLa, U87 or CEM cells were seeded in µ-angiogenesis slides (IBIDI, München, Germany) at 50,000 cells/cm$^2$ in DMEM with 10% FBS. After 24 h, cells were incubated in DMEM containing 1 µg/ml of Hoechst 33342 (30 min at 37° C.) to stain the nucleic acids (blue). Next, the cells were washed and incubated in Hank's Buffered Salt Solution (HBSS) supplemented with 10% FBS and 10 mM HEPES (Invitrogen) containing different concentrations of compound 3 and 2 µM of the caspase-3 substrate NucViewTM 488-DEVD (Biotium, Hayward, Calif.). This substrate is non-fluorescent until it is cleaved by caspase-3 to release its dye, which stains the nucleus with bright green fluorescence. Real-time imaging of caspase-3 activity in the nucleus of living cells was performed every 30 min using a Carl Zeiss Axiovert 200 M inverted microscope (Zeiss, Göttingen, Germany) and a 20× objective.

Antimetabolic Activity Assays.

Radiolabeled precursors of DNA synthesis ([$^3$H-methyl] dThd), RNA synthesis ([5-$^3$H]Urd), and protein synthesis ([4,5-$^3$H]leu) were added to 10$^5$ CEM cell cultures in the 200 µl-wells of a microtiter plate at 1 µCi for each precursor in the presence of varying concentrations of the test compounds (5-fold dilution series). The cells were allowed to proliferate for 20 hrs at 37° C. in a humidified, CO$_2$-controlled atmosphere. At the end of the incubation period, the contents of the wells were brought onto 25-mm glass fiber filters and further processed for measurement of acid-insoluble radioactivity.

Example 2

Chemical Synthesis of Compounds of this Invention

Synthesis of Compounds of Formula (Ia) Wherein R$^2$ is Hydrogen, R$^0$ is Amino- and n is 2 is Shown in Scheme 1.

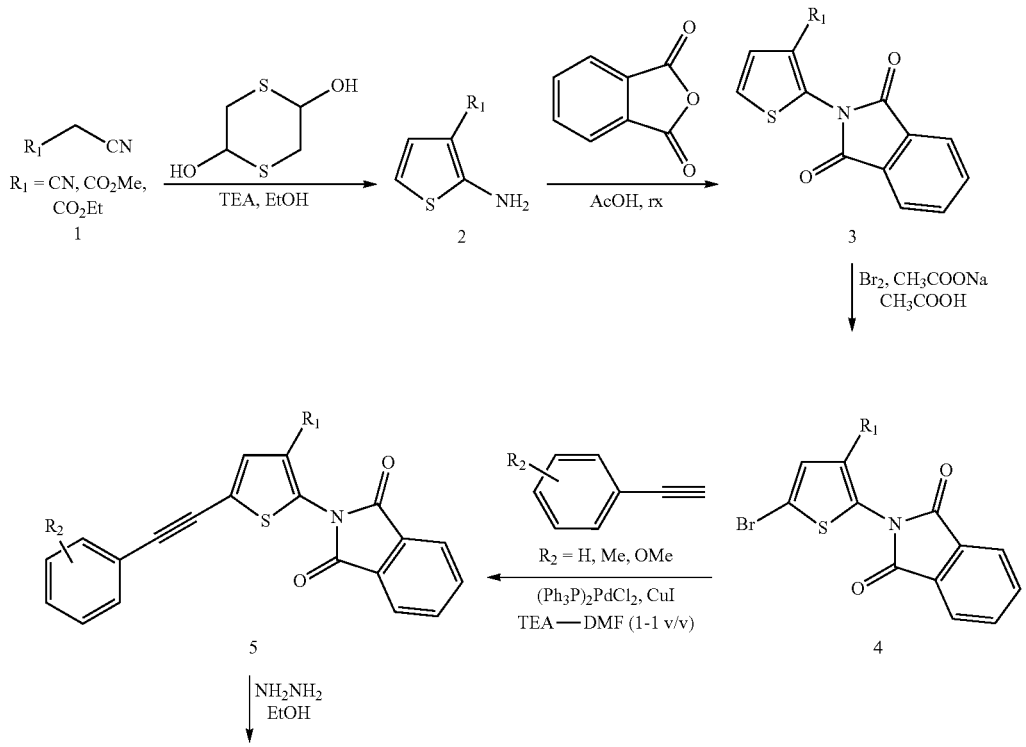

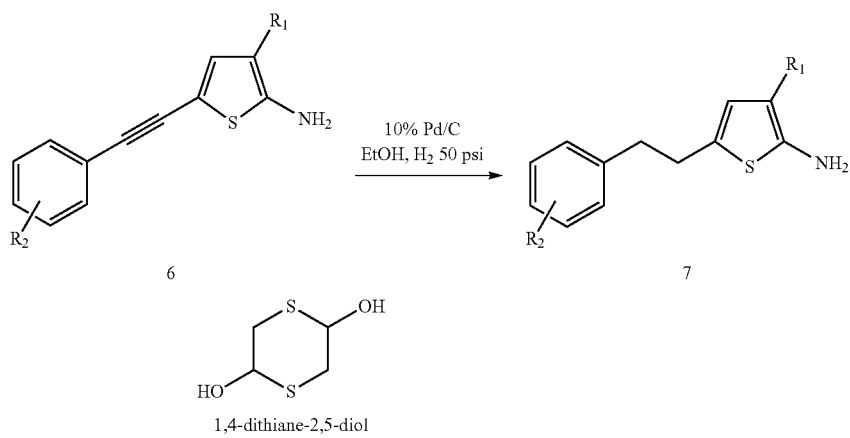

2-Amino-3-substituted-thiophene derivatives with general structure 7 were synthesized as shown in the reaction sequence reported in Scheme 1. 2-Amino-3-substituted thiophenes with general formula 2 were obtained by a one-step procedure (Gewald reaction, Huang Y and Dömling A., 2011 (2)) applied to malonitrile, methyl 2-cyanoacetate or ethyl 2-cyanoacetate 1 with the dimer of 2-mercaptoacetaldehyde (1,4-dithiane-2,5-diol) and triethylamine (TEA) as base in refluxing ethanol. The 5-unsubstituted thiophene derivative 2 was transformed almost quantitatively into the corresponding N-phthalimido derivative 3 using phthalic anhydride in refluxing acetic acid. The subsequent regioselective bromination of 3 in a mixture of acetic acid and sodium acetate, using a stoichiometric amount of bromine, furnished the intermediate 5-bromothiophene derivative with general structure 4 in good yield. This latter compound was coupled by a standard Sonogashira cross-coupling reaction with the appropriate alkyne in the presence of cuprous iodide (CuI), bis(triphenylphosphine)-palladium chloride [$PdCl_2(PPh_3)_2$] and a mixture of TEA and DMF, to afford the arylacetylenic derivative 5. Compounds with general formula 6, characterized by the presence of a flexible ethyl linker, were prepared starting from derivatives 5, by catalytic hydrogenation of the triple bond over 10% palladium on charcoal (Pd/C). Removal of the N-protected phthaloyl group was accomplished by the use of hydrazine in refluxing ethanol, to afford the final compounds with general structure 7.

Synthesis of Further Compounds of the Present Invention, Including Compounds of Formula (Ib) (Scheme 2, 3, and 4)

(Ib)

We modified the free amino group and the ester group of the derivative 7 in Scheme 2 (compound 3 in Table 1a) to study the effect of these functional groups on the antiproliferative activity (Scheme 2). The methylation of the 2-aminothiophene derivative 7 was carried out by using MeI in presence of NaH as base. The use of one equivalent of MeI resulted in N-methyl-2-aminothiophene derivative 8 (compound 28 in Table 1a) whereas as an excess of MeI resulted in N,N-dimethylated derivative 9 (compound 29 in Table 1a). The free carboxylic acid derivative 10 (compound 26 in Table 1a) was synthesized by the hydrolysis of derivative 7 using 1N solution of NaOH as base in refluxing methanol followed by acidification. The 2-unsubstituted thiophene derivative 11 (compound 30 in Table 1a) was obtained by the reduction of the diazonium salt of derivative 7 at the expense of $H_3PO_2$ as the reducing agent.

Scheme 2: Synthetic route to 2-aminothiophene derivatives analogous to 7.

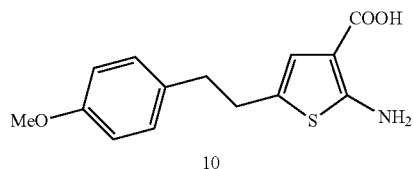

10

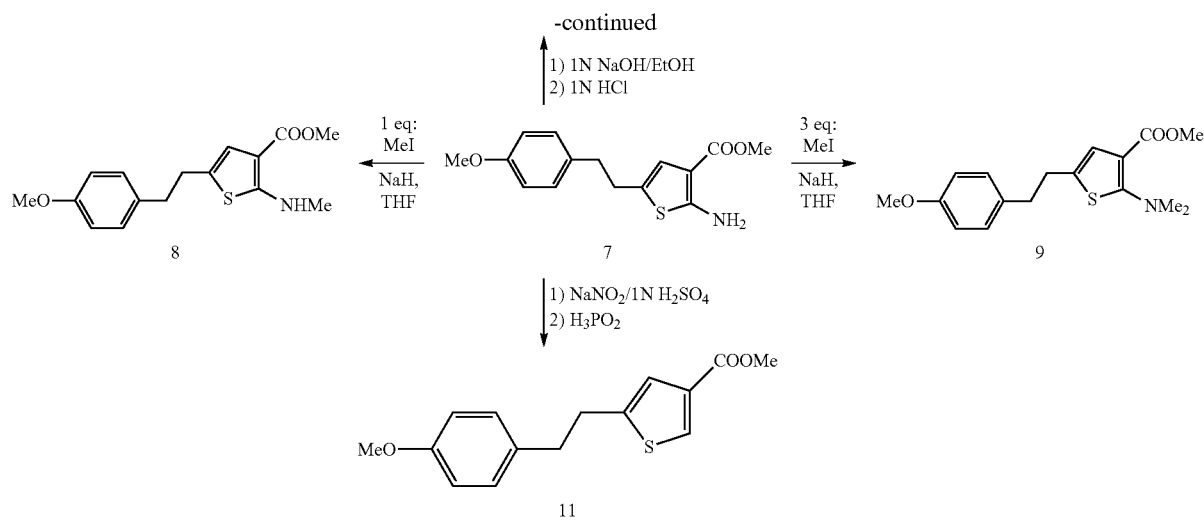

Gewald multicomponent reaction between the aldehyde 12 and the elemental sulfur with cyanoacetamide 13 or N-methylcyanoacetamide 14 using NEt₃ as base resulted in the corresponding 2-amino thiophene-3-amide derivative 15 (compound 27 in Table 1a) or derivative 16 (compound 25 in Table 1a) in reasonable yield (Scheme 3).

Scheme 3. Synthetic route to derivative 15 and 16.

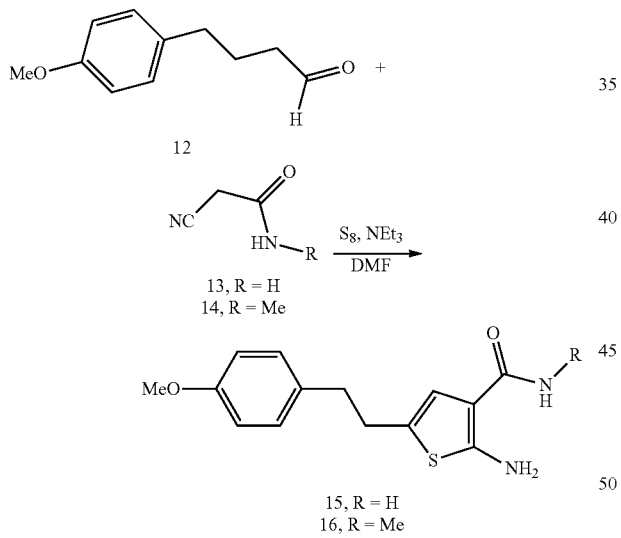

2-Aminothiophene-3-carboxylic acid ester derivatives having a thiomethyl (—SCH₂), oxymethyl (—OCH₂—), aminomethyl (—NHCH₂—) or methylthiomethyl (—CH₂SCH₂—) group directly linked at the C-5 position of the thiophene ring instead of an ethylene bridge were synthesized as shown in the reaction sequence reported in Scheme 4. The classical Gewald reaction between propionaldehyde 17 and methyl cyanoacetate 18 in the presence of sulfur and NEt₃ gives 2-amino-5-methylthiophene-3-carboxylate 19 in good yield. Subsequently, the 2-amino group of 19 was N-protected by transforming almost quantitatively into the corresponding N-phthalimido derivative 20 using phthalic anhydride in refluxing acetic acid. The bromination of the later compound with NBS yielded the corresponding bromide 21 in good yield. Further substitution reaction on to the latter compound with different nucleophiles such as benzyl mercaptan, p-methoxyphenol or p-anisidine gives the compounds having general structure 22 in reasonable to good yields.

Finally, the N-protected phthaloyl group was removed by the use of methylhydrazine in refluxing ethanol, furnishing final compounds with general structure 23.

Scheme 4. Synthetic route to compounds having general formula 23.

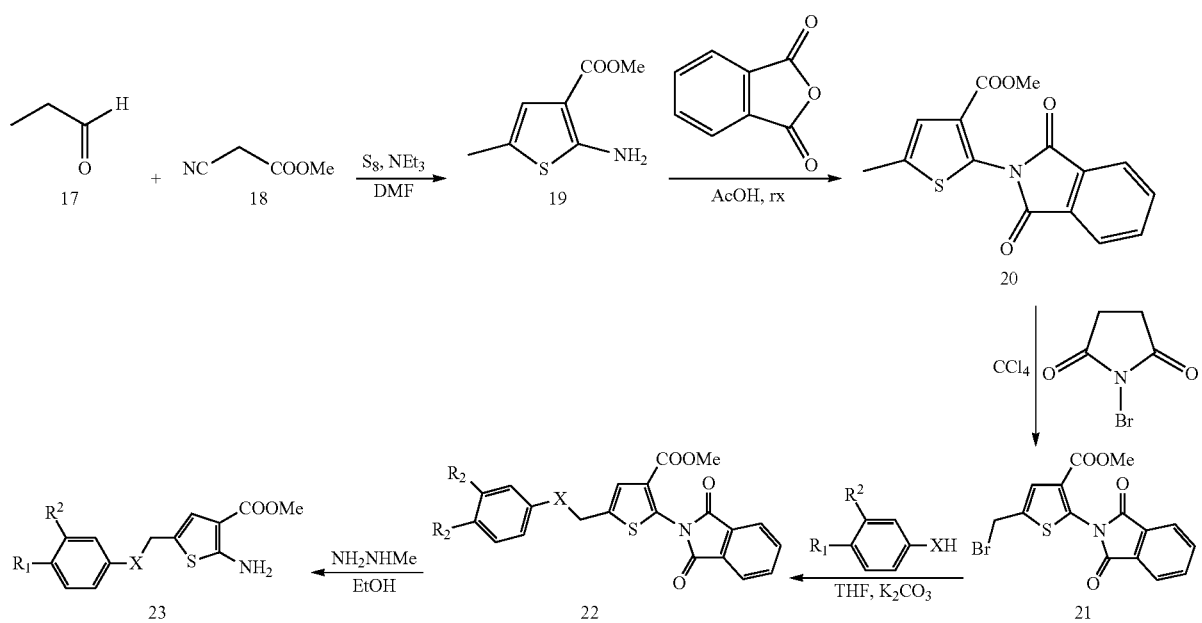

Example 3
Biological Activities

A series of 31 2-aminothiophene derivatives have been evaluated for their cytostatic activity against a broad variety of tumor cell lines in cell culture (Table 1a, Tables 2-4).

TABLE 1a

2-Amino-3-carboxylic acid ester- and 2-amino-3-cyano-thiophene derivatives (Ia)

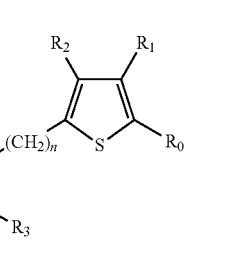

| Compound nr and code | $R_0$ | $R_1$ | $R_2$ | $R_3$ | $R_4$ | $R_5$ | $R_6$ | $R_7$ | n | $IC_{50\,\mu M}$ (CEM) |
|---|---|---|---|---|---|---|---|---|---|---|
| 3 TR560 | $NH_2$ | —COOMe | H | H | H | MeO | H | H | 2 | 0.90 |
| 1 TR575 | $NH_2$ | —COOMe | H | H | H | H | H | H | 2 | 1.5 |
| TJ109 | $NH_2$ | —COOMe | H | H | H | H | H | H | 1 | 8.4 |
| 2 TR567 | $NH_2$ | —COOMe | H | MeO | H | H | H | H | 2 | 1.8 |
| 7 TR583 | $NH_2$ | —COOMe | H | Me | H | MeO | H | H | 2 | 1.5 |
| 9 TR595[a] | $NH_2$ | —COOMe | H | — | — | — | — | — | 2 | 1.7 |
| 14 TR530 | $NH_2$ | —COOEt | H | H | H | MeO | H | H | 2[d] | 0.7 |
| 13 TR532 | $NH_2$ | —COOEt | H | H | H | MeO | H | H | 2 | 1.9 |
| 16a TR525 | $NH_2$ | —COOEt | H | H | H | MeO | H | H | 0 | 40 |
| 17 TR531 | $NH_2$ | —COOEt | H | H | H | H | H | MeO | 0 | 27 |
| 12 TR542 | $NH_2$ | —COOEt | H | MeO | H | H | H | H | 2 | 20 |
| 18 TR547 | $NH_2$ | —COOEt | —COOEt | H | H | MeO | H | H | 2 | 72 |
| 15 TR572 | $NH_2$ | —COOMe | H | H | H | MeO | H | H | 0 | 74 |
| 4 TR581 | $NH_2$ | —COOMe | H | H | H | H | H | MeO | 0 | 55 |
| 23 TR582 | $NH_2$ | —CN | H | H | H | MeO | H | H | 0 | 233 |
| 5 TR584 | $NH_2$ | —COOMe | H | MeO | H | H | MeO | H | 2 | 1.6 |
| 21 TR585 | $NH_2$ | —CN | H | MeO | H | H | H | H | 2 | 8.3 |
| 22 TR586 | $NH_2$ | —CN | H | H | H | MeO | H | H | 2 | 16 |

TABLE 1a-continued

2-Amino-3-carboxylic acid ester- and 2-amino-3-cyano-thiophene derivatives (Ia)

| Compound nr and code | $R_0$ | $R_1$ | $R_2$ | $R_3$ | $R_4$ | $R_5$ | $R_6$ | $R_7$ | n | $IC_{50 \mu M}$ (CEM) |
|---|---|---|---|---|---|---|---|---|---|---|
| 16b TR587 | $NH_2$ | —COOEt | H | MeO | H | H | MeO | H | 2 | 0.76 |
| 20 TR588 | $NH_2$ | —CN | H | H | H | H | H | H | 2 | 47 |
| 24 TR589 | $NH_2$ | —CN | H | MeO | H | H | MeO | H | 2 | 0.015 |
| 19 TR592 | $NH_2$ | —COOEt | —COOEt | MeO | H | H | MeO | H | 2 | 20 |
| 10 TR596[b] | $NH_2$ | —COOMe | H | — | — | — | — | — | 2 | 63 |
| 11 TR597[c] | $NH_2$ | —COOMe | H | — | — | — | — | — | 2 | 50 |
| 8 TR599 | $NH_2$ | —COOMe | Me | MeO | H | H | MeO | H | 2 | 44 |
| 6 TR601 | $NH_2$ | —COOMe | H | MeO | H | H | MeO | H | 0 | 42 |
| 25 TJ19 | $NH_2$ | —CONHMe | H | H | H | MeO | H | H | 2 | 31 |
| 26 TJ8 | $NH_2$ | —COOH | H | H | H | MeO | H | H | 2 | 31 |
| 27 TJ9 | $NH_2$ | —$CONH_2$ | H | H | H | MeO | H | H | 2 | 39 |
| 28 TJ6A | $NHCH_3$ | —COOMe | H | H | H | MeO | H | H | 2 | 23 |
| 29 TJ6B | $N(CH_3)_2$ | —COOMe | H | H | H | MeO | H | H | 2 | 18 |
| 30 TJ7 | H | —COOMe | H | H | H | MeO | H | H | 2 | 87 |

[a]Phenyl replaced by a thiophene;
[b]Phenyl replaced by a N-2 pyridine;
[c]Phenyl replaced by a N-3 pyridine;
[d]Ethylene ($C_2H_4$) bridge replaced by an acetylene (—C≡C—) bridge.

Minor structural modifications resulted in a wide difference of antiproliferative activities, 24 being the most potent agent ($IC_{50}$ range between 0.02 and 0.13 µM) and 23 being the least active agent ($IC_{50}$ range between 24 and 320 µM), that is a difference by at least 3 orders of magnitude (Tables 2-4).

When considering the non-selective cytostatic compounds, the highest activity has been observed for the cyano-substituted compound 24, being 50-fold more cytostatic than the corresponding —COOEt-containing compound 16b. However, the replacement of the —COO alkyl group on the thiophene by a —C≡N group does not guarantee an improved antiproliferative activity since the cyano-containing compounds 23, 21, 22 and 20 are inferior to their —COOMe-containing counterparts, respectively compounds 15, 2, 3 and 1. Thus this invention relates to several and different compounds with different modifications with different cytostatic activity and tumor cell selectivity.

Evaluation of Cytostatic Activity of Compounds of Table 1a Against Leukemia/Lymphoma/Monocytic Cell Lines.

The compounds were first evaluated against a set of 7 different tumor cell lines derived from T-cell lymphomas (Table 2). Whereas the majority of the individual compounds showed rather narrow variations in their antiproliferative activity range for all these tumor cell lines, there were seven notable exceptions on this rule. These seven compounds (3, 1, 2, 7, 9, 14 and 13) were endowed with moderate middle-micromolar cytostatic activity against MT-4 and HUT-78 cells ($IC_{50}$ range: 8.5 to 60 µM) but showed pronounced cytostatic activities against CEM, Molt4/C8, Sup T1, MT-2 and C8166 cells ($IC_{50}$ range for these compounds against the 5 tumor cell lines: 0.22 to 3.4 µM). Such a strikingly increased cytostatic activity against those five T-lymphocyte tumor cell lines was not observed for any of the other 2-aminothiophene derivatives (Table 2; FIG. 1A). Common features for these unusually selective compounds are a carboxymethyl or carboxyethyl group at $R^1$ of the thiophene ring, one single methoxy on the aryl part of the molecule and a bridge between aryl and thiophene that consists of 2 carbons (either an ethylene or an acetylene). The compounds were also considerably less cytostatic against the B-lymphoma Raji and Daudi cells, as well as the monocytic U937 and THP-1 cells and the promyelocytic HL-60 cells (Table 2).

TABLE 2

Cytostatic activity (µM) of 2-aminothiophene derivatives against T-cell lymphoma, B-lymphoma and monocyte-derived cell lines. HL60, human leukemia cells that can be differentiated into monocytes; U937, human monocytic cells, derived from acute myeloid leukemia (AML); THP-1, human monocytic cells that can be differentiated to macrophage cells; Raji, non-Hodgkin leukemia/human B-lymphoma cells; Daudi, human B-lymphoma cells.

| | CEM | Molt4/C8 | Sup T 1 | MT 2 | C8166 | HUT 78 | MT 4 |
|---|---|---|---|---|---|---|---|
| TR 560 | 0.90 ± 0.43 | 0.27 ± 0.08 | 0.58 ± 0.26 | 0.57 ± 0.064 | 1.3 ± 0.87 | 21 ± 12 | 25 ± 12 |
| TR 575 | 1.5 ± 1.3 | 1.2 ± 0.6 | 1.1 ± 0.73 | 0.79 ± 0.092 | 2.2 ± 0 | 36 ± 13 | 27 ± 0.71 |

TABLE 2-continued

Cytostatic activity (μM) of 2-aminothiophene derivatives against T-cell lymphoma, B-lymphoma and monocyte-derived cell lines. HL60, human leukemia cells that can be differentiated into monocytes; U937, human monocytic cells, derived from acute myeloid leukemia (AML); THP-1, human monocytic cells that can be differentiated to macrophage cells; Raji, non-Hodgkin leukemia/human B-lymphoma cells; Daudi, human B-lymphoma cells.

| | | | | | | | |
|---|---|---|---|---|---|---|---|
| TR 567 | 1.8 ± 0.92 | 0.81 ± 0.49 | 1.5 ± 0 | 2.1 ± 0.071 | 3.0 ± 0.21 | 13 ± 4.2 | 14 ± 2.8 |
| TR 583 | 1.5 ± 0.28 | 0.27 ± 0.27 | 0.95 ± 0.64 | 1.8 ± 0.64 | 1.6 ± 0.95 | 39 ± 27 | 60 ± 0.71 |
| TR 595 | 1.7 ± 1.1 | 0.56 ± 0.57 | 1.3 ± 0.21 | 0.57 ± 0.078 | 2.2 ± 0.35 | 38 ± 8.5 | 30 ± 4.9 |
| TR 530 | 0.73 ± 0.62 | 0.22 ± 0 | 1.5 ± 0.14 | 1.5 ± 0.21 | 2.8 ± 0.14 | 44 ± 6.4 | 22 ± 15 |
| TR 532 | 1.9 ± 0.99 | 0.34 ± 0 | 1.5 ± 0.071 | 1.7 ± 0.14 | 3.4 ± 0.071 | 22 ± 9.2 | 8.5 ± 0.92 |
| TR 525 | 40 ± 1 | 18 ± 2.1 | 86 ± 7.1 | 52 ± 5.7 | 102 ± 16 | 117 ± 21 | >100 |
| TR 531 | 27 ± 10 | 31 ± 2.1 | 28 ± 12 | 27 ± 4.2 | 133 ± 7.8 | 108 ± 5.7 | 44 ± 5.7 |
| TR 542 | 20 ± 4 | 6.8 ± 0 | 23 ± 2.1 | 79 ± 17 | 143 ± 32 | 107 ± 70 | 41 ± 5.7 |
| TR 547 | 72 ± 6.4 | 54 ± 6 | 73 ± 13 | 31 ± 29 | 122 ± 12 | 120 ± 44 | 38 ± 3.5 |
| TR 572 | 74 ± 3.5 | 44 ± 9 | 55 ± 30 | 12 ± 1.4 | 179 ± 18 | 26 ± 17 | 40 ± 12 |
| TR 581 | 55 ± 0 | 39 ± 8 | 45 ± 31 | 103 ± 52 | 149 ± 14 | 152 ± 44 | 36 ± 15 |
| TR 582 | 233 ± 29 | 275 ± 89 | >200 | ≥161 | >200 | >200 | 76 ± 35 |
| TR 584 | 1.6 ± 0.071 | 0.42 ± 0.11 | 0.61 ± 0.26 | 4.2 ± 0.79 | 1.4 ± 0.76 | 2.6 ± 2.1 | 1.6 ± 0.21 |
| TR 585 | 8.3 ± 2.4 | 2.0 ± 0.2 | 4.7 ± 0.38 | 4.75 ± 0.08 | 16 ± 6.5 | 7.1 ± 1.3 | 8.1 ± 0.78 |
| TR 586 | 16 ± 17 | 1.4 ± 0.8 | 79 ± 42 | 6.8 ± 3.7 | 57 ± 56 | 17 ± 8.1 | 74 ± 37 |
| TR 587 | 0.76 ± 0.48 | 1.1 ± 1.0 | 0.54 ± 0.007 | 0.70 ± 0.30 | 0.82 ± 0.16 | 0.43 ± 0.24 | 1.7 ± 0.59 |
| TR 588 | 47 ± 25 | 8.5 ± 3.4 | >200 | 6.65 ± 1.9 | ≥200 | 18 ± 7.1 | 75 ± 35 |
| TR 589 | 0.015 ± 0 | 0.058 ± 0.056 | 0.017 ± 0.012 | 0.027 ± 0.001 | 0.021 ± 0.009 | 0.062 ± 0.039 | 0.086 ± 0.048 |
| TR 592 | 20 ± 6 | 24 ± 17 | 4.1 ± 0.40 | 8.1 ± 1.2 | 25 ± 3.5 | 26 ± 3.5 | 36 ± 16 |
| TR 596 | 63 ± 7.8 | 21 ± 4 | 99 ± 0 | 48 ± 7.1 | ≥200 | 142 ± 83 | >100 |
| TR 597 | 50 ± 6.4 | 47 ± 15 | 147 ± 66 | 38 ± 15 | ≥200 | 59 ± 33 | >100 |
| TR 599 | 44 ± 0 | 47 ± 16 | 32 ± 15 | 37 ± 29 | 110 ± 31 | 21 ± 1.4 | 58 ± 21 |
| TR 601 | 42 ± 1.4 | 28 ± 6 | 38 ± 25 | 14 ± 2.8 | 102 ± 1.4 | 109 ± 82 | 50 ± 25 |

| | HL 60 | U937 | THP-1 | Raji | Daudi | L1210 |
|---|---|---|---|---|---|---|
| TR 560 | 4.7 ± 6.4 | 40 ± 5.7 | 36 ± 0 | 57 ± 16 | 46 ± 11 | 11 ± 1 |
| TR 575 | 5.7 ± 7.2 | 46 ± 7.1 | 38 ± 6.4 | 50 ± 3.5 | 38 ± 2.1 | 25 ± 0 |
| TR 567 | 4.0 ± 3.3 | 10 ± 0.85 | 13 ± 1.4 | 19 ± 4.2 | 13 ± 0.71 | 17 ± 5 |
| TR 583 | 4.9 ± 5.4 | 40 ± 2.8 | 32 ± 4.9 | 93 ± 11 | 61 ± 1.4 | 248 ± 40 |
| TR 595 | 6.1 ± 8.6 | 42 ± 3.5 | 41 ± 2.8 | 46 ± 1.4 | 37 ± 3.5 | 41 ± 2 |
| TR 530 | 6.2 ± 8.5 | 41 ± 1.4 | 44 ± 1.4 | 48 ± 1.4 | 43 ± 2.8 | 40 ± 2 |
| TR 532 | 7.0 ± 8.7 | 43 ± 1.4 | 23 ± 3.5 | 39 ± 2.8 | 43 ± 2.1 | 20 ± 10 |
| TR 525 | 62 ± 9.9 | 115 ± 19 | 102 ± 2.8 | >100 | | 44 ± 3 |
| TR 531 | 17 ± 5.7 | 73 ± 3.5 | 25 ± 19 | 48 ± 13 | | 41 ± 3 |
| TR 542 | 11 ± 2.2 | 80 ± 5.7 | 31 ± 13 | 55 ± 12 | | 40 ± 0 |
| TR 547 | 46 ± 25 | 80 ± 3.5 | 26 ± 2.8 | 58 ± 13 | | 105 ± 48 |
| TR 572 | 11 ± 1.4 | 63 ± 7.1 | 21 ± 0.7 | 61 ± 18 | | 60 ± 12 |
| TR 581 | 16 ± 3.5 | 82 ± 7.1 | 69 ± 13 | 59 ± 11 | | 204 ± 85 |
| TR 582 | ≥135 | >200 | 124 ± 25 | >100 | | 230 ± 65 |
| TR 584 | 0.89 ± 0.30 | 4.2 ± 0.070 | 3.1 ± 0.070 | 2.2 ± 0.28 | | 1.8 ± 0.1 |
| TR 585 | 3.5 ± 0.57 | 3.4 ± 2.8 | 3.8 ± 0.60 | 13 ± 3.5 | | 15 ± 4 |
| TR 586 | 1.9 ± 0.42 | 17 ± 2.8 | 4.3 ± 0.60 | 36 ± 21 | | 14 ± 4 |
| TR 587 | 0.46 ± 0.35 | 0.92 ± 0.080 | 0.71 ± 0.18 | 1.8 ± 0.42 | | 1.2 ± 0.4 |
| TR 588 | 3.9 ± 0.50 | 42 ± 2.1 | 8.4 ± 0.28 | 39 ± 21 | | 40 ± 6 |
| TR 589 | 0.024 ± 0.004 | 0.036 ± 0.001 | 0.022 ± 0.003 | 0.063 ± 0.013 | | 0.064 ± 0.025 |
| TR 592 | 17 ± 0.70 | 20 ± 15 | 20 ± 1.4 | 41 ± 7.1 | | 34 ± 3 |
| TR 596 | 73 ± 30 | >200 | 116 ± 49 | 76 ± 35 | | 101 ± 28 |
| TR 597 | 63 ± 15 | >200 | >200 | >100 | | 235 ± 49 |
| TR 599 | 18 ± 4.9 | 68 ± 0.7 | 9.0 ± 0.60 | 49 ± 13 | | 46 ± 3 |
| TR 601 | 21 ± 0 | 85 ± 2.8 | 25 ± 5.7 | 45 ± 11 | | 50 ± 5 |

Evaluation of Cytostatic Activity of Compounds of Table 1a Against a Broad Variety of Tumor Cell Lines, Different from Leukemia/Lymphoma/Monocytic Cell Lines.

Figure 1B:
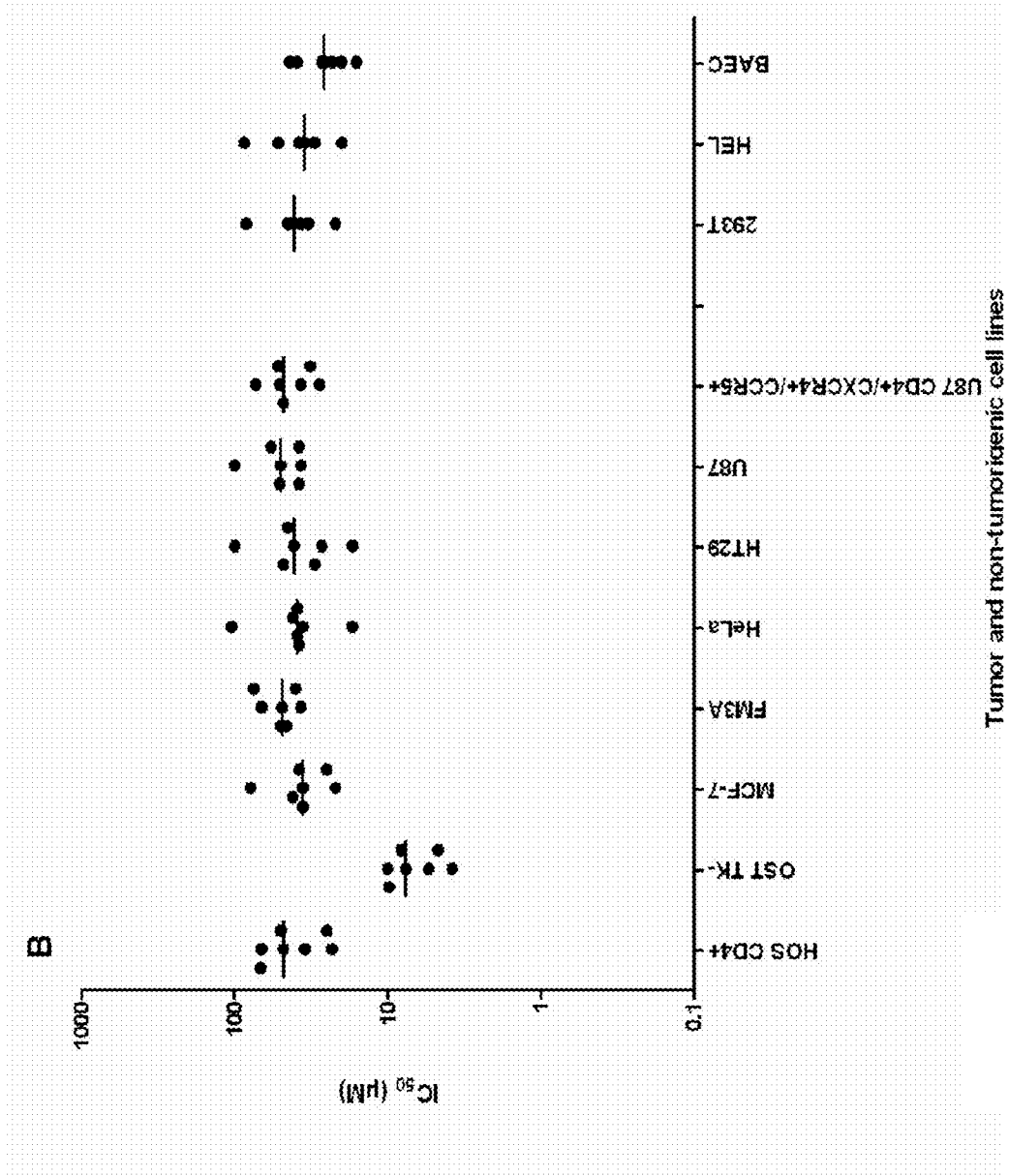

A moderate (middle to higher micromolar) cytostatic activity range was observed against a variety of other tumor cell types including osteosarcoma HOS CD4+, human MCF-7 and murine FM3A mammary carcinoma, cervix carcinoma HeLa, colorectal carcinoma HT29, glioma U87 and U87 CD4+.CXCR4+.CCR5+, and non-tumorigenic kidney embryo fibroblast 293T, human embryonic lung fibroblast HEL and bovine aortic endothelial BAEC cells (Table 3; FIG. 1B). The human kidney carcinoma Caki-1 was in general markedly more sensitive to the cytostatic activity of 3, 1, 2, 7, 9, 14 and 13 than the Caki-2 cells.

TABLE 3

Cytostatic activity (μM) of 2-aminothiophene derivatives against a broad variety of tumor cell lines. HOS, OST TK⁻, human osteosarcoma cells; MCF-7, human mammary carcinoma cells; FM3A, murine mammary carcinoma cells; HeLa, human cervix carcinoma cells; 293T, human embryonic kidney cells; HT19, human colon carcinoma cells; U87, human glioma cells; Caki-1 and Caki-2, human kidney carcinoma cells; HEL, human embryonic fibroblast cells; BAEC, bovine artery endothelial cells.

| | HOS CD4⁺ | OST TK- | MCF-7 | FM3A | Hela | Caki-1 | Caki-2 |
|---|---|---|---|---|---|---|---|
| TR 560 | 68 ± 25 | 4.7 ± 3.3 | 38 ± 2.1 | 75 ± 36 | 39 ± 11 | 1.7 ± 1.1 | 33 ± 32 |
| TR 575 | 48 ± 1.4 | 9.8 ± 7.4 | 36 ± 9.2 | 67 ± 18 | 38 ± 2.8 | 6.5 ± 3.5 | 43 ± 4.2 |
| TR 567 | 23 ± 4.2 | 7.6 ± 2.4 | 22 ± 3.5 | 37 ± 0.71 | 17 ± 2.1 | 3.7 ± 1.8 | 4.5 ± 1.9 |
| TR 583 | 67 ± 6.4 | 10 ± 6.9 | 79 ± 30 | 49 ± 9.9 | 105 ± 68 | 4.5 ± 3.8 | ≥200 |
| TR 595 | 50 ± 12 | 8.2 ± 6.9 | 25 ± 11 | 50 ± 2.8 | 36 ± 7 | 2.3 ± 0.14 | 45 ± 7.1 |
| TR 530 | 35 ± 7.1 | 3.8 ± 1.7 | 42 ± 0.71 | 40 ± 3.5 | 42 ± 5.5 | 5.3 ± 2.2 | 88 ± 17 |
| TR 532 | 25 ± 5.7 | 5.4 ± 3.3 | 36 ± 5.7 | 46 ± 6.0 | 39 ± 0 | 4.6 ± 2.1 | 66 ± 37 |
| TR 525 | | 79 ± 2.8 | 81 ± 4.9 | 49 ± 6 | 39 ± 4 | 83 ± 36 | 159 ± 19 |
| TR 531 | | 18 ± 1.4 | 48 ± 11 | 49 ± 1 | 40 ± 9 | 17 ± 3.5 | 17 ± 3.5 |
| TR 542 | | 41 ± 0.71 | 60 ± 0.7 | 53 ± 7 | 45 ± 6 | 62 ± 12 | 16 ± 10 |
| TR 547 | | 71 ± 7.8 | 87 ± 21 | 86 ± 5.6 | 41 ± 7.1 | 87 ± 21 | 57 ± 24 |
| TR 572 | | 25 ± 2.1 | 119 ± 52 | 97 ± 32 | 63 ± 19 | 4.4 ± 1.9 | 9.0 ± 1.4 |
| TR 581 | | 45 ± 4.2 | 29 ± 20 | 275 ± 206 | 41 ± 4.9 | 39 ± 2.1 | 28 ± 18 |
| TR 582 | | 134 ± 69 | 117 ± 58 | 320 ± 14 | 168 ± 15 | 19 ± 18 | ≥200 |
| TR 584 | | 0.68 ± 0.33 | 0.93 ± 0.23 | 2.5 ± 0.28 | 0.83 ± 0.25 | 2.5 ± 0.6 | 0.93 ± 0.28 |
| TR 585 | | 3.96 ± 1.56 | 5.42 ± 0.69 | 25 ± 0.71 | 8.3 ± 1.5 | 4.6 ± 1.3 | 4.8 ± 4.5 |
| TR 586 | | 27 ± 18 | 114 ± 62 | 34 ± 23 | 21 ± 9.9 | 1.9 ± 0.42 | 28 ± 27 |
| TR 587 | | 0.51 ± 0.42 | 0.83 ± 0.35 | 2.0 ± 0.28 | 0.33 ± 0.028 | 1.4 ± 0.5 | 3.2 ± 2.4 |
| TR 588 | | 27 ± 18 | 26 ± 2.1 | 67 ± 23 | 27 ± 28 | 1.3 ± 0.4 | 78 ± 69 |
| TR 589 | | 0.024 ± 0.013 | 0.026 ± 0.0014 | 0.050 ± 0.046 | 0.13 ± 0.06 | 0.016 ± 0.001 | 0.042 ± 0.004 |
| TR 592 | | 17 ± 5.7 | 27 ± 19 | 33 ± 9 | 11 ± 3 | 24 ± 0.7 | 42 ± 2.1 |
| TR 596 | | 135 ± 92 | 72 ± 45 | 210 ± 17 | 45 ± 3 | 17 ± 13 | >200 |
| TR 597 | | ≥111 | 71 ± 30 | 164 ± 30 | 170 ± 25 | 7.7 ± 0.5 | >200 |
| TR 599 | | 34 ± 23 | 11 ± 8.5 | 48 ± 3.5 | 38 ± 11 | 57 ± 38 | 52 ± 17 |
| TR 601 | | 32 ± 18 | 44 ± 28 | 59 ± 11 | 39 ± 9.2 | 8.8 ± 3.1 | 24 ± 9.2 |

| | 293T | HT29 | U87 | U87 CD4+/CXCR4+/CCR5+ | HEL | BAEC |
|---|---|---|---|---|---|---|
| TR 560 | 33 ± 25 | 45 ± 5.7 | 58 ± 6.4 | 52 ± 3.5 | 52 ± 25 | 39 ± 8.5 |
| TR 575 | 45 ± 16 | 41 ± 2.8 | 50 ± 3.5 | 73 ± 3.5 | 38 ± 12 | 26 ± 4.2 |
| TR 567 | 22 ± 15 | 17 ± 7.8 | 38 ± 0 | 32 ± 2.1 | 20 ± 7.8 | 20 ± 4.2 |
| TR 583 | 84 ± 23 | >100 | >100 | 48 ± 6.4 | 87 ± 19 | 44 ± 22 |
| TR 595 | 44 ± 5.7 | 30 ± 5.7 | 51 ± 2.1 | 51 ± 4.9 | 30 ± 13 | 27 ± 7.1 |
| TR 530 | 37 ± 0.71 | 48 ± 23 | 37 ± 2.8 | 28 ± 3.5 | 35 ± 13 | 16 ± 16 |
| TR 532 | 41 ± 0.71 | 27 ± 13 | 38 ± 1.4 | 37 ± 9.9 | 20 ± 8.5 | 23 ± 0.71 |
| TR 525 | >100 | 93 ± 11 | 90 ± 14 | | 43 ± 9.9 | 74 ± 26 |
| TR 531 | 58 ± 7.1 | 43 ± 2.8 | 38 ± 8.5 | | 25 ± 3.5 | 31 ± 6.4 |
| TR 542 | >100 | >100 | >100 | | 43 ± 4.9 | >100 |
| TR 547 | 58 ± 2.8 | 46 ± 3.5 | 81 ± 27 | | 44 ± 3.5 | 82 ± 26 |
| TR 572 | >100 | 42 ± 3.5 | 71 ± 3.5 | | 34 ± 20 | 47 ± 3.5 |
| TR 581 | 72 ± 4.9 | 43 ± 1.4 | 42 ± 5.7 | | 24 ± 2.1 | 38 ± 2.1 |
| TR 582 | >100 | >100 | >100 | | 33 ± 0.71 | >100 |
| TR 584 | 1.9 ± 0 | 1.8 ± 0.21 | 1.8 ± 0.071 | | 0.87 ± 0.014 | 2.0 ± 0.28 |
| TR 585 | 10 ± 0.071 | 8.9 ± 0.92 | 10 ± 0.78 | | 7.2 ± 0.49 | 9.7 ± 1.8 |
| TR 586 | 28 ± 3.5 | 34 ± 6.4 | >100 | | >100 | 38 ± 2.1 |
| TR 587 | 1.0 ± 0.11 | 1.7 ± 0.14 | 1.6 ± 1.1 | | 0.27 ± 0.22 | 0.93 ± 0.67 |
| TR 588 | 34 ± 14 | 66 ± 6.4 | 46 ± 7.8 | | 30 ± 6.4 | 45 ± 4.9 |
| TR 589 | <0.032 | 0.046 ± 0.012 | 0.038 ± 0.008 | | <0.032 | <0.032 |
| TR 592 | 30 ± 7.1 | 43 ± 4.2 | 39 ± 2.8 | | 35 ± 6.4 | 31 ± 4.2 |
| TR 596 | >100 | >100 | >100 | | 43 ± 9.2 | >100 |
| TR 597 | >100 | >100 | >100 | | ≥100 | >100 |
| TR 599 | 52 ± 2.1 | 47 ± 2.1 | 41 ± 4.9 | | 46 ± 3.5 | 52 ± 46 |
| TR 601 | 43 ± 16 | 42 ± 0 | 25 ± 0 | | 17 ± 5.7 | 26 ± 7.1 |

Evaluation of Compounds of Table 1a Against Prostate and Hepatoma Cancer Cell Lines.

Figure 1C:
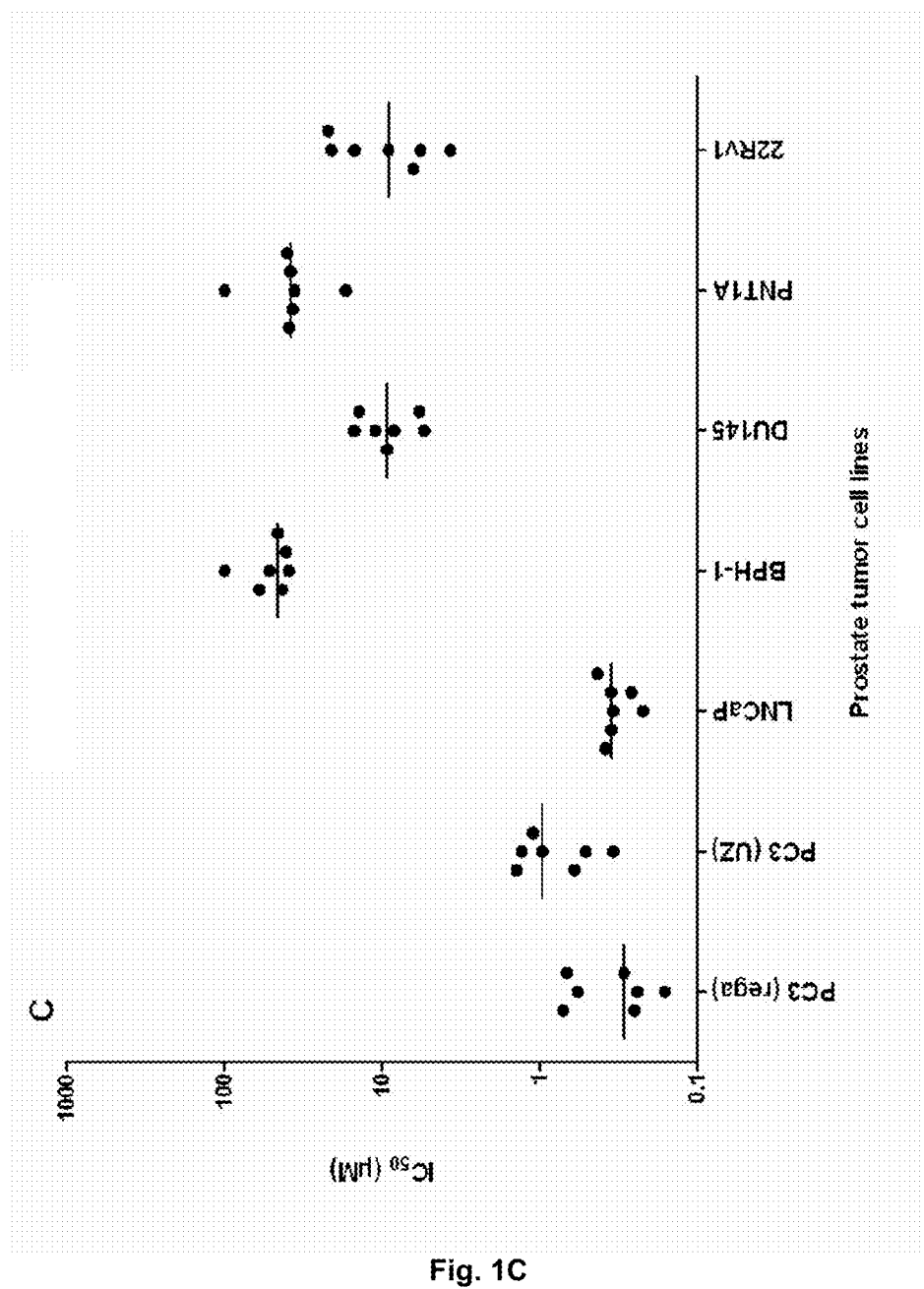

However, when the compounds were evaluated for their inhibitory potential against the proliferation of three human hepatoma cell lines (i.e. Huh7, HepG2C3A and PLC/PRF/5) and seven different prostate cancer cell lines, again, the same compounds that showed preferential inhibition of several T-cell lymphoma-derived tumor cell lines, also showed an increased cytostatic activity against the Huh7 cells and an (even more) unusual increased cytostatic potential against several of the prostate tumor cell lines (Table 4; FIG. 1C). Nanomolar cytostatic activity was observed against two different PC3 sources and against LNCaP cells, low micromolar antiproliferative activity was shown for DU145 and 22Rv1 prostate cancer cells, and moderate activity was shown against BPH-1 and PNT1A prostate cancer cells. In contrast with what had been observed for the lymphoma cell lines, the other non-selective group of compounds were preferentially cytostatic to the PC3 and LNCaP cell lines compared to the other prostate tumor cell lines.

TABLE 4

Cytostatic activity (μM) of 2-aminothiophene derivatives against prostate and hepatoma cancer cell lines

| | PC3 (rega) | BPH-1 (UZ) | DU145 (UZ) | PC-3 (UZ) | LNCaP (UZ) |
|---|---|---|---|---|---|
| TR 560 | 0.19 ± 0.035 | 60 ± 0 | 5.8 ± 2.8 | 0.34 ± 0.14 | 0.22 ± 0.042 |
| TR 575 | 0.24 ± 0.19 | 52 ± 1.4 | 5.4 ± 0.96 | 0.51 ± 0.064 | 0.35 ± 0.014 |
| TR 567 | 0.71 ± 0.28 | 39 ± 2.8 | 11 ± 7.0 | 1.4 ± 0.071 | 0.43 ± 0.14 |
| TR 583 | 0.57 ± 0.30 | >100 | 14 ± 1.2 | 1.3 ± 0.071 | 0.35 ± 0.067 |
| TR 595 | 0.25 ± 0.27 | 46 ± 4.9 | 15 ± 8.5 | 0.60 ± 0.071 | 0.38 ± 0.10 |
| TR 530 | 0.29 ± 0.14 | 41 ± 1.4 | 9.3 ± 8.4 | 0.96 ± 0.20 | 0.26 ± 0.081 |
| TR 532 | 0.67 ± 0.14 | 43 ± 2.8 | 8.4 ± 1.6 | 1.1 ± 0.49 | 0.34 ± 0.050 |
| TR 525 | 13 ± 9.6 | 36 ± 1.4 | 41 ± 24 | 20 ± 3.5 | 2.3 ± 0.071 |
| TR 531 | 25 ± 6.4 | 39 ± 0 | 34 ± 4.2 | 28 ± 0.71 | 11 ± 5.0 |
| TR 542 | 8.6 ± 3.4 | 74 ± 4.2 | 34 ± 7.1 | 8.5 ± 3.5 | 3.8 ± 2.9 |
| TR 547 | 38 ± 12 | 65 ± 9.2 | 89 ± 16 | 31 ± 5.7 | 19 ± 10 |
| TR 572 | 5.5 ± 4.0 | 58 ± 6.4 | 18 ± 9.2 | 4.3 ± 1.7 | 1.1 ± 0.84 |
| TR 581 | 26 ± 8.5 | 50 ± 5.7 | 35 ± 6.4 | 28 ± 4.9 | 9.7 ± 5.1 |
| TR 582 | 69 ± 21 | >100 | >100 | >100 | 4.8 ± 3.4 |
| TR 584 | 0.36 ± 0.18 | 1.3 ± 0.071 | 1.6 ± 0 | 0.81 ± 0.42 | 0.38 ± 0.11 |
| TR 585 | 1.7 ± 0.35 | 7.0 ± 0.42 | 6.4 ± 1.8 | 2.6 ± 0.64 | 2.7 ± 0.95 |
| TR 586 | 1.8 ± 2.0 | 59 ± 18 | 8.3 ± 2.5 | 4.2 ± 0.14 | 0.83 ± 0.35 |
| TR 587 | 0.33 ± 0.099 | 0.39 ± 0.007 | 1.4 ± 0.21 | 0.52 ± 0.007 | 0.35 ± 0.064 |
| TR 588 | 3.1 ± 1.2 | ≥100 | 24 ± 4.9 | 11 ± 4.2 | 5.3 ± 4.3 |
| TR 589 | <0.032 | <0.032 | 0.061 ± 0.016 | <0.032 | <0.032 |
| TR 592 | 12 ± 2.1 | 28 ± 3.5 | 18 ± 2.1 | 8.5 ± 0.85 | 4.1 ± 3.6 |
| TR 596 | 8.5 ± 7.8 | >100 | >100 | 8.6 ± 0.21 | 4.3 ± 3.2 |
| TR 597 | 6.3 ± 4.7 | >100 | 60 ± 21 | 12 ± 5.5 | 7.4 ± 0.75 |
| TR 599 | 24 ± 12 | 43 ± 3.5 | 35 ± 16 | 25 ± 5.7 | 8.7 ± 4.7 |
| TR 601 | 23 ± 14 | 31 ± 0 | 37 ± 2.1 | 25 ± 0 | 21 ± 8.5 |

| | PNT1A (UZ) | 22Rv1 (UZ) | PLC/PRF/5 | HepG2C3A | Huh-7 |
|---|---|---|---|---|---|
| TR 560 | 36 ± 9.2 | 3.7 ± 2.2 | 36 ± 1.4 | 8.4 ± 2.1 | 0.95 ± 0.21 |
| TR 575 | 39 ± 3.5 | 9.1 ± 0.35 | 44 ± 2.1 | 10 ± 5.2 | 1.7 ± 0.21 |
| TR 567 | 17 ± 2.8 | 5.7 ± 2.8 | 18 ± 4.2 | 8.6 ± 0.28 | 3.4 ± 1.2 |
| TR 583 | >100 | 21 ± 17 | 62 ± 21 | 13 ± 0.71 | 4.6 ± 0.28 |
| TR 595 | 40 ± 7.1 | 22 ± 9.2 | 28 ± 2.8 | 8.1 ± 0.71 | 1.3 ± 0.28 |
| TR 530 | 38 ± 7.8 | 6.3 ± 2.5 | 41 ± 6.4 | 12 ± 2.1 | 1.5 ± 0.28 |
| TR 532 | 37 ± 9.9 | 15 ± 7.9 | 24 ± 2.1 | 6.7 ± 0.35 | 1.6 ± 0.14 |
| TR 525 | 42 ± 5.7 | 16 ± 5.5 | >100 | >100 | >100 |
| TR 531 | 45 ± 1.4 | 20 ± 5.1 | 21 ± 0.71 | 10 ± 5.2 | 43 ± 12 |
| TR 542 | 45 ± 0 | 33 ± 0.71 | 39 ± 5.7 | 30 ± 0.71 | 28 ± 17 |
| TR 547 | 56 ± 0 | 31 ± 4.2 | 75 ± 35 | 48 ± 16 | 51 ± 14 |
| TR 572 | 53 ± 2.1 | 69 ± 44 | 42 ± 2.1 | 28 ± 8.5 | 42 ± 7.8 |
| TR 581 | 58 ± 13 | 42 ± 7.6 | 36 ± 4.2 | 38 ± 27 | 59 ± 17 |
| TR 582 | >100 | 34 ± 26 | 49 ± 3.5 | ≥100 | >100 |
| TR 584 | 0.77 ± 0.31 | 0.31 ± 0.087 | 1.3 ± 0.21 | 4.5 ± 1.7 | 2.2 ± 0.49 |
| TR 585 | 8.0 ± 0.42 | 9.4 ± 5.8 | 6.7 ± 0.64 | 7.2 ± 4.0 | 8.3 ± 0.78 |
| TR 586 | 38 ± 14 | 17 ± 8.1 | 37 ± 0.71 | 46 ± 13 | >100 |
| TR 587 | 0.41 ± 0.028 | 0.19 ± 0.11 | 0.26 ± 0.15 | 1.1 ± 0.49 | 0.71 ± 0.35 |
| TR 588 | 66 ± 31 | 61 ± 34 | 41 ± 3.5 | 64 ± 52 | 21 ± 7.1 |
| TR 589 | <0.032 | <0.032 | 0.041 ± 0.013 | 0.29 ± 0.18 | <0.16 |
| TR 592 | 31 ± 0.71 | 14 ± 8.3 | 25 ± 0 | 34 ± 12 | 34 ± 14 |
| TR 596 | >100 | 77 ± 27 | >100 | 69 ± 45 | 46 ± 34 |
| TR 597 | >100 | ≥100 | >100 | >100 | 78 ± 32 |
| TR 599 | 46 ± 2.1 | 28 ± 19 | 36 ± 2.8 | 34 ± 22 | 52 ± 7.8 |
| TR 601 | 38 ± 5.7 | 11 ± 4.8 | 26 ± 0.71 | 22 ± 18 | 49 ± 19 |

Thus, among a series of closely-related 2-aminothiophene analogues seven derivatives have been identified that show a preferential cytostatic activity against several T-cell lymphoma, hepatoma and prostate cancer-derived cell lines, but not against any other type of tumor or non-tumorigenic cell line included in this study.

The unusual selectivity of the compounds for several T-cell lymphoma, hepatoma and prostate cancer cell lines together with the structure-activity relationship (SAR) among the 2-aminothiophenes of this study allow us to deduce some SAR parameters. (i) The presence of a carbon bridge linking the thiophene and the phenyl group seems to be necessary for the cytostatic selectivity. For example, compounds 3, 13 and 14 containing an ethylene or acetylene bridge are selective, while their corresponding derivatives without a bridge (15 and 16a) are not selective anymore against the lymphoma, hepatoma and prostate cancer cell lines. (ii) It was surprising to notice that compound 2 containing a —COOMe group at the 3 position of the thiophene is selective while the corresponding —COOEt derivative 11 is not, although the —COOEt group does not necessarily destroy the selectivity in compounds 13 & 14. However, replacing —COO alkyl by —CN annihilates the selectivity (compare compounds 21 with 2, 22 with 3, and 20 with 1). (iii) The presence of a second —COOEt on the thiophene is detrimental for selectivity (compare compound 18 with 13). (iv) When the —COOMe at $R^1$ was replaced by an amide (27), methylamide (25), or the free carboxylic acid (26) the selective cytostatic activity was markedly decreased. (v) When the —$NH_2$ at $R^0$ was replaced by H, $NHCH_3$ or $N(CH_3)_2$ activity/selectivity was also markedly affected. (vi) The location of the methoxy group(s) also seems to play an instrumental role in tumor cell selectivity. For example, when the methoxy group is at the $R^3$ position (compound 3), selectivity is present, but adding an additional MeO group at $R^6$ (compound 5) annihilates selectivity. (vii) Finally, when the aryl had been replaced by a thiazole (compound 9), selectivity is retained, but not when the aryl had been replaced by a pyridine (compounds 10 and 11).

Example 4

Biological Activity of Further Compounds of this Invention, Compounds of Formula I(b)

Following additional structural features to preserve the cytostatic selectivity could also be derived (Table 1b): (i) the ethylene bridge can be replaced by a thiomethyl (—$SCH_2$—) (TJ22), but not by an oxymethyl (—$OCH_2$—) (TJ25) or aminomethyl (—$NHCH_2$—) (TJ51) bridge. Also bridge elongation to 3 atom units is allowed (i.e. a methylthiomethyl (—$CH_2SCH_2$—) (TJ57) bridge). In several cases, the MeO group at the aryl moiety can be replaced by a Me group or a H atom (i.e. TJ55, TJ54P, TJ57).

TABLE 1c

2-Amino-3-carboxylic acid ester derivatives without the aryl moiety

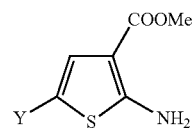

| | IC$_{50}$ (μM) | | Compound |
|---|---|---|---|
| Y | CEM | HeLa | code |
| 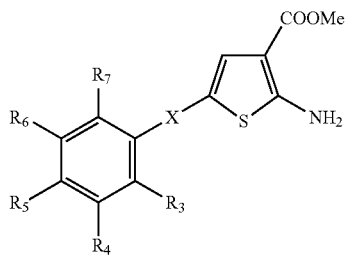 | 13 ± 5 | 97 ± 2 | TJ108 |
| | 0.28 ± 0.10 | 21 | TJ110 |
| | 0.13 | 81 | TJ114 |

(Y column entries with * indicating NH$_2$ on thiophene replaced by phthalimide group)

TABLE 1b

2-Amino-3-carboxylic acid ester derivatives with heteroatom substitutions in the bridge part, and substituent substitutions in the aryl part (Ib)

| | $R_3$ | $R_4$ | $R_5$ | $R_6$ | $R_7$ | X | IC$_{50}$ (μM) (CEM) | IC$_{50}$ (μM) (HeLa) |
|---|---|---|---|---|---|---|---|---|
| TJ22 | H | H | OMe | H | H | —SCH$_2$— | 0.62 ± 0.33 | 58 ± 1 |
| TJ25 | H | H | OMe | H | H | —OCH$_2$— | 43 ± 13 | 68 ± 13 |
| TJ51 | H | H | OMe | H | H | —NHCH$_2$— | 96 ± 16 | 78 ± 15 |
| TJ55 | H | H | Me | H | H | —SCH$_2$— | 1.5 ± 0.3 | 72 ± 30 |
| TJ54P | H | Me | H | H | H | —SCH$_2$— | 4.1 ± 1.7 | 108 ± 0 |
| TJ57 | H | H | H | H | H | —CH$_2$SCH$_2$— | 3.5 ± 1.1 | 61 ± 38 |
| TJ4 | H | H | H | H | H | —SCH$_2$— | 1.3 ± 0.6 | 108 ± 7 |
| TJ21* | H | H | OMe | H | H | —SCH$_2$— | 4.9 ± 1.4 | 112 ± 2 |
| TJ54SM* | H | Me | H | H | H | —SCH$_2$— | 6.9 ± 0.7 | 121 ± 13 |
| TJ86* | H | H | H | H | H | —SCH$_2$— | 13 ± 7 | 184 ± 6 |
| TJ113** | — | — | — | — | — | —SCH$_2$— | 0.90 ± 0.04 | 74 ± 6 |
| TJ117*** | — | — | — | — | — | —CH$_2$SCH$_2$— | 4.9 ± 0.1 | 102 ± 6 |
| TJ130 | H | H | OMe | H | H | —CH$_2$SCH$_2$— | 3.9 ± 1.4 | 88 ± 10 |
| TJ118**** | — | — | — | — | — | —CH$_2$SCH$_2$— | 3.3 ± 0.9 | 99 ± 5 |
| TJ127* | H | H | OMe | H | H | —CH$_2$SCH$_2$— | 25 ± 8 | 111 ± 20 |

*NH$_2$ on thiophene replaced by a 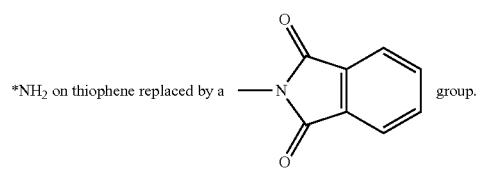 group.

**Phenyl replaced by a naphthyl.
***Phenyl replaced by a furanyl.
****Phenyl replaced by a thiophene.

TABLE 1c-continued

2-Amino-3-carboxylic acid ester derivatives without the aryl moiety

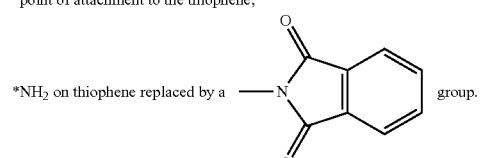

| | IC$_{50}$ (μM) | | Compound |
|---|---|---|---|
| Y | CEM | HeLa | code |
| ~~S~~* | 6.6 ± 3.2 | 104 ± 1 | TJ119* |
| ~~S~~* | 0.52 ± 0.37 | 81 ± 5 | TJ125 |

*point of attachment to the thiophene;

*NH$_2$ on thiophene replaced by a —N(phthalimide) group.

Example 5

Antimetabolic Activity of T-Cell Lymphoma Selective and Non-Selective Compounds To reveal initial insights in the molecular mechanism of the cytostatic action of the compounds, the tumor-selective compounds, as well as a selection of tumor-nonselective compounds were investigated for their potential antimetabolic activity. Prototype compound 3 and the other tumor-selective compounds have been evaluated for their antimetabolic activity by measuring their inhibitory effect against incorporation of dThd in DNA, uridine in RNA and leucine in proteins of T-lymphocyte CEM and B-lymphocyte Raji cells (Table 5). None of the compounds showed preferential inhibitory activity against DNA, RNA or protein synthesis. The inhibitory activity of the compounds against macromolecular (DNA, RNA and protein) synthesis in CEM tumor cells were generally far more pronounced for the T-lymphoma-selective compounds (1, 2, 3, 7, 9, 13 and 14) than for the tumor-nonselective compounds. Also, virtually none of the compounds, including the tumor-selective compounds, showed pronounced inhibitory activity against the B-lymphocyte Raji cells (Table 5).

TABLE 5

Inhibitory effect of test compounds against the incorporation of radiolabeled precursors in cellular macromolecules

| | IC$_{50}{}^a$ (μM) | |
|---|---|---|
| Compound | CEM | Raji |
| [CH$_3$—$^3$H]dThd incorporation | | |
| 1 | 3.1 ± 1.0 | ≥100 |
| 2 | 6.4 ± 4.1 | 54 ± 8 |
| 3 | 2.8 ± 1.3 | 63 ± 34 |
| 7 | 3.1 ± 0.3 | >100 |
| 9 | 3.2 ± 1.2 | 39 ± 33 |
| 13 | 11 ± 4 | >100 |
| 14 | 2.3 ± 1.0 | ≥100 |

TABLE 5-continued

Inhibitory effect of test compounds against the incorporation of radiolabeled precursors in cellular macromolecules

| | IC$_{50}{}^a$ (μM) | |
|---|---|---|
| Compound | CEM | Raji |
| 5 | 7.5 ± 5.5 | 82 ± 6 |
| 12 | 68 ± 14 | ≥100 |
| 16a | 15 ± 3 | ≥100 |
| 19 | 17 ± 8 | 25 ± 16 |
| 21 | >100 | ≥100 |
| 24 | >100 | ≥100 |
| [5-$^3$H]uridine incorporation | | |
| 1 | 0.96 ± 0.37 | >100 |
| 2 | 2.6 ± 0.6 | 68 ± 8 |
| 3 | 1.1 ± 0.7 | 47 ± 19 |
| 7 | 1.0 ± 0.5 | >100 |
| 9 | 1.9 ± 0.7 | 27 ± 14 |
| 13 | 3.0 ± 0.1 | >100 |
| 14 | 0.66 ± 0.01 | 60 ± 57 |
| 5 | 2.4 ± 0.2 | ≥100 |
| 12 | 39 ± 32 | ≥100 |
| 16a | 12 ± 5 | 82 ± 26 |
| 19 | 31 ± 22 | 31 ± 19 |
| 21 | ≥100 | ≥100 |
| 24 | 44 ± 11 | 90 ± 14 |
| [4,5-$^3$H]leucine incorporation | | |
| 1 | 0.61 ± 0.04 | 84 ± 6 |
| 2 | 1.4 ± 0.9 | 45 ± 8 |
| 3 | 0.19 ± 0.13 | 52 ± 10 |
| 7 | 1.9 ± 1.6 | >100 |
| 9 | 0.66 ± 0.13 | 43 ± 7 |
| 13 | 1.6 ± 1.1 | ≥100 |
| 14 | 0.20 ± 0.07 | ≥100 |
| 5 | 1.1 ± 0.5 | 62 ± 1 |
| 12 | 23 ± 14 | 94 ± 7 |
| 16a | 6.2 ± 7.6 | ≥100 |
| 19 | 17 ± 0 | 23 ± 7 |
| 21 | 11 ± 8 | ≥100 |
| 24 | 20 ± 0.16 | 39 ± 36 |

$^a$50% Inhibitory concentration or compound concentration required to inhibit incorporation of the radiolabeled precursor into TCA-insoluble material by 50%.

Figure 2:
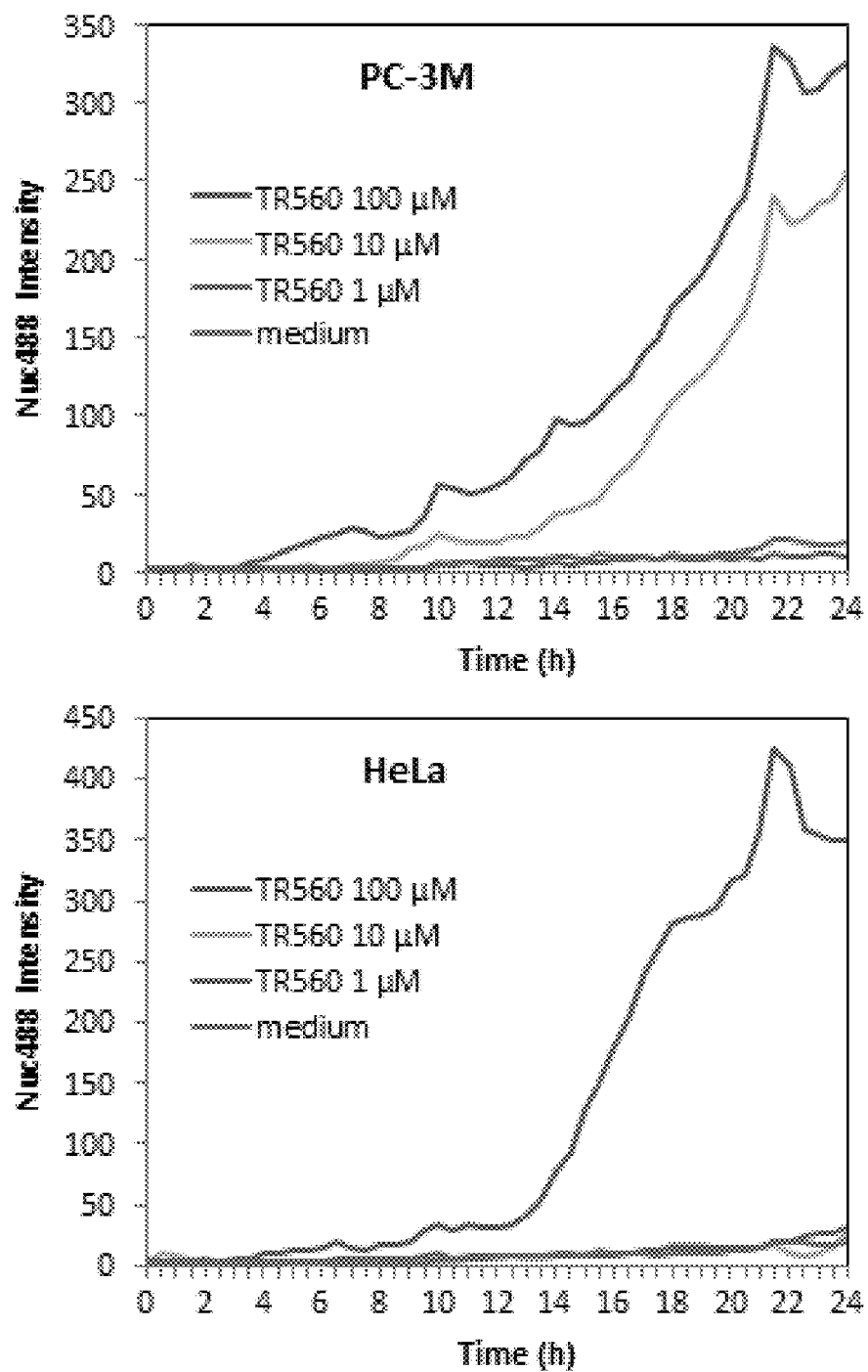
FIG. 2. PC-3M or HeLa cells were seeded in µ-angiogenesis slides at 50,000 cells/cm² in DMEM with 10% FBS. After 24 h, the cells were incubated in HBSS with 10% FBS containing different concentrations of compound 3 and 2 µM of the caspase-3 substrate NucViewTM 488-DEVD. Real-time imaging of caspase-3 activity in the nucleus of living cells was performed every 30 min for 24 h.

FACS analysis revealed that the compound 3-exposed CEM cells did not selectively cause accumulation of the tumor cells in a specific cell phase (i.e. Mitosis, G1, S or G2) ( ) and thus, seems not to cause selective inhibition of a specific cell function directly related to any of the cell phases. However, treatment of PC-3M prostate carcinoma cells with 100 or 10 μM compound 3 resulted in the activation of caspase-3 after 6 h and 12 h, respectively (FIG. 2). No induction of apoptosis was observed in the presence of 1 μM compound 3. Under identical experimental conditions, activation of caspase-3 in HeLa cells was only observed after 12 h in the presence of 100 μM compound 3. Thus, compound 3 seemed to induce caspase-3-related apoptosis in PC-3 cell cultures.

The unusual and surprising cytostatic selectivity was observed for a number of 2-aminothiophene derivatives substituted at the 5-position of the thiophene ring. These compounds showed a preferential anti-proliferative activity against a variety of T-cell lymphoma, hepatoma and prostate cancer cell lines. They do not discriminate for inhibition of DNA, RNA and protein synthesis, and do not specifically lead to an accumulation of the drug-exposed tumor cells in a well-defined cell phase. The prototype compound 3 induced apoptosis in prostate tumor cell cultures.

Example 6

Synthesis of the Exemplified Compounds and their Code

The following compounds (with their code) are generated according to the processes described in the present invention:
Methyl 2-amino-5-(2-(4-methoxyphenyl)ethyl)thiophene-3-carboxylate (TR560)
Methyl 2-amino-5-(2-(phenylethyl)thiophene-3-carboxylate (TR575)
Methyl 2-amino-5-(2-(2-methoxyphenyl)ethyl)thiophene-3-carboxylate (TR567)
Methyl 2-amino-5-(2-(4-methoxy-2-methylphenyl)ethyl) thiophene-3-carboxylate (TR583)
Methyl 2-amino-5-(2-(2-thienyl)ethyl)thiophene-3-carboxylate (TR595)
Ethyl 2-amino-5-(2-(4-methoxyphenyl)ethynyl)thiophene-3-carboxylate (TR530)
Ethyl 2-amino-5-(2-(4-methoxyphenyl)ethyl)thiophene-3-carboxylate (TR532)
Ethyl 2-amino-5-(4-methoxyphenyl)thiophene-3-carboxylate (TR525)
Ethyl 2-amino-5-(2-methoxyphenyl)thiophene-3-carboxylate (TR531)
Ethyl 2-amino-5-(2-(2-methoxyphenyl)ethyl)thiophene-3-carboxylate (TR542)
Ethyl 2-amino-4-ethoxycarbonyl 5-(2-(4-methoxyphenyl)ethyl)thiophene-3-carboxylate (TR547)
Methyl 2-amino-5-(4-methoxyphenyl)thiophene-3-carboxylate (TR572)
Methyl 2-amino-5-((2-methoxyphenyl)thiophene-3-carboxylate (TR581)
2-Amino-3-cyano-5-(4-methoxyphenyl)thiophene (TR582)
Methyl 2-amino-5-(2,5-dimethoxyphenyl)thiophene-3-carboxylate (TR584)
2-Amino-3-cyano-5-(2-(2-methoxyphenyl)ethyl)thiophene (TR585)
2-Amino-3-cyano-5-(2-(4-methoxyphenyl)ethyl)thiophene (TR586)
Ethyl 2-amino-5-(2-(2,5-dimethoxyphenyl)ethyl)thiophene-3-carboxylate (TR587)
2-Amino-3-cyano-5-(2-(phenyl)ethyl)thiophene (TR588)
2-Amino-3-cyano-5-(2-(2,5-dimethoxyphenyl)ethyl) thiophene (TR589)
Ethyl 2-amino-4-ethoxycarbonyl 5-(2-(2,5-dimethoxymethoxyphenyl)ethyl)thiophene-3-carboxylate (TR592)
Methyl 2-amino-5-(2-(2-pyridyl)ethyl)thiophene-3-carboxylate (TR596)
Methyl 2-amino-5-(2-(3-pyridyl)ethyl)thiophene-3-carboxylate (TR597)
Methyl 2-amino-4-methyl-5-(2-(2,5-dimethoxyphenyl) ethyl)thiophene-3-carboxylate (TR599)
Methyl 2-amino-5-(2,5-dimethoxyphenyl)thiophene-3-carboxylate (TR601)
N-Methyl 2-amino-5-(2-(4-methoxyphenyl)ethyl) thiophene-3-carboxamide (TJ19)
2-Amino-5-(2-(4-methoxyphenyl)ethyl)thiophene-3-carboxylate (TJ8)
2-Amino-5-(2-(4-methoxyphenyl)ethyl)thiophene-3-carboxamide (TJ9)
Methyl 2-methylamino-5-(2-(4-methoxyphenyl)ethyl) thiophene-3-carboxylate (TJ6A)
Methyl 2-dimethylamino-5-(2-(4-methoxyphenyl)ethyl) thiophene-3-carboxylate (TJ6B)
Methyl 5-(2-(4-methoxyphenyl)ethyl)thiophene-3-carboxylate (TJ7)
Methyl 2-amino-5-(2-(4-methoxyphenyl)sulfanylmethyl) thiophene-3-carboxylate (TJ22)
Methyl 2-amino-5-(2-(4-methoxyphenyl)oxymethyl) thiophene-3-carboxylate (TJ25)
Methyl 2-amino-5-(2-(4-methoxyphenyl)aminomethyl) thiophene-3-carboxylate (TJ51)
Methyl 2-amino-5-(2-(4-methylphenyl)sulfanylmethyl) thiophene-3-carboxylate (TJ55)
Methyl 2-amino-5-(2-(3-methylphenyl)sulfanylmethyl) thiophene-3-carboxylate (TJ54P)
Methyl 2-amino-5-(2-(phenyl)methylsulfanylmethyl) thiophene-3-carboxylate (TJ57)
Methyl 2-amino-5-(2-(phenyl)sulfanylmethyl)thiophene-3-carboxylate (TJ4)
Methyl 2-phthalimido-5-(2-(4-methoxyphenyl)sulfanylmethyl)thiophene-3-carboxylate (TJ21)
Methyl 2-phthalimido-5-(2-(3-methylphenyl)sulfanylmethyl)thiophene-3-carboxylate (TJ54SM)
Methyl 2-amino-5-benzylthiophene-3-carboxylate (TJ109)
Methyl 2-amino-5-(6-methylhept-5-en-2-yl)thiophene-3-carboxylate (TJ108)
Methyl 2-amino-5-(non-8-enyl)thiophene-3-carboxylate (TJ110)
Methyl 2-amino-5-heptylthiophene-3-carboxylate (TJ114).
Methyl 2-phthalimido-5-(2-(phenyl)sulfanylmethyl) thiophene-3-carboxylate (TJ86)
Methyl 2-phthalimido-5-(2-(4-methoxybenzyl)sulfanylmethyl)thiophene-3-carboxylate (TJ127)
Methyl 2-phthalimido-5-(2-(butyl)sulfanylmethyl) thiophene-3-carboxylate (TJ119)
Methyl 2-amino-5-((naphthalen-2-ylthio)methyl)thiophene-3-carboxylate (TJ113)
Methyl 2-amino-5-((furan-2-ylmethylthio)methyl) thiophene-3-carboxylate (TJ117)
Methyl 2-amino-5-((thiophen-2-ylmethylthio)methyl) thiophene-3-carboxylate (TJ118)
Methyl 2-amino-5-(butylthiomethyl)thiophene-3-carboxylate (TJ125)
Methyl 2-amino-5-((4-methoxyphenylthio)methyl) thiophene-3-carboxylate (TJ130).

2-Amino-5-(4-methoxy-phenyl)-thiophene-3-carboxylic acid ethyl ester (TR525)

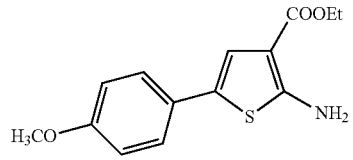 [SMILES: CCOC(=O)c1cc(-c2ccc(OC)cc2)sc1N]

2-Amino-5-(4-methoxy-phenyl)-thiophene-3-carboxylic acid ethyl ester

The crude of reaction was purified by flash chromatography (EtOAc/PE, 2/8) to provide a yellow solid (82% yield) mp 127-129° C. $^1$H NMR (CDCl$_3$, 200 MHz) $\delta_H$ 7.36 (d, 2H, J=8.8 Hz), 7.09 (s, 1H), 6.87 (d, 2H, J=8.8 Hz), 5.93 (bs, 2H), 4.29 (q, 2H, J=7.0 Hz), 3.81 (s, 3H), 1.36 (t, 3H, J=7.0 Hz). [M+1]278.3 (M+H+, C$_{14}$H$_{16}$NO$_3$S requires 278.08).

2-Amino-5-(4-methoxy-phenylethynyl)-thiophene-3-carboxylic acid ethyl ester (TR530)

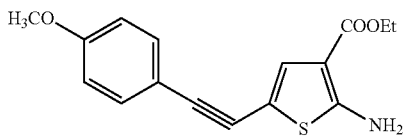 [SMILES: CCOC(=O)c1cc(C#Cc2ccc(OC)cc2)sc1N]

2-Amino-5-(4-methoxy-phenylethynyl)-thiophene-3-carboxylic acid ethyl ester

The crude of reaction was purified by flash chromatography (EtOAc/PE, 2/8) to provide a yellow solid (89% yield) mp 90-92° C. $^1$H NMR (CDCl$_3$, 200 MHz) δ$_H$ 7.36 (d, 2H, J=8.8 Hz), 7.16 (s, 1H), 6.84 (d, 2H, J=8.8 Hz), 6.14 (bs, 2H), 4.26 (q, 2H, J=7.2 Hz), 3.81 (s, 3H), 1.33 (t, 3H, J=7.2 Hz). [M+1]302.02 (M+H+, C$_{16}$H$_{16}$NO$_3$S requires 302.08).

2-Amino-5-(2-methoxy-phenyl)-thiophene-3-carboxylic acid ethyl ester (TR531)

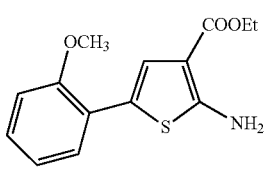 [SMILES: CCOC(=O)c1cc(-c2ccccc2OC)sc1N]

2-Amino-5-(2-methoxy-phenyl)-thiophene-3-carboxylic acid ethyl ester

The crude of reaction was purified by flash chromatography (EtOAc/PE, 2/8) to provide a yellow oil (72% yield). $^1$H NMR (CDCl$_3$, 200 MHz) δ$_H$ 7.53 (dd, 1H, J=7.2 Hz, J=1.4 Hz), 7.41 (s, 1H), 7.17 (m, 1H), 6.95 (m, 2H), 5.99 (bs, 2H), 4.31 (q, 2H, J=7.0 Hz), 3.89 (s, 3H), 1.37 (t, 3H, J=7.0 Hz). [M]277.9 (M+, C14H15NO3S requires 277.08).

2-Amino-5-[2-(4-methoxy-phenyl)-ethyl]-thiophene-3-carboxylic acid ethyl ester (TR532)

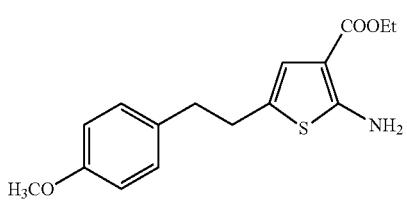 [SMILES: CCOC(=O)c1cc(CCc2ccc(OC)cc2)sc1N]

2-Amino-5-[2-(4-methoxy-phenyl)-ethyl]-thiophene-3-carboxylic acid ethyl ester

The crude of reaction was purified by flash chromatography (EtOAc/PE, 2/8) to provide a colorless oil (81% yield). $^1$H NMR (CDCl$_3$, 200 MHz) δ$_H$ 7.10 (d, 2H, J=8.6 Hz), 6.82 (d, 2H, J=8.6 Hz), 7.64 (s, 1H), 5.81 (bs, 2H), 4.23 (q, 2H, J=7.2 Hz), 3.79 (s, 3H), 2.84 (s, 4H), 1.33 (t, 3H, J=7.2 Hz).

2-Amino-5-[2-(2-methoxy-phenyl)-ethyl]-thiophene-3-carboxylic acid ethyl ester (TR542)

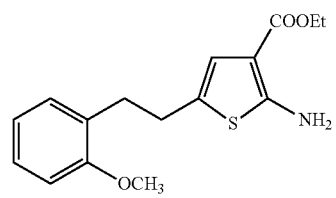 [SMILES: CCOC(=O)c1cc(CCc2ccccc2OC)sc1N]

2-Amino-5-[2-(2-methoxy-phenyl)-ethyl]-thiophene-3-carboxylic acid ethyl ester

The crude of reaction was purified by flash chromatography (EtOAc/PE, 2/8) to provide a colorless oil (100% yield). $^1$H NMR (CDCl$_3$, 200 MHz) δ$_H$ 7.25 (m, 2H), 6.87 (m, 2H), 6.67 (s 1H), 5.80 (bs, 2H), 4.25 (q, 2H, J=7.0 Hz), 3.83 (s, 3H), 2.87 (s, 4H), 1.33 (t, 3H, J=7.0 Hz).

2-Amino-5-[2-(4-methoxy-phenyl)-ethyl]-thiophene-3,4-dicarboxylic acid diethyl ester (TR547)

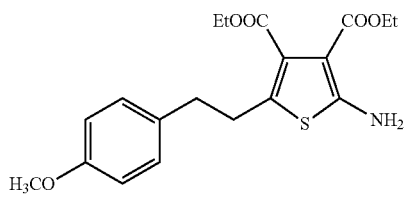 [SMILES: CCOC(=O)c1c(N)sc(CCc2ccc(OC)cc2)c1C(=O)OCC]

2-Amino-5-[2-(4-methoxy-phenyl)-ethyl]-thiophene-3,4-dicarboxylic acid diethyl ester The crude of reaction was purified by flash chromatography (EtOAc/PE, 3/7) to provide a yellow oil (78% yield). H NMR (CDCl$_3$, 200 MHz) δ$_H$ 7.06 (d, 2H, J=8.6 Hz), 6.80 (d, 2H, J=8.6 Hz), 5.92 (bs, 2H), 4.23 (m, 4H), 3.76 (s, 3H), 2.83 (m, 4H) 1.29 (m, 6H).

2-Amino-5-[2-(4-methoxy-phenyl)-ethyl]-thiophene-3-carboxylic acid methyl ester (TR560)

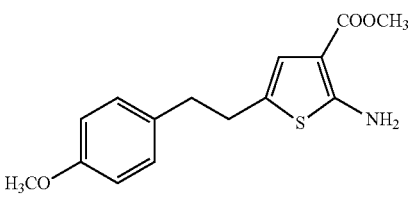 [SMILES: COC(=O)c1cc(CCc2ccc(OC)cc2)sc1N]

2-Amino-5-[2-(4-methoxy-phenyl)-ethyl]-thiophene-3-carboxylic acid methyl ester The crude of reaction was purified by flash chromatography (EtOAc/PE, 2/8) to provide a colorless solid (100% yield). $^1$H NMR (CDCl$_3$, 200 MHz) 67.09 (d, 2H, J=8.6 Hz), 6.82 (d, 2H, J=8.6 Hz), 6.62 (s 1H), 5.81 (bs, 2H), 3.78 (s, 3H), 3.83 (s, 3H), 2.87 (s, 4H).

2-Amino-5-[2-(2-methoxy-phenyl)-ethyl]-thiophene-3-carboxylic acid methyl ester (TR567)

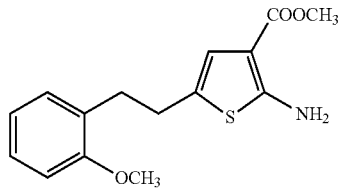 [SMILES: COC(=O)c1cc(CCc2ccccc2OC)sc1N]

2-Amino-5-[2-(2-methoxy-phenyl)-ethyl]-thiophene-3-carboxylic acid methyl ester The crude of reaction was purified by flash chromatography (EtOAc/PE, 3/7) to provide a yellow oil (87% yield). $^1$H NMR (CDCl$_3$, 200 MHz) $\delta_H$ 7.15 (m, 2H), 6.88 (m, 2H), 6.66 (s 1H), 5.83 (bs, 2H), 3.82 (s, 3H), 3.78 (s, 3H), 2.87 (s, 4H).

2-Amino-5-(4-methoxy-phenyl)-thiophene-3-carboxylic acid methyl ester (TR572)

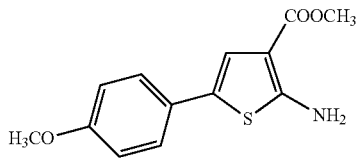 [SMILES: COC(=O)c1cc(-c2ccc(OC)cc2)sc1N]

2-Amino-5-(4-methoxy-phenyl)-thiophene-3-carboxylic acid methyl ester

The crude of reaction was purified by flash chromatography (EtOAc/PE, 2/8) to provide a yellow solid (80% yield). mp 117-119° C. $^1$H NMR (CDCl$_3$, 200 MHz) $\delta_H$ 7.35 (d, 2H, J=8.8 Hz), 7.08 (s, 1H), 6.83 (m, 2H), 5.94 (bs, 2H), 4.29 (q, 2H, J=7.0 Hz), 3.81 (s, 6H). [M+1]263.2 (M+H+, C13H14NO3S requires 263.06).

2-Amino-5-phenethyl-thiophene-3-carboxylic acid methyl ester (TR575)

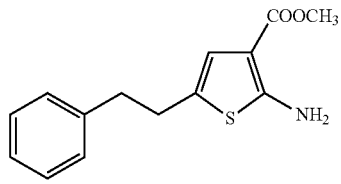

2-Amino-5-phenethyl-thiophene-3-carboxylic acid methyl ester

The crude of reaction was purified by flash chromatography (EtOAc/PE, 3/7) to provide a yellow oil (87% yield). $^1$H NMR (CDCl$_3$, 200 MHz) $\delta_H$ 7.23 (m, 5H), 6.65 (s 1H), 5.83 (bs, 2H), 3.78 (s, 3H), 2.89 (s, 4H).

2-Amino-5-(2-methoxy-phenyl)-thiophene-3-carboxylic acid methyl ester (TR581)

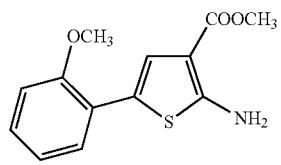 [SMILES: COC(=O)c1cc(-c2ccccc2OC)sc1N]

2-Amino-5-(2-methoxy-phenyl)-thiophene-3-carboxylic acid methyl ester

The crude of reaction was purified by flash chromatography (EtOAc/PE, 2/8) to provide a white solid (67% yield) mp 116-118° C. $^1$H NMR (CDCl$_3$, 200 MHz) $\delta_H$ 7.51 (dd, 1H, J=6.2 Hz, J=1.4 Hz), 7.39 (s, 1H), 7.17 (m, 1H), 6.95 (m, 2H), 5.94 (bs, 2H), 3.91 (s, 3H), 3.83 (s, 3H). [M+1]263.9 (M+, C13H13NO3S requires 263.06).

2-Amino-5-(4-methoxy-phenyl)-thiophene-3-carbonitrile (TR582)

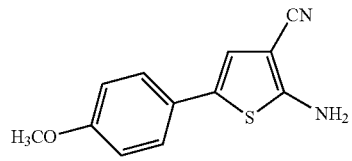 [SMILES: COc1ccc(-c2cc(C#N)c(N)s2)cc1]

2-Amino-5-(4-methoxy-phenyl)-thiophene-3-carbonitrile

The crude of reaction was purified by flash chromatography (EtOAc/PE, 2/8) to provide a white solid (63% yield) mp 204-205° C. $^1$H NMR (CDCl$_3$, 200 MHz) $\delta_H$ 7.33 (d, 2H, J=8.8 Hz), 6.88 (d, 2H, J=8.8 Hz), 6.78 (s, 1H), 4.80 (bs, 2H).

2-Amino-5-[2-(4-methoxy-2-methyl-phenyl)-ethyl]-thiophene-3-carboxylic acid methyl ester (TR583)

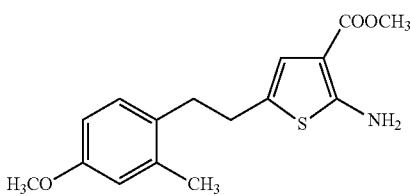 [SMILES: COC(=O)c1cc(CCc2ccc(OC)cc2C)sc1N]

2-Amino-5-[2-(4-methoxy-2-methyl-phenyl)-ethyl]-thiophene-3-carboxylic acid methyl ester The crude of reaction was purified by flash chromatography (EtOAc/PE, 3/7) to provide a yellow solid (71% yield)

mp 110-112° C. $^1$H NMR (CDCl$_3$, 200 MHz) $\delta_H$ 7.06 (d, 1H, J=8.0 Hz), 6.70 (m, 3H), 5.85 (bs, 2H), 3.81 (s, 6H), 2.82 (s, 4H), 2.30 (s, 3H).

2-Amino-5-[2-(2,5-dimethoxy-phenyl)-ethyl]-thiophene-3-carboxylic acid methyl ester (TR584)

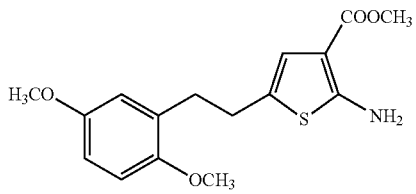

2-Amino-5-[2-(2,5-dimethoxy-phenyl)-ethyl]-thiophene-3-carboxylic acid methyl ester The crude of reaction was purified by flash chromatography (EtOAc/PE, 3/7) to provide a yellow solid mp 107-108° C. (77% yield). $^1$H NMR (CDCl$_3$, 200 MHz) $\delta_H$ 6.71 (m, 4H), 5.80 (bs, 2H), 3.79 (s, 6H), 3.75 (s, 3H), 2.86 (s, 4H).

2-Amino-5-[2-(2-methoxy-phenyl)-ethyl]-thiophene-3-carbonitrile (TR585)

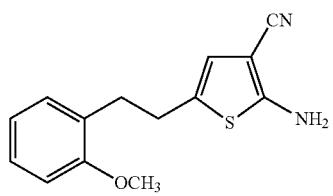 [SMILES: COc1ccccc1CCc1cc(C#N)c(N)s1]

2-Amino-5-[2-(2-methoxy-phenyl)-ethyl]-thiophene-3-carbonitrile

The crude of reaction was purified by flash chromatography (EtOAc/PE, 3/7) to provide a brown oil (51% yield). $^1$H NMR (CDCl$_3$, 200 MHz) $\delta_H$ 7.17 (m, 3H), 6.89 (m, 2H), 6.36 (s 1H), 4.64 (bs, 2H), 3.84 (s, 3H), 2.88 (s, 4H).

2-Amino-5-[2-(4-methoxy-phenyl)-ethyl]-thiophene-3-carbonitrile (TR586)

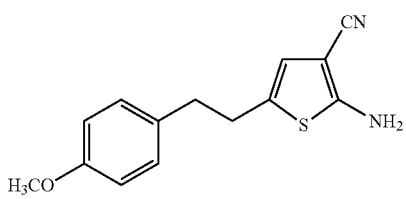 [SMILES: COc1ccc(CCc2cc(C#N)c(N)s2)cc1]

2-Amino-5-[2-(4-methoxy-phenyl)-ethyl]-thiophene-3-carbonitrile

The crude of reaction was purified by flash chromatography (EtOAc/PE, 3/7) to provide a brown solid mp 145-147°

C. (70% yield). $^1$H NMR (CDCl$_3$, 200 MHz) $\delta_H$ 7.08 (d, 2H, J=8.8 Hz), 6.83 (d, 2H, J=8.8 Hz), 6.34 (s 1H), 4.62 (bs, 2H), 3.80 (s, 3H), 2.85 (m, 4H).

2-Amino-5-[2-(2,5-dimethoxy-phenyl)-ethyl]-thiophene-3-carboxylic acid ethyl ester (TR587)

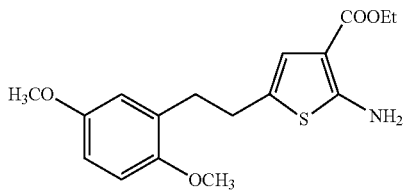 [SMILES: CCOC(=O)c1cc(CCc2cc(OC)ccc2OC)sc1N]

2-Amino-5-[2-(2,5-dimethoxy-phenyl)-ethyl]-thiophene-3-carboxylic acid ethyl ester The crude of reaction was purified by flash chromatography (EtOAc/PE, 3/7) to provide a yellow oil (86% yield). $^1$H NMR (CDCl$_3$, 200 MHz) $\delta_H$ 6.72 (m, 4H), 5.79 (bs, 2H), 4.26 (q, 2H, J=7.2 Hz), 3.79 (s, 3H), 3.75 (s, 3H), 2.86 (s, 3H), 1.34 (t, 3H, J=7.2 Hz).

2-Amino-5-phenethyl-thiophene-3-carbonitrile (TR588)

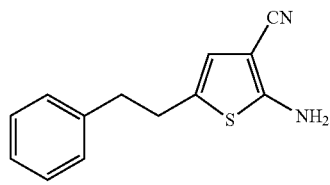 [SMILES: N#Cc1cc(CCc2ccccc2)sc1N]

2-Amino-5-phenethyl-thiophene-3-carbonitrile

The crude of reaction was purified by flash chromatography (EtOAc/PE, 3/7) to provide a orange solid mp 127-129° C. (65% yield). $^1$H NMR (CDCl$_3$, 200 MHz) $\delta_H$ 7.23 (m, 5H), 6.35 (s, 1H), 4.63 (s, 2H), 2.90 (s, 4H).

2-Amino-5-[2-(2,5-dimethoxy-phenyl)-ethyl]-thiophene-3-carbonitrile (TR589)

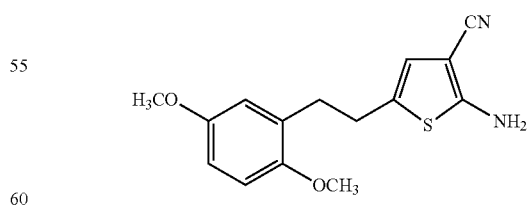

2-Amino-5-[2-(2,5-dimethoxy-phenyl)-ethyl]-thiophene-3-carbonitrile

The crude of reaction was purified by flash chromatography (EtOAc/PE, 3/7) to provide a yellow solid mp 89-91° C.

(70% yield). ¹H NMR (CDCl₃, 200 MHz) δ$_H$ 6.72 (m, 3H), 6.37 (s, 1H), 4.62 (s, 2H), 3.77 (s, 6H), 2.86 (s, 4H).

2-Amino-5-[2-(2,5-dimethoxy-phenyl)-ethyl]-thiophene-3,4-dicarboxylic acid diethyl ester (TR592)

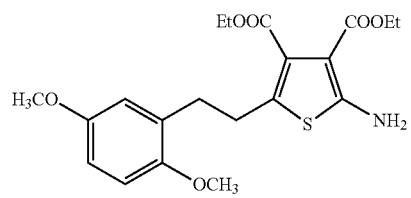

2-Amino-5-[2-(2,5-dimethoxy-phenyl)-ethyl]-thiophene-3,4-dicarboxylic acid diethyl ester The crude of reaction was purified by flash chromatography (EtOAc/PE, 7/3) to provide a yellow oil (81% yield). ¹H NMR (CDCl₃, 200 MHz) δ$_H$ 6.71 (m, 4H), 6.02 (bs, 2H), 4.24 (m, 4H), 3.74 (m, 6H), 2.86 (m, 4H), 1.27 (m, 6H).

2-Amino-5-(2-thiophen-3-yl-ethyl)-thiophene-3-carboxylic acid methyl ester (TR595)

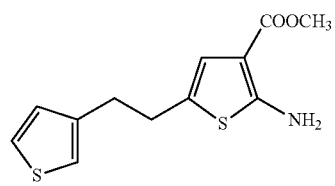 [SMILES: COC(=O)c1cc(CCc2ccsc2)sc1N]

2-Amino-5-(2-thiophen-3-yl-ethyl)-thiophene-3-carboxylic acid methyl ester

The crude of reaction was purified by flash chromatography (EtOAc/PE, 3/7) to provide a yellow oil (79% yield). ¹H NMR (CDCl₃, 200 MHz) δ$_H$ 7.26 (m, 1H), 6.96 (m, 2H), 6.65 (s, 1H), 5.82 (bs, 2H), 3.80 (s, 3H), 2.92 (s, 4H).

2-Amino-5-(2-pyridin-2-yl-ethyl)-thiophene-3-carboxylic acid methyl ester (TR596)

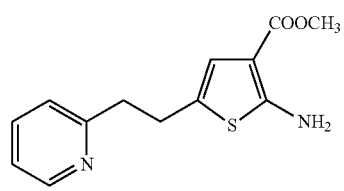 [SMILES: COC(=O)c1cc(CCc2ccccn2)sc1N]

2-Amino-5-(2-pyridin-2-yl-ethyl)-thiophene-3-carboxylic acid methyl ester

The crude of reaction was purified by flash chromatography (EtOAc/PE, 4/6) to provide a yellow oil (87% yield). ¹H NMR (CDCl₃, 200 MHz) δ$_H$ 8.52 (d, 1H, J=3.4 Hz), 7.58 (m, 1H), 7.07 (m, 2H), 6.61 (s, 1H), 5.93 (bs, 2H), 3.76 (s, 3H), 3.03 (s, 4H).

2-Amino-5-(2-pyridin-3-yl-ethyl)-thiophene-3-carboxylic acid methyl ester (TR597)

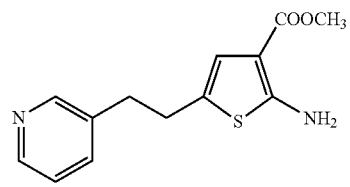 [SMILES: COC(=O)c1cc(CCc2cccnc2)sc1N]

2-Amino-5-(2-pyridin-3-yl-ethyl)-thiophene-3-carboxylic acid methyl ester

The crude of reaction was purified by flash chromatography (EtOAc/PE, 4/6) to provide a white solid, mp 120-122° C. (77% yield). ¹H NMR (CDCl₃, 200 MHz) δ 8.44 (m, 2H), 7.45 (m, 1H), 7.21 (m, 1H), 6.60 (s, 1H), 5.93 (bs, 2H), 3.77 (s, 3H), 2.88 (s, 4H).

2-Amino-5-[2-(2,5-dimethoxy-phenyl)-ethyl]-4-methyl-thiophene-3-carboxylic acid methyl ester (TR599)

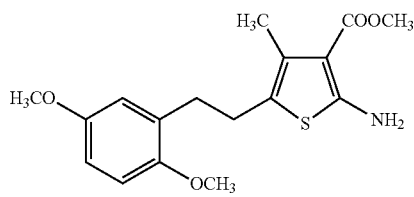 [SMILES: COC(=O)c1c(N)sc(CCc2cc(OC)ccc2OC)c1C]

2-Amino-5-[2-(2,5-dimethoxy-phenyl)-ethyl]-4-methyl-thiophene-3-carboxylic acid methyl ester The crude of reaction was purified by flash chromatography (EtOAc/PE, 3/7) to provide a yellow oil (82% yield). ¹H NMR (CDCl₃, 200 MHz) δ$_H$ 6.72 (m, 3H), 5.93 (bs, 2H), 3.81 (s, 3H), 3.80 (s, 3H), 3.77 (s, 3H), 2.79 (s, 4H), 2.12 (s, 3H).

2-Amino-5-(2,5-dimethoxy-phenyl)-thiophene-3-carboxylic acid methyl ester (TR601)

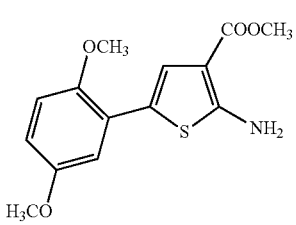 [SMILES: COC(=O)c1cc(-c2cc(OC)ccc2OC)sc1N]

2-Amino-5-(2,5-dimethoxy-phenyl)-thiophene-3-carboxylic acid methyl ester

The crude of reaction was purified by flash chromatography (EtOAc/PE, 2/8) to provide a white solid, mp 204-205° C. (63% yield). $^1$H NMR (CDCl$_3$, 200 MHz) $\delta_H$ 7.39 (s, 1H), 7.08 (d, 1H J=3.0 Hz), 6.9 (s, 1H), 6.86 (s, 1H), 6.76 (m, 1H), 3.84 (s, 9H).

Methyl 2-methylamino-5-(2-(4-methoxyphenyl)ethyl)thiophene-3-carboxylate (TJ6A)

To a solution of 2-aminothiophene TR560 (0.130 g, 0.446 mmol) in THF (2 mL) at 0° C., NaH (0.021 g, 0.932 mmol, 2 equiv) was added followed by the addition of MeI (0.095 g, 0.670 mmol, 1.5 equiv). After stirring the resulting mixture for another 1 h at room temperature (RT), the reaction mixture was added to water (10 mL). CH$_2$Cl$_2$ (10 mL) was added and the organic solution was washed with distilled water (3×10 mL), dried over MgSO$_4$, filtered, and then evaporated to dryness to afford the crude product mixture. Purification by column chromatography (silica, eluent CH$_2$Cl$_2$-heptane 90-10) afforded TJ6A (0.075 g, 55%) as an off-white solid. $^1$H NMR (300 MHz, CDCl$_3$) $\delta_H$ 2.86 (S$_{br}$, 4H); 2.97 (d, 3H); 3.76 (s, 3H); 3.79 (s, 3H); 6.66 (s, 1H); 6.83 (d, 2H); 7.10 (d, 2H).

Methyl 2-di methylamino-5-(2-(4-methoxyphenyl)ethyl)thiophene-3-carboxylate (TJ6B)

To a solution of 2-aminothiophene TR560 (0.05 g, 0.172 mmol) in THF (2 mL) at 0° C., NaH (0.012 g, 0.515 mmol, 3 equiv) was added followed by the addition of MeI (0.073 g, 0.515 mmol, 3 equiv). After stirring the resulting mixture for another 2 h at RT, the reaction mixture was added to water (10 mL). CH$_2$Cl$_2$ (10 mL) was added and the organic solution was washed with distilled water (3×10 mL), dried over MgSO$_4$, filtered, and then evaporated to dryness to afford the crude product mixture. Purification by column chromatography (silica, eluent CH$_2$Cl$_2$-heptane 90-10) afforded TJ6B (0.013 g, 23%) as a semi-solid. $^1$H NMR (300 MHz, CDCl$_3$) $\delta_H$ 2.88 (S$_{br}$, 4H); 2.96 (d, 6H); 3.79 (s, 6H); 6.82 (d, 2H); 6.90 (s, 1H); 7.10 (d, 2H.

Methyl 5-(2-(4-methoxyphenyl)ethyl)thiophene-3-carboxylate (TJ7)

To a solution of 2-aminothiophene TR560 (0.135 g, 0.4641 mmol) in MeOH (2 mL), concentrated sulfuric acid (0.12 mL) and ice (0.5 g) was added. When the mixture was cooled to 0° C., saturated sodium nitrite (0.0383 g; 0.555 mmol) aqueous solution was added keeping the temperature below 5° C. After 30 min, 50% H$_3$PO$_2$ (0.122 g; 0.924 mol) in 0.5 mL of water was added dropwise. After stirring the resulting mixture for another 5 h at RT, the reaction mixture was added to water (10 mL). CH$_2$Cl$_2$ (10 mL) was added and the organic solution was washed with distilled water (3×10 mL), dried over MgSO$_4$, filtered, and then evaporated to dryness to afford the crude product mixture. Purification by column chromatography (silica, eluent CH$_2$Cl$_2$-heptane 95-5) afforded TJ7 (0.035 g, 27%) as a semi-solid. $^1$H NMR (300 MHz, CDCl$_3$) $\delta_H$ 2.91 (t, 2H); 3.07 (t, 2H); 3.78 (s, 3H); 3.84 (s, 3H); 6.82 (d, 2H); 7.14 (d, 2H); 7.19 (s, 1H); 7.87 (s, 1H).

2-Amino-5-(2-(4-methoxyphenyl)ethyl)thiophene-3-carboxylate (TJ8)

To a solution of 2-aminothiophene TR560 (0.210 g, 0.721 mmol) in MeOH (10 mL) at RT, 1 mL of 10N solution of NaOH is added. After stirring the resulting mixture at reflux temperature for 12 h, the reaction mixture was added to water (5 mL) followed by acidification with 2N solution of HCl. Ethyl acetate (10 mL) was added and the organic solution was washed with distilled water (3×10 mL), dried over MgSO$_4$, filtered, and then evaporated to dryness to afford the crude product mixture. Purification by column chromatography (silica, eluent CH$_2$Cl$_2$-MeOH 97-3) afforded TJ8 (0.065 g, 32%) as an off-white solid. $^1$H NMR (300 MHz, CDCl$_3$) $\delta_H$ 2.84 (S$_{br}$, 4H); 3.78 (s, 6H); 6.64 (s, 1H); 6.82 (d, 2H); 7.04 (d, 2H).

2-Amino-5-(2-(4-methoxyphenyl)ethyl)thiophene-3-carboxamide (TJ9)

To a mixture of 4-(4-methoxyphenyl)butanal 6 (0.5 g, 2.805 mmol), 2-cyanoacetamide 7 (0.236 g, 2.805 mmol) and sulfur (0.090 g, 2.805 mmol) in DMF (10 mL), NEt$_3$ (0.851 g, 8.451 mmol, 3 equiv) was added. After stirring the resulting mixture at 60° C. for 30 h, the reaction mixture was added to water (20 mL). Ethyl acetate (20 mL) was added and the organic solution was washed with distilled water (3×20 mL), dried over MgSO$_4$, filtered, and then evaporated to dryness to afford the crude product mixture. Purification by column chromatography (silica, eluent CH$_2$Cl$_2$-ethyl acetate 60-40) afforded TJ9 (0.202 g, 26%) as an off-white solid. $^1$H NMR (300 MHz, CDCl$_3$) $\delta_H$ 2.83 (S$_{br}$, 4H); 3.78 (s, 6H); 5.44 (s, 2H); 6.30 (s, 1H); 6.82 (d, 2H); 7.10 (d, 2H).

N-Methyl 2-amino-5-(2-(4-methoxyphenyl)ethyl)thiophene-3-carboxamide (TJ19)

To a mixture of 4-(4-methoxyphenyl)butanal 6 (0.5 g, 2.805 mmol), 2-cyano-N-methylacetamide 8 (0.275 g, 2.805 mmol) and sulfur (0.090 g, 2.805 mmol) in DMF (10 mL), NEt$_3$ (0.851 g, 8.451 mmol, 3 equiv) was added. After stirring the resulting mixture at 60° C. for 30 hrs, the reaction mixture was added to water (20 mL). Ethyl acetate (20 mL) was added and the organic solution was washed with distilled water (3×20 mL), dried over MgSO$_4$, filtered, and then evaporated to dryness to afford the crude product mixture. Purification by column chromatography (silica, eluent CH$_2$Cl$_2$-ethyl acetate 90-10) afforded TJ19 (0.27 g, 33%) as an off-white solid. $^1$H NMR (300 MHz, CDCl$_3$) $\delta_H$ 2.86 (m, 7H); 3.78 (s, 3H); 5.57 (s, 2H); 6.64 (s, 1H); 6.81 (d, 2H); 7.06 (d, 2H).

Methyl 2-(1,3-dioxoisoindolin-2-yl)-5-methylthiophene-3-carboxylate (14)

To a suspension of compound 13 (5 g, 29.23 mmol) in acetic acid (80 mL) was added phthalic anhydride (6.4 g, 43.24 mmol). After stirring for 30 hrs at reflux, the solvent was evaporated and the residue dissolved in CH$_2$Cl$_2$ (30 mL). The organic solution was washed with a saturated solution of NaHCO$_3$ (50 mL), water (50 mL), dried, and concentrated. Purification by column chromatography (silica, eluent CH$_2$Cl$_2$ afforded 14 (7.7 g, 87%) as an off-white solid. $^1$H NMR (300 MHz, CDCl$_3$) $\delta_H$ 2.51 (s, 3H); 3.69 (s, 3H); 7.19 (s, 1H); 7.80 (m, 2H); 7.87 (m, 2H).

Methyl 5-(bromomethyl)-2-(1,3-dioxoisoindolin-2-yl)thiophene-3-carboxylate (15)

To a solution of protected 2-aminothiophene 14 (2.5 g; 8.33 mmol), N-bromosuccinimide (1.55 g; 8.74 mmol) and benzoyl peroxide (20 mg) in CCl$_4$ (50 ml) was heated at reflux temperature for 20 h under argon atmosphere. The CCl$_4$ was evaporated under reduced pressure and the residue was extracted with dichloromethane (3×50 ml). The combined organic phases were washed with a saturated solution of NaHCO$_3$, dried over magnesium sulfate and the solvent was evaporated under reduced pressure Purification by column chromatography (silica, eluent CH$_2$Cl$_2$) afforded 15 (1.9 g, 60%) as an off-white solid. $^1$H NMR (300 MHz, CDCl$_3$) δ$_H$ 3.72 (s, 3H); 4.66 (s, 2H); 7.51 (s, 1H); 7.84 (m, 2H); 7.97 (m, 2H).

Methyl 2-phthalimido-5-(2-(3-methylphenyl)sulfanylmethyl)thiophene-3-carboxylate (TJ54SM)

To a mixture of (methyl 5-(bromomethyl)-2-(1,3-dioxoisoindolin-2-yl)thiophene-3-carboxylate 15 (0.2 g, 0.5263 mmol) and K$_2$CO$_3$ (0.108 g, 0.7894 mmol, 1.5 equiv) in THF (6 mL) was added 3-methylbenzenethiol (0.065 g, 0.5263 mmol). After stirring the resulting mixture for another 24 h at RT, the reaction mixture was added to water (20 mL). CH$_2$Cl$_2$ (20 mL) was added and the organic solution was washed with distilled water (3×20 mL), dried over MgSO$_4$, filtered, and then evaporated to dryness to afford the crude product mixture. Purification by column chromatography (silica, eluent CH$_2$Cl$_2$) afforded TJ54SM (0.143 g, 64%) as a an off-white solid. $^1$H NMR (300 MHz, CDCl$_3$) δ$_H$ 2.33 (s, 3H); 3.68 (s, 3H); 4.24 (s, 2H); 7.06 (m, 1H); 7.19 (d, 2H); 7.27 (d, 1H); 7.80 (m, 2H); 7.96 (m, 3H).

Methyl 2-phthalimido-5-(2-(4-methoxyphenyl)sulfanylmethyl)thiophene-3-carboxylate (TJ21)

To a mixture of (methyl 5-(bromomethyl)-2-(1,3-dioxoisoindolin-2-yl)thiophene-3-carboxylate (15) (0.2 g, 0.5263 mmol) and K$_2$CO$_3$ (0.108 g, 0.7894 mmol, 1.5 equiv) in THF (6 mL) was added 4-methoxylbenzenethiol (0.073 g, 0.5263 mmol). After stirring the resulting mixture for another 24 h at RT, the reaction mixture was added to water (20 mL). CH$_2$Cl$_2$ (20 mL) was added and the organic solution was washed with distilled water (3×20 mL), dried over MgSO$_4$, filtered, and then evaporated to dryness to afford the crude product mixture. Purification by column chromatography (silica, eluent CH$_2$Cl$_2$) afforded TJ21 (0.167 g, 72%) as a an off-white solid. $^1$H NMR (300 MHz, CDCl$_3$) δ$_H$ 3.68 (s, 3H); 3.79 (s, 3H); 4.13 (s, 2H); 6.85 (d, 2H); 7.18 (s, 1H); 7.37 (d, 2H); 7.81 (m, 2H); 7.96 (m, 2H).

A similar procedure as in the case of TJ54SM and TJ21 were used in the synthesis of TJ86, TJ127 and TJ119.

Methyl 2-phthalimido-5-(2-(phenyl)sulfanylmethyl)thiophene-3-carboxylate (TJ86)

$^1$H NMR (300 MHz, CDCl$_3$) 3.68 (s, 3H); 4.25 (s, 2H); 7.26 (m, 4H); 7.39 (d, 2H); 7.80 (m, 2H); 7.96 (m, 2H).

Methyl 2-phthalimido-5-(2-(4-methoxybenzyl)sulfanylmethyl)thiophene-3-carboxylate (TJ127)

$^1$H NMR (300 MHz, CDCl$_3$) 3.71 (s$_b$, 5H); 3.72 (s, 2H); 3.80 (s, 3H); 6.80 (d, 2H); 7.24 (m, 3H); 7.81 (m, 2H); 7.96 (m, 2H).

Methyl 2-phthalimido-5-(2-(butyl)sulfanylmethyl)thiophene-3-carboxylate (TJ119)

$^1$H NMR (300 MHz, CDCl$_3$) 0.92 (t, 3H); 1.42 (m, 2H); 1.58 (m, 2H); 2.53 (t, 2H); 3.70 (s, 3H); 3.787 (s, 2H); 7.33 (s, 1H); 7.81 (m, 2H); 7.96 (m, 2H).

A similar procedure as in the case of TJ54SM and TJ21 were used in the synthesis of protected analogues of TJ4, TJ22, TJ25, TJ51, TJ57, TJ55 and TJ54P.

General procedure for the synthesis of TJ22, TJ25, TJ51, TJ57, TJ55, TJ54P, TJ113, TJ117, TJ118, TJ125 and TJ130. To a stirred suspension of the compound having general formula 16 in 5 mL EtOH, methyl hydrazine (1.5 equiv) was added. In the case of thiophenol derivative, the reaction mixture was refluxed for 3 h whereas in the case of p-methoxyphenol or p-Anisidine compound, the reaction mixture was stirred at RT for 2 h. The reaction mixture was then added to water (10 mL). CH$_2$Cl$_2$ (10 mL) was added and the organic solution was washed with distilled water (3×10 mL), dried over MgSO$_4$, filtered, and then evaporated to dryness to afford the crude product mixture. Purification by column chromatography (silica, eluent CH$_2$Cl$_2$) afforded corresponding product as a semi-solid.

Methyl 2-amino-5-(2-(phenyl)sulfanylmethyl)thiophene-3-carboxylate (TJ4)

$^1$H NMR (300 MHz, CDCl$_3$) δ$_H$ 3.76 (s, 3H); 4.07 (s, 2H); 5.89 (s, 2H); 6.71 (s, 1H); 67.29 (m, 2H); 7.32 (d, 2H).

Methyl 2-amino-5-(2-(4-methoxyphenyl)sulfanylmethyl)thiophene-3-carboxylate (TJ22)

$^1$H NMR (300 MHz, CDCl$_3$) δ$_H$ 3.65 (s, 3H); 3.79 (s, 3H); 3.96 (s, 2H); 5.85 (s, 2H); 6.62 (s, 1H); 6.82 (d, 2H); 7.32 (d, 2H).

Methyl 2-amino-5-(2-(4-methoxyphenyl)aminomethyl)thiophene-3-carboxylate (TJ51)

$^1$H NMR (300 MHz, CDCl$_3$) δ$_H$ 3.74 (s, 3H); 3.79 (s, 3H); 4.22 (s, 2H); 5.90 (s, 2H); 6.63 (d, 2H); 6.78 (d, 2H); 6.84 (s, 1H).

Methyl 2-amino-5-(2-(phenyl)methylsulfanylmethyl)thiophene-3-carboxylate (TJ57)

$^1$H NMR (300 MHz, CDCl$_3$) δ$_H$ 3.57 (d, 2H); 3.66 (s, 2H); 3.80 (s, 3H); 5.93 (s, 2H); 6.74 (s, 1H); 7.28 (m, 5H).

Methyl 2-amino-5-(2-(4-methyl phenyl)sulfanyl methyl)thiophene-3-carboxylate (TJ55)

$^1$H NMR (300 MHz, CDCl$_3$) δ$_H$ 2.31 (s, 3H); 376 (s, 3H); 4.03 (s, 2H); 5.88 (s, 2H); 6.68 (s, 1H); 7.07 (d, 2H); 7.24 (d, 2H).

Methyl 2-amino-5-(2-(3-methyl phenyl)sulfanyl methyl)thiophene-3-carboxylate (TJ54P)

$^1$H NMR (300 MHz, CDCl$_3$) δ$_H$ 2.30 (s, 3H); 3.76 (s, 3H); 4.07 (s, 2H); 5.89 (s, 2H); 6.72 (s, 1H); 7.02 (d, 1H); 7.15 (m, 3H).

Methyl 2-amino-5-((naphthalen-2-ylthio)methyl)thiophene-3-carboxylate (TJ113)

$^1$H NMR (300 MHz, CDCl$_3$) δ$_H$ 3.71 (s, 3H); 4.16 (s, 2H); 5.88 (s, 2H); 6.73 (s, 1H); 7.42 (m, 3H); 7.76 (d, 2H).

Methyl 2-amino-5-((furan-2-ylmethylthio)methyl) thiophene-3-carboxylate (TJ117)

$^1$H NMR (300 MHz, CDCl$_3$) $\delta_H$ 3.65 (s, 2H); 3.67 (s, 2H); 3.79 (s, 3H); 5.98 (s, 2H); 6.16 (d, 1H); 6.31 (t, 1H); 6.79 (s, 1H); 7.31 (d, 1H).

Methyl 2-amino-5-((thiophen-2-ylmethylthio)methyl)thiophene-3-carboxylate (TJ118)

$^1$H NMR (300 MHz, CDCl$_3$) $\delta_H$ 3.65 (s, 2H); 3.67 (s, 2H); 3.79 (s, 3H); 3.85 (s, 2H); 5.95 (s, 2H); 6.76 (S$_b$, 1H); 6.91 (S$_b$, 2H); 7.21 (S$_b$, 1H).

Methyl 2-amino-5-(butylthiomethyl)thiophene-3-carboxylate (TJ125)

$^1$H NMR (300 MHz, CDCl$_3$) 0.87 (t, 3H); 1.39 (m, 2H); 1.54 (m, 2H); 2.46 (t, 2H); 3.68 (s, 2H); 3.78 (s, 3H); 5.92 (s, 2H); 6.75 (s, 1H).

Methyl 2-amino-5-((4-methoxyphenylthio)methyl) thiophene-3-carboxylate (TJ130)

$^1$H NMR (300 MHz, CDCl$_3$) 3.58 (s, 2H); 3.61 (s, 2H); 3.79 (s, 6H); 5.94 (s, 2H); 6.73 (s, 1H); 6.84 (d, 2H); 7.20 (d, 2H).

Synthetic route to compounds having general formula 23 is described in Scheme 4 (Example 2), wherein for general formula 23 the values for the following compounds are:
TJ21, R$_1$=OMe, R$_2$=H, X=S, 89%
TJ55, R$_1$=Me, R$_2$=H, X=S, 82%
TJ54P, R$_1$=H, R$_2$=M, X=S, 93%
TJ4, R$_1$=H, R$_2$=H, X=CH$_2$S, 86%
TJ25, R$_1$=OMe, R$_2$=H, X=O, 1%
TJ51, R$_1$=OMe, R$_2$=H, X=NH, 3%

Methyl 2-amino-5-benzylthiophene-3-carboxylate (TJ109)

To a mixture of 3-henylpropanal (0.261 g, 1.95 mmol), methyl cyanoacetate (0.192 g, 1.95 mmol) and sulfur (0.062 g, 1.95 mmol) in methanol (10 mL), NEt$_3$ (0.196 g, 1.95 mmol) was added. After stirring the resulting mixture at reflux for 15 hrs, the reaction mixture was added to water (20 mL). Ethyl acetate (20 mL) was added and the organic solution was washed with distilled water (3×20 mL), dried over MgSO$_4$, filtered, and then evaporated to dryness to afford the crude product mixture. Purification by column chromatography (silica, eluent heptane-ethyl acetate 50-50) afforded TJ109 (0.385 g, 80%) as an off-white solid. $^1$H NMR (300 MHz, CDCl$_3$) $\delta_H$ 3.77 (s, 3H); 3.89 (s, 2H); 5.78 (s, 2H); 6.66 (s, 1H); 7.27 (m, 5H).

Methyl 2-amino-5-(6-methylhept-5-en-2-yl) thiophene-3-carboxylate (TJ108)

To a mixture of citronellal 0.3 g, 1.95 mmol), methyl cyanoacetate (0.192 g, 1.95 mmol) and sulfur (0.062 g, 1.95 mmol) in methanol (10 mL), NEt$_3$ (0.196 g, 1.95 mmol) was added. After stirring the resulting mixture at reflux for 15 hrs, the reaction mixture was added to water (20 mL). Ethyl acetate (20 mL) was added and the organic solution was washed with distilled water (3×20 mL), dried over MgSO$_4$, filtered, and then evaporated to dryness to afford the crude product mixture. Purification by column chromatography (silica, eluent heptane-ethyl acetate 50-50) afforded TJ108 (0.38 g, 73%) as an off-white solid. $^1$H NMR (300 MHz, CDCl$_3$) $\delta_H$ 1.22 (d, 3H); 1.52 (m, 2H); 1.56 (s, 3H); 1.67 (s, 3H); 1.97 (q, 2H); 2.74 (m, 1H); 3.78 (s, 3H); 5.08 (t, 1H); 5.80 (s, 2H); 6.61 (s, 1H).

Methyl 2-amino-5-(non-8-enyl)thiophene-3-carboxylate (TJ110)

To a mixture of undec-10-enal (0.326 g, 1.95 mmol), methyl cyanoacetate (0.192 g, 1.95 mmol) and sulfur (0.062 g, 1.95 mmol) in methanol (10 mL), NEt$_3$ (0.196 g, 1.95 mmol) was added. After stirring the resulting mixture at reflux for 15 hrs, the reaction mixture was added to water (20 mL). Ethyl acetate (20 mL) was added and the organic solution was washed with distilled water (3×20 mL), dried over MgSO$_4$, filtered, and then evaporated to dryness to afford the crude product mixture. Purification by column chromatography (silica, eluent heptane-ethyl acetate 50-50) afforded TJ110 (0.465 g, 85%) as an off-white solid. $^1$H NMR (300 MHz, CDCl$_3$) $\delta_H$ 1.30 (m, 8H); 1.58 (m, 2H); 2.04 (q, 2H); 2.56 (t, 2H); 3.78 (s, 3H); 5.49 (m, 2H); 5.79 (m, 3H); 6.60 (s, 1H).

Methyl 2-amino-5-heptylthiophene-3-carboxylate (TJ114)

To a mixture of nonanal (0.275 g, 1.95 mmol), methyl cyanoacetate (0.192 g, 1.95 mmol) and sulfur (0.062 g, 1.95 mmol) in methanol (10 mL), NEt$_3$ (0.196 g, 1.95 mmol) was added. After stirring the resulting mixture at reflux for 15 hrs, the reaction mixture was added to water (20 mL). Ethyl acetate (20 mL) was added and the organic solution was washed with distilled water (3×20 mL), dried over MgSO$_4$, filtered, and then evaporated to dryness to afford the crude product mixture. Purification by column chromatography (silica, eluent heptane-ethyl acetate 50-50) afforded TJ114 (0.365 g, 73%) as an off-white solid. $^1$H NMR (300 MHz, CDCl$_3$) $\delta_H$ 0.89 (t, 3H); 1.28 (m, 8H); 1.57 (q, 2H); 2.56 (t, 2H); 3.78 (s, 3H); 5.77 (s$_b$, 2H); 6.60 (s, $^1$H).

Example 7

Synthesis of Exemplified Compounds and their Activity

Synthesis

The following compounds (with their code) are generated according to the processes described in the present invention:

General procedure for the synthesis of Methyl 2-amino-5-alkylthiophene-3-carboxylate derivatives (TJ15 to TJ161).

To a mixture of the corresponding aliphatic aldehyde (1.95 mmol), methyl cyanoacetate (0.192 g, 1.95 mmol) and sulfur (0.062 g, 1.95 mmol) in methanol (10 mL), NEt$_3$ (0.196 g, 1.95 mmol) was added. After stirring the resulting mixture at reflux for 15 h, the reaction mixture was added to water (20 mL). Ethyl acetate (40 mL) was added and the organic solution was washed with distilled water (3×20 mL), dried over MgSO$_4$, filtered, and then evaporated to dryness to afford the crude product mixture. Purification by column chromatography (silica, eluent heptane-ethyl acetate 50-50) afforded the corresponding methyl 2-amino-5-alkyllthiophene-3-carboxylate derivative (70%-91%).

Methyl 2-amino-5-methylthiophene-3-carboxylate (TJ15)

$^1$H NMR (300 MHz, CDCl$_3$) δ$_H$ 2.45 (s, 3H); 3.71 (s, 3H); 5.89 (s, 2H); 7.20 (s, 1H).

Methyl 2-amino-5-ethylthiophene-3-carboxylate (TJ157)

$^1$H NMR (300 MHz, CDCl$_3$) δ$_H$ 1.22 (t, 3H); 2.60 (q, 2H); 3.79 (s, 3H); 5.82 (s$_b$, 2H); 6.61 (s, 1H).

Methyl 2-amino-5-propylthiophene-3-carboxylate (TJ190)

$^1$H NMR (300 MHz, CDCl$_3$) δ$_H$ 0.95 (t, 3H); 1.59 (m, 2H); 2.55 (t, 2H); 3.79 (s, 3H); 5.71 (s$_b$, 2H); 6.61 (s, 1H).

Methyl 2-amino-5-(3-chloropropyl)thiophene-3-carboxylate (TJ168D)

$^1$H NMR (300 MHz, CDCl$_3$) δ$_H$ 2.35 (m, 2H); 2.76 (t, 2H); 3.79 (t, 3H); 4.09 (t, 2H); 5.84 (s$_b$, 2H); 6.67 (s, 1H).

Methyl 2-amino-5-butylthiophene-3-carboxylate (TJ154)

$^1$H NMR (300 MHz, CDCl$_3$) δ$_H$ 0.91 (t, 3H); 1.36 (m, 2H); 1.56 (m, 2H); 2.57 (t, 2H); 3.78 (s, 3H); 5.80 (s$_b$, 2H); 6.61 (s, 1H).

Methyl 2-amino-5-pentylthiophene-3-carboxylate (TJ156)

$^1$H NMR (300 MHz, CDCl$_3$) δ$_H$ 0.89 (t, 3H); 1.31 (m, 4H); 1.57 (m, 2H); 2.56 (t, 2H); 3.78 (s, 3H); 5.80 (s$_b$, 2H); 6.60 (s, 1H).

Methyl 2-amino-5-hexylthiophene-3-carboxylate (TJ155)

$^1$H NMR (300 MHz, CDCl$_3$) δ$_H$ 0.88 (t, 3H); 1.29 (m, 4H); 1.56 (m, 2H); 2.56 (t, 2H); 3.78 (s, 3H); 5.79 (s$_b$, 2H); 6.60 (s, 1H).

Methyl 2-amino-5-heptylthiophene-3-carboxylate (TJ191 or TJ114)

$^1$H NMR (300 MHz, CDCl$_3$) δ$_H$ 0.89 (t, 3H); 1.28 (m, 8H); 1.57 (m, 2H); 2.56 (t, 2H); 3.78 (s, 3H); 5.77 (S$_b$, 2H); 6.60 (s, 1H).

Methyl 2-amino-5-octylthiophene-3-carboxylate (TJ144)

$^1$H NMR (300 MHz, CDCl$_3$) δ$_H$ 0.88 (t, 3H); 1.27 (m, 10H); 1.55 (m, 2H); 2.56 (t, 2H); 3.79 (s, 3H); 5.77 (s$_b$, 2H); 6.60 (s, 1H).

2-amino-5-(non-8-enyl)thiophene-3-carbonitrile (TJ145)

$^1$H NMR (300 MHz, CDCl$_3$) δ$_H$ 1.30 (m, 8H); 1.56 (m, 2H); 2.04 (q, 2H); 2.57 (t, 2H); 4.62 (m, 2H); 4.95 (m, 2H); 5.82 (m, 1H); 6.36 (s, 1H).

Methyl 2-amino-4-methyl-5-octylthiophene-3-carboxylate (TJ163)

1H NMR (300 MHz, CDCl$_3$) δ$_H$ 0.88 (t, 3H); 1.26 (m, 10H); 1.50 (m, 2H); 2.16 (s, 3H); 2.53 (t, 2H); 3.80 (s, 3H); 5.91 (s$_b$, 2H).

Methyl 2-amino-5-nonylthiophene-3-carboxylate (TJ198)

$^1$H NMR (300 MHz, CDCl$_3$) δ$_H$ 0.88 (t, 3H); 1.27 (m, 12H); 1.56 (m, 2H); 2.56 (t, 2H); 3.78 (s, 3H); 5.80 (s$_b$, 2H); 6.60 (s, 1H).

Methyl 2-amino-5-decylthiophene-3-carboxylate (TJ158)

$^1$H NMR (300 MHz, CDCl$_3$) δ$_H$ 0.88 (t, 3H); 1.26 (m, 14H); 1.56 (m, 2H); 2.56 (t, 2H); 3.78 (s, 3H); 5.78 (s$_b$, 2H); 6.60 (s, 1H).

Methyl 2-amino-5-dodecylthiophene-3-carboxylate (TJ159)

$^1$H NMR (300 MHz, CDCl$_3$) δ$_H$ 0.88 (t, 3H); 1.26 (m, 18H); 1.56 (m, 2H); 2.56 (t, 2H); 3.79 (s, 3H); 5.78 (s$_b$, 2H); 6.60 (s, 1H).

Methyl 2-amino-5-tridecylthiophene-3-carboxylate (TJ160)

$^1$H NMR (300 MHz, CDCl$_3$) δ$_H$ 0.88 (t, 3H); 1.26 (m, 20H); 1.56 (m, 2H); 2.56 (t, 2H); 3.79 (s, 3H); 5.78 (s$_b$, 2H); 6.60 (s, 1H).

Methyl 2-amino-5-tetradecylthiophene-3-carboxylate (TJ188)

$^1$H NMR (300 MHz, CDCl$_3$) δ$_H$ 0.88 (t, 3H); 1.25 (m, 22H); 1.56 (m, 2H); 2.56 (t, 2H); 3.78 (s, 3H); 5.79 (s$_b$, 2H); 6.60 (s, 1H).

Methyl 2-amino-5-pentadecylthiophene-3-carboxylate (TJ153)

$^1$H NMR (300 MHz, CDCl$_3$) δ$_H$ 0.88 (t, 3H); 1.25 (m, 24H); 1.56 (m, 2H); 2.56 (t, 2H); 3.78 (s, 3H); 5.80 (S$_b$, 2H); 6.60 (s, 1H).

Methyl 2-amino-5-hexadecylthiophene-3-carboxylate (TJ161)

$^1$H NMR (300 MHz, CDCl$_3$) δ$_H$ 0.88 (t, 3H); 1.25 (m, 26H); 1.56 (m, 2H); 2.56 (t, 2H); 3.78 (s, 3H); 5.80 (s$_b$, 2H); 6.60 (s, 1H).

General Procedure for the Synthesis of 5-Alkyl or Aryl Thiomethyl-Substituted 2-Amino-3-Carboxymethylthiophene Derivatives (TJ125 to TJ117).

To a stirred suspension of the compound having general formula 16 in 5 mL EtOH, methyl hydrazine (1.5 equiv) was added. After stirring the resulting mixture at reflux for 6 h, the reaction mixture was added to water (20 mL). CH$_2$Cl$_2$ (10 mL) was added and the organic solution was washed with distilled water (3×10 mL), dried over MgSO$_4$, filtered, and

Methyl 2-amino-5-(pentylthiomethyl)thiophene-3-carboxylate (TJ172)

$^1$H NMR (300 MHz, CDCl$_3$) 0.89 (t, 3H); 1.31 (m, 4H);) 1.56 (m, 2H) 2.45 (t, 2H); 3.69 (s, 2H); 3.79 (s, 3H); 5.92 (s$_b$, 2H); 6.75 (s, 1H).

Methyl 2-amino-5-(isopentylthiomethyl)thiophene-3-carboxylate (TJ173)

$^1$H NMR (300 MHz, CDCl$_3$) 0.80 (d, 6H) 1.39 (m, 2H) 1.53 (m, 1H) 2.39 (t, 2H); 3.61 (s, 2H); 3.72 (s, 3H); 5.84 (s$_b$, 2H); 6.68 (s, 1H).

Methyl 2-amino-5-(hexylthiomethyl)thiophene-3-carboxylate (TJ171)

$^1$H NMR (300 MHz, CDCl$_3$) 0.88 (t, 3H); 1.26 (m, 6H) 1.55 (m, 2H) 2.46 (t, 2H); 3.69 (s, 2H); 3.79 (s, 3H); 5.90 (s$_b$, 2H); 6.75 (s, 1H).

Methyl 2-amino-5-(heptylthiomethyl)thiophene-3-carboxylate (TJ177)

$^1$H NMR (300 MHz, CDCl$_3$) 0.88 (t, 3H); 1.26 (m, 8H) 1.55 (m, 2H) 2.46 (t, 2H); 3.69 (s, 2H); 3.79 (s, 3H); 5.92 (s$_b$, 2H); 6.75 (s, 1H).

Methyl 2-amino-5-(octylthiomethyl)thiophene-3-carboxylate (TJ178)

$^1$H NMR (300 MHz, CDCl$_3$) 0.88 (t, 3H); 1.26 (m, 10H) 1.55 (m, 2H) 2.45 (t, 2H); 3.69 (s, 2H); 3.79 (s, 3H); 5.92 (s$_b$, 2H); 6.75 (s, 1H).

Methyl 2-amino-5-(cyclopentylthiomethyl)thiophene-3-carboxylate (TJ179)

$^1$H NMR (300 MHz, CDCl$_3$) δ$_H$ 1.53 (m, 4H); 1.72 (m, 2H); 1.96 (m, 2H); 3.03 (m, 1H); 3.71 (s, 2H); 3.79 (s, 3H); 5.93 (s$_b$, 4H); 6.75 (s, 1H).

Methyl 2-amino-5-(cyclohexylthiomethyl)thiophene-3-carboxylate (D8)

1H NMR (300 MHz, CDCl3) δH 1.27 (m, 2H); 1.29 (m, 2H); 1.59 (m, 2H); 1.74 (m, 2H); 1.92 (m, 2H); 2.62 (m, 1H); 3.72 (s, 2H); 3.79 (s, 3H); 5.89 (S$_b$, 2H); 6.75 (s, 1H).

Methyl 2-amino-5-(o-tolylthiomethyl)thiophene-3-carboxylate (D3)

$^1$H NMR (300 MHz, CDCl$_3$) δ$_H$ 2.37 (s, 3H); 3.76 (s, 3H); 4.05 (s, 2H); 5.89 (S$_b$, 2H); 6.73 (s, 1H); 7.14 (m, 3H); 7.29 (m, 1H).

Methyl 2-amino-5-((2-aminophenylthio)methyl) thiophene-3-carboxylate (TJ122)

$^1$H NMR (300 MHz, CDCl$_3$) δ$_H$ 3.74 (s, 3H); 3.89 (s, 2H); 4.33 (S$_b$, 2H); 5.89 (S$_b$, 2H); 6.59 (s, 1H); 6.67 (m, 2H); 7.17 (t, 1H), 7.27 (d, 1H).

Methyl 2-amino-5-((2-methoxyphenylthio)methyl) thiophene-3-carboxylate (D6)

$^1$H NMR (300 MHz, CDCl$_3$) δ$_H$ 3.75 (s, 3H); 3.89 (s, 3H); 4.07 (S$_b$, 2H); 5.87 (s, 2H); 6.71 (s, 1H); 6.87 (m, 2H); 7.22 (m, 1H); 7.29 (m, 1H).

Methyl 2-amino-5-((2-(methoxycarbonyl)phenylthio)methyl)thiophene-3-carboxylate (D7)

$^1$H NMR (300 MHz, CDCl$_3$) δ$_H$ 3.78 (s, 3H); 3.92 (s, 3H); 4.15 (s, 2H); 5.88 (s, 2H); 6.89 (s, 1H); 7.18 (m, 1H); 7.39 (m, 2H); 7.92 (m, 1H).

3-((5-amino-4-(methoxycarbonyl)thiophen-2-yl) methylthio)benzoic acid (TJ53)

$^1$H NMR (300 MHz, CDCl$_3$) δ$_H$ 3.68 (s, 3H); 412 (s, 3H); 6.07 (s, 2H); 6.71 (s, 1H); 7.40 (t, 1H); 779 (d, $^1$H); 7.92 (m, 1H), 8.09 (s, 1H).

Methyl 2-amino-5-((4-fluorophenylthio)methyl) thiophene-3-carboxylate (D10)

$^1$H NMR (300 MHz, CDCl$_3$) δ$_H$ 3.76 (s, 3H); 4.00 (s, 2H); 5.92 (s, 2H); 6.62 (s, 1H); 6.97 (m, 2H); 7.32 (m, 2H).

Methyl 2-amino-5-((4-chlorophenylthio)methyl) thiophene-3-carboxylate (D4)

$^1$H NMR (300 MHz, CDCl$_3$) δ$_H$ 3.77 (s, 3H); 4.04 (s, 2H); 5.91 (s, 2H); 6.69 (s, 1H); 7.25 (m, 4H).

Methyl 2-amino-5-((4-nitrophenylthio)methyl) thiophene-3-carboxylate (TJ126)

$^1$H NMR (300 MHz, CDCl$_3$) δ$_H$ 3.78 (s, 3H); 4.22 (s, 2H); 5.95 (s, 2H); 6.86 (s, 1H); 7.36 (d, 2H); 8.12 (d, 2H).

Methyl 2-amino-5-((4-methylphenylthio)methyl) thiophene-3-carboxylate (TJ55)

$^1$H NMR (300 MHz, CDCl$_3$) δ$_H$ 2.31 (s, 3H); 3.76 (s, 3H); 4.03 (s, 2H); 5.88 (s, 2H); 6.68 (s, 1H); 7.07 (d, 2H); 7.24 (d, 2H).

Methyl 2-amino-5-((4-ethylphenylthio)methyl) thiophene-3-carboxylate (TJ185)

$^1$H NMR (300 MHz, CDCl$_3$) δ$_H$ 1.20 (t, 3H); 2.60 (q, 2H); 3.75 (s, 3H); 4.03 (s, 2H); 5.89 (s, 2H); 6.67 (s, 1H); 7.12 (d, 2H); 7.25 (d, 2H).

Methyl 2-amino-5-((4-isopropylphenylthio)methyl) thiophene-3-carboxylate (TJ186)

$^1$H NMR (300 MHz, CDCl$_3$) δ$_H$ 1.22 (d, 6H); 2.87 (q, 1H); 3.75 (s, 3H); 4.04 (s, 2H); 5.89 (s, 2H); 6.67 (s, 1H); 7.13 (d, 2H); 7.27 (d, 2H).

Methyl 2-amino-5-(phenethylthiomethyl)thiophene-3-carboxylate (TJ187)

$^1$H NMR (300 MHz, CDCl$_3$) δ$_H$ 2.71 (t, 2H); 2.83 (t, 2H); 3.67 (s, 2H); 3.79 (s, 2H); 5.93 (s, 2H); 6.75 (s, 1H); 7.18 (m, 5H).

Methyl 2-amino-5-((biphenyl-4-ylthio)methyl)thiophene-3-carboxylate (TJ184)

$^1$H NMR (300 MHz, CDCl$_3$) 3.75 (s, 3H); 4.10 (s, 2H); 5.91 (s, 2H); 6.73 (s, 1H); 7.04 (m, 5H); 7.52 (m, 4H).

Methyl 2-amino-5-((pyridin-4-ylthio)methyl)thiophene-3-carboxylate (TJ129)

$^1$H NMR (300 MHz, CDCl$_3$) δ$_H$ 3.78 (s, 3H); 4.19 (s, 2H); 6.06 (s, 2H); 6.89 (s, 1H); 7.15 (d, 2H); 8.41 (d, 2H).
General Procedure for the Synthesis of TJ170 and TJ169.

To a mixture of TJ168D (50 mg) and K$_2$CO$_3$ (1.0 equiv) in THF (4 mL) was added 4-methoxybenzenethiol or cyclohexanethiol (1.0 equiv). After stirring the resulting mixture for another 24 h at 45° C., the reaction mixture was added to water (10 mL). CH$_2$Cl$_2$ (15 mL) was added and the organic solution was washed with distilled water (3×15 mL), dried over MgSO$_4$, filtered, and then evaporated to dryness to afford the crude product mixture. Purification by column chromatography (silica, eluent CH$_2$Cl$_2$) afforded TJ170 or TJ169 as a semi solid.

Methyl 2-amino-5-(3-(cyclohexylthio)propyl)thiophene-3-carboxylate (TJ170)

$^1$H NMR (300 MHz, CDCl$_3$) δ$_H$ 1.25 (m, 12H); 1.56 (q, 3H); 2.54 (t, 2H); 3.78 (s, 3H); 5.77 (s, 2H); 6.60 (s, 1H).

Methyl 2-amino-5-(3-(4-methoxyphenylthio)propyl)thiophene-3-carboxylate (TJ169)

$^1$H NMR (300 MHz, CDCl$_3$) δ$_H$ 1.82 (m, 2H); 2.70 (t, 2H); 2.83 (t, 2H); 3.78 (s, 3H); 3.79 (s, 3H); 5.79 (s, 2H); 6.60 (s, 1H), 6.83 (d, 2H), 7.34 (d, 2H).
Activity and Tumor Cell Selectivity:

The activity and tumor cell selectivity of the compounds are shown in Table 6 and Table 7.

TABLE 6

Tumor cell selectivity of 5-alkyl-substituted 2-aminothiophenes

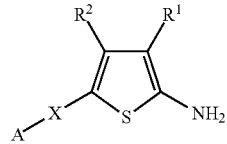

| Code | —X—A | R$^1$ | R$^2$ | IC$_{50}$ (μM) CEM | HeLa | Ratio |
|---|---|---|---|---|---|---|
| TJ15 | —CH$_3$ | —COOMe | —H | >250 | >250 | >1< |
| TJ157 | —CH$_2$CH$_3$ | —COOMe | —H | 175 | 180 | 1 |
| TJ190 | —(CH$_2$)$_2$CH$_3$ | —COOMe | —H | 6.9 | 61 | 9 |
| TJ168D | —(CH$_2$)$_2$CH$_2$Cl | —COOMe | —H | 26 | 150 | 6 |
| TJ154 | —(CH$_2$)$_3$CH$_3$ | —COOMe | —H | 4.6 | 77 | 17 |
| TJ156 | —(CH$_2$)$_4$CH$_3$ | —COOMe | —H | 0.98 | 83 | 85 |
| TJ155 | —(CH$_2$)$_5$CH$_3$ | —COOMe | —H | 0.20 | 73 | 365 |
| TJ191 | —(CH$_2$)$_6$CH$_3$ | —COOMe | —H | 0.13 | 81 | 623 |
| TJ144 | —(CH$_2$)$_7$CH$_3$ | —COOMe | —H | 0.27 | 86 | 319 |
| TJ108 | —CH(CH$_3$)CH$_2$CH$_2$CH=C(CH$_3$)$_2$ | —COOMe | —H | 13 | 97 | 7 |
| TJ145 | —(CH$_2$)$_7$CH=CH$_2$ | —C≡N | —H | 0.19 | 60 | 111 |
| TJ110 | —(CH$_2$)$_7$CH=CH$_2$ | —COOMe | —H | 0.28 | 21 | 214 |
| TJ163 | —(CH$_2$)$_7$CH$_3$ | —COOMe | —CH$_3$ | 16 | 84 | 5 |
| TJ198 | —(CH$_2$)$_8$CH$_3$ | —COOMe | —H | 0.20 | 171 | 855 |
| TJ158 | —(CH$_2$)$_9$CH$_3$ | —COOMe | —H | 0.33 | 68 | 206 |
| TJ159 | —(CH$_2$)$_{11}$CH$_3$ | —COOMe | —H | 0.56 | 187 | 334 |
| TJ160 | —(CH$_2$)$_{12}$CH$_3$ | —COOMe | —H | 1.3 | >250 | >192 |
| TJ188 | —(CH$_2$)$_{13}$CH$_3$ | —COOMe | —H | 1.0 | >250 | >250 |
| TJ153 | —(CH$_2$)$_{14}$CH$_3$ | —COOMe | —H | 6.1 | >250 | >41 |
| TJ161- | —(CH$_2$)$_{15}$CH$_3$ | —COOMe | —H | 6.4 | >250 | >39 |
| TJ125 | —(CH$_2$S)(CH$_2$)$_3$CH$_3$ | —COOMe | —H | 0.52 | 81 | 156 |
| TJ172 | —(CH$_2$S)(CH$_2$)$_4$CH$_3$ | —COOMe | —H | 0.83 | 73 | 88 |
| TJ173 | —(CH$_2$S)(CH$_2$)$_2$CH(CH$_3$)$_2$ | —COOMe | —H | 0.91 | 71 | 78 |
| TJ171 | —(CH$_2$S)(CH$_2$)$_5$CH$_3$ | —COOMe | —H | 7.5 | ≥250 | 33 |
| TJ177 | —(CH$_2$S)(CH$_2$)$_6$CH$_3$ | —COOMe | —H | 1.5 | 71 | 47 |

TABLE 7

Tumor cell selectivity of 5-arylthiomethyl-substituted 2-amino-3-carboxymethylthiophenes:

| Code | Y¹ | n | CEM IC$_{50}$ (µM) | HeLa IC$_{50}$ (µM) | Ratio |
|---|---|---|---|---|---|
| TJ179 | cyclopentyl | 1 | 1.8 | 80 | 44 |
| D8 | cyclohexyl | 1 | 2.1 | 81 | 39 |
| TJ4 | phenyl | 1 | 1.3 | 108 | 83 |
| TJ55 | 4-methylphenyl | 1 | 1.5 | 72 | 48 |
| D3 | 2-methylphenyl | 1 | 2 | 71 | 36 |
| TJ54P | 3-methylphenyl | 1 | 4.1 | 108 | 26 |
| TJ122 | 2-aminophenyl | 1 | 39 | 46 | 1 |
| TJ22 | 4-methoxyphenyl | 1 | 0.62 | 58 | 93 |
| D6 | 2-methoxyphenyl | 1 | 17 | 94 | 6 |
| D7 | 2-methoxycarbonylphenyl | 1 | 27 | 190 | 7 |
| TJ53 | 3-carboxyphenyl | 1 | 124 | 75 | ≤1 |
| D10 | 4-fluorophenyl | 1 | 3.1 | 102 | 33 |
| D4 | 4-chlorophenyl | 1 | 1.7 | 42 | 25 |
| TJ126 | 4-nitrophenyl | 1 | 12 | 16 | 1 |
| TJ55 | 4-methylphenyl | 1 | 1.5 | 72 | 48 |
| TJ185 | 4-ethylphenyl | 1 | 0.34 | 49 | 144 |
| TJ186 | 4-isopropylphenyl | 1 | 0.46 | 46 | 100 |
| TJ130 | 4-methoxybenzyl | 1 | 3.9 | 88 | 23 |
| TJ57 | benzyl | 1 | 3.5 | 61 | 17 |
| TJ187 | phenethyl | 1 | 1.2 | 74 | 62 |
| TJ184 | 4-biphenylyl | 1 | 1.2 | 55 | 46 |
| TJ113 | 2-naphthyl | 1 | 0.9 | 74 | 82 |

TABLE 7-continued

Tumor cell selectivity of 5-arylthiomethyl-substituted 2-amino-3-carboxymethylthiophenes:

![structure]

| Code | Y¹ | n | CEM | HeLa | Ratio |
|---|---|---|---|---|---|
| TJ129 | 4-pyridyl-CH₂ | 1 | 111 | 93 | 1 |
| TJ118 | 2-thienyl-CH₂ | 1 | 3.3 | 99 | 30 |
| TJ117 | 2-furyl-CH₂ | 1 | 4.9 | 102 | 21 |
| TJ170 | cyclohexyl-CH₂ | 3 | 0.57 | 55 | 96 |
| TJ169 | 4-methoxyphenyl | 3 | 0.97 | 59 | 61 |

REFERENCES

1. Romagnoli R, Baraldi P G, Pavani M G, Cruz-Lopez O, Hamel E, Balzarini J, Brognara E, Zuccato C, Gambari R. 2010. Synthesis and cellular pharmacology studies of a series of 2-amino-3-aroyl-4-substituted thiophene derivatives. Med. Chem. 6: 329-343.
2. Huang Y, Dömling A. 2011. The Gewald multicomponent reaction. Mol. Divers. 15: 3-33.

The invention claimed is:

1. A compound having the general formula I:

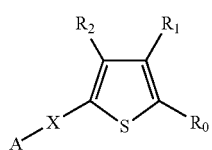

wherein

A is selected from the group consisting of $C_{1-7}$ alkyl; $C_{2-7}$ alkenyl; $C_{2-7}$ alkynyl; halo $C_{1-7}$ alkyl; $C_{3-10}$ cycloalkyl; $C_{1-7}$ alkoxy; $C_{3-10}$ cycloalkoxy; aryloxy; arylalkyloxy; oxyheterocyclic; thio $C_{1-7}$ alkyl; thio $C_{3-10}$ cycloalkyl; arylthio; arylalkylthio; heterocyclic-substituted alkyl; heterocyclic-substituted alkyloxy; heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, and wherein said alkyl is optionally substituted with one or more substituents selected from the group consisting of halogen, nitro, hydroxyl, sulfhydryl, amino, azido;

$R^0$ is independently selected from the group consisting of amino; (mono- or di) $C_{1-7}$ alkylamino; (mono- or di) arylamino; azido; 1H-Isoindole-1,3(2H)-dione,2-yl-;

$R^1$ is independently selected from the group consisting of carboxy$C_{1-7}$ alkyl; cyano; —COOH; —CONR$^a$R$^b$; —SO$_2$R; —SO$_2$NHR; —SO$_2$NR$^a$R$^b$, —SO$_2$OR; —PO(XR)$_2$; and $C_{3-10}$ cycloalkyl, wherein R, R$^a$ and R$^b$ are each independently selected from the group consisting of H and $C_{1-7}$alkyl and $C_{3-10}$ cycloalkyl;

$R^2$ is independently selected from the group consisting of hydrogen; carboxy$C_{1-7}$ alkyl, $C_{1-7}$alkyl; cyano; —CONHMe; —COOH; —CONH$_2$ X is independently selected from the group consisting of —(CH$_2$)$_n$—, —(CH$_2$)$_m$-acetylene, -acetylene-(CH$_2$)$_m$—, —(CH$_2$)$_m$-ethylene, -ethylene-(CH$_2$)$_m$—, —S(CH$_2$)$_m$—, —(CH$_2$)$_m$S—, —O(CH$_2$)$_m$—, —(CH$_2$)$_m$O—, —NH(CH$_2$)$_m$—; —(CH$_2$)$_m$NH—, —(CH$_2$)$_m$S(CH$_2$)$_p$—, —(CH$_2$)$_m$O(CH$_2$)$_p$—, wherein m is 0, 1, 2, 3, 4, 5, 6 or 7, and wherein p is 0, 1, 2, 3, 4, 5, 6 or 7, and wherein n is 2, 3, 4, 5, 6 or 7;

and/or a pharmaceutical acceptable addition salt thereof and/or a stereoisomer thereof and/or a solvate thereof;

with the proviso that said compound is not Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitile; 2-Amino-5-benzythiophene-3-carbonitrile; 2-Amino-5-isopropylthiophene-3-carbonitrile; 2-Amino-5-(tert-butyl)thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl)thiophene-3-carboxamide; 2-Amino-3-cyano-5-[2-(2',5'-dimethoxyphenyl)ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile.

2. The compound according to claim 1, wherein A is $C_{1-7}$ alkyl or $C_{2-7}$ alkenyl.

3. The compound according to claim 1, wherein A is phenyl or thiophene.

4. The compound according to claim 1, wherein $R^1$ is carboxy$C_{1-7}$alkyl.

5. The compound according to claim 1, wherein A is an aryl group substituted with 1 or 2 substituents selected from the group consisting of a methoxy group and a methyl group.

6. The compound according to claim 1, wherein X is selected from the group consisting of a —(CH$_2$)$_2$, an ethylene and an acetylene group.

7. The compound according to claim 1, wherein n is 2.

8. The compound according to claim 1, wherein R$^0$ is amino.

9. The compound according to claim 1, wherein R$^2$ is hydrogen.

10. The compound according to claim 1, wherein the compound is selected from the group consisting of: Methyl-2-amino-5-(2-(4-methoxyphenyl)ethyl)thiophene-3-carboxylate; Methyl-2-amino-5-(2-(phenylethyl)thiophene-3-carboxylate; Methyl-2-amino-5-(2-(2-methoxyphenyl)ethyl)thiophene-3-carboxylate; Methyl-2-amino-5-(2-(4-methoxy-2-methylphenyl)ethyl)thiophene-3-carboxylate; Methyl-2-amino-5-(2-(2-thienyl)ethyl)thiophene-3-carboxylate; Ethyl-2-amino-5-(2-(4-methoxyphenyl)ethynyl)thiophene-3-carboxylate; Ethyl-2-amino-5-(2-(4-methoxyphenyl)ethyl)thiophene-3-carboxylate; Ethyl-2-amino-5-(4-methoxyphenyl)thiophene-3-carboxylate; Ethyl-2-amino-5-(2-methoxyphenyl)thiophene-3-carboxylate; Ethyl-2-amino-5-(2-(2-methoxyphenyl)ethyl)thiophene-3-carboxylate; Ethyl-2-amino-4-ethoxycarbonyl 5-(2-(4-methoxyphenyl)ethyl)thiophene-3-carboxylate; Methyl-2-amino-5-(4-methoxyphenyl)thiophene-3-carboxylate; Methyl-2-amino-5-((2-methoxyphenyl)thiophene-3-carboxylate; 2-Amino-3-cyano-5-(4-methoxyphenyl)thiophene; Methyl-2-amino-5-(2,5-dimethoxyphenyl)thiophene-3-carboxylate; 2-Amino-3-cyano-5-(2-(2-methoxyphenyl)ethyl)thiophene; 2-Amino-3-cyano-5-(2-(4-methoxyphenyl)ethyl)thiophene; Ethyl-2-amino-5-(2-(2,5-dimethoxyphenyl)ethyl)thiophene-3-carboxylate; 2-Amino-3-cyano-5-(2-(phenyl)ethyl)thiophene; 2-Amino-3-cyano-5-(2-(2,5-dimethoxyphenyl)ethyl)thiophene; Ethyl-2-amino-4-ethoxycarbonyl-5-(2-(2,5-dimethoxymethoxyphenyl)ethyl)thiophene-3-carboxylate; Methyl-2-amino-5-(2-(2-pyridyl)ethyl)thiophene-3-carboxylate; Methyl-2-amino-5-(2-(3-pyridyl)ethyl)thiophene-3-carboxylate; Methyl-2-amino-4-methyl-5-(2-(2,5-dimethoxyphenyl)ethyl)thiophene-3-carboxylate; Methyl-2-amino-5-(2,5-dimethoxyphenyl)thiophene-3-carboxylate; N-Methyl-2-amino-5-(2-(4-methoxyphenyl)ethyl)thiophene-3-carboxamide; 2-Amino-5-(2-(4-methoxyphenyl)ethyl)thiophene-3-carboxylate; 2-Amino-5-(2-(4-methoxyphenyl)ethyl)thiophene-3-carboxamide; Methyl-2-methylamino-5-(2-(4-methoxyphenyl)ethyl)thiophene-3-carboxylate; Methyl-2-dimethylamino-5-(2-(4-methoxyphenyl)ethyl)thiophene-3-carboxylate; Methyl-5-(2-(4-methoxyphenyl)ethyl)thiophene-3-carboxylate; Methyl-2-amino-5-(2-(4-methoxyphenyl)sulfanylmethyl)thiophene-3-carboxylate; Methyl-2-amino-5-(2-(4-methoxyphenyl)oxymethyl)thiophene-3-carboxylate; Methyl-2-amino-5-(2-(4-methoxyphenyl)aminomethyl)thiophene-3-carboxylate; Methyl-2-amino-5-(2-(4-methylphenyl)sulfanylmethyl)thiophene-3-carboxylate; Methyl-2-amino-5-(2-(3-methylphenyl)sulfanylmethyl)thiophene-3-carboxylate; Methyl-2-amino-5-(2-(phenyl)methylsulfanylmethyl)thiophene-3-carboxylate; Methyl-2-amino-5-(2-(phenyl)sulfanylmethyl)thiophene-3-carboxylate; Methyl-2-phthalimido-5-(2-(4-methoxyphenyl)sulfanylmethyl)thiophene-3-carboxylate; and Methyl-2-phthalimido-5-(2-(3-methylphenyl)sulfanylmethyl)thiophene-3-carboxylate.

11. The compound according to claim 1, wherein the compound is selected from the group consisting of: Methyl-2-amino-5-(2-(4-methoxyphenyl)ethyl)thiophene-3-carboxylate; Methyl-2-amino-5-(2-(phenylethyl)thiophene-3-carboxylate; Methyl-2-amino-5-(2-(2-methoxyphenyl)ethyl)thiophene-3-carboxylate; Methyl-2-amino-5-(2-(4-methoxy-2-methylphenyl)ethyl)thiophene-3-carboxylate; Methyl-2-amino-5-(2-(2-thienyl)ethyl)thiophene-3-carboxylate; Ethyl-2-amino-5-(2-(4-methoxyphenyl)ethynyl)thiophene-3-carboxylate; and Ethyl-2-amino-5-(2-(4-methoxyphenyl)ethyl)thiophene-3-carboxylate.

12. A pharmaceutical composition comprising a therapeutically effective amount of a compound according to claim 1 or a compound selected from Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitile; 2-Amino-5-benzythiophene-3-carbonitrile; 2-Amino-5-isopropylthiophene-3-carbonitrile; 2-Amino-5-(tert-butyl)thiophene-3-carbonitrile; 2-Amino-5-heptylthiophene-3-carbonitrile; 2-Amino-5-butylthiophene-3-carbonitrile; 2-Amino-N-cyclopropyl-5-(methylsulfanylmethyl)thiophene-3-carboxamide; 2-Amino-3-cyano-5-[2-(2',5'-dimethoxyphenyl)ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile; and one or more pharmaceutically acceptable excipients.

13. The pharmaceutical composition according to claim 12, further comprising one or more biologically active drugs being selected from the group consisting of antineoplastic drugs and/or immunosuppressant and/or immunomodulator drugs.

14. A method of prevention or treatment of cancer in a subject, comprising the administration of a therapeutically effective amount of a compound according to claim 1, or a compound selected from Ethyl 2-amino-5-(3-benzyloxypropyl)-thiophene-3-carboxylate; Ethyl 2-amino-5-(4-benzyloxybutyl)-thiophene-3-carboxylate; Ethyl 2-amino-5-n-hexyl-thiophene-3-carboxylate; Ethyl 2-amino-5-n-pentyl-thiophene-3-carboxylate; Ethyl 2-amino-5-n-heptyl-thiophene-3-carboxylate; Ethyl 2-amino-5-methyl-4-(n-pentyl)-thiophene-3-carboxylate; Ethyl 2-amino-5-n-hexyl-4-methyl-thiophene-3-carboxylate; Ethyl 2-amino-5(7-acetoxy;n-heptyl)-thiophene-3-carboxylate; Ethyl 2-amino-5-(2-phenylethyl)-thiophene-3-carboxylate; Ethyl 2-amino-5-benzyl-4-methyl-thiophene-3-carboxylate; Ethyl 2-amino-5-n-decyl-thiophene-3-carboxylate; Ethyl 2-amino-5-n-nonyl-thiophene-3-carboxylate; Ethyl 2-amino-5-n-propyl-thiophene-3-carboxylate; 2-Amino-5-phenylthiophene-3-carbonitile; 2-Amino-5-benzythiophene-3-carbonitrile; 2-Amino-5-isopropylthiophene-3-carbonitrile; 2-Amino-5-(tert-butyl)thiophene-3-carbonitrile;

2-Amino-5-heptylthiophene-3-carbonitrile; 2-Amino-5-butylthiophene-3-carbonitrile; 2-Amino-N-cyclopropyl-5-(methylsulfanylmethyl)thiophene-3-carboxamide; 2-Amino-3-cyano-5-[2-(2',5'-dimethoxyphenyl)ethyl]-4-methylthiophene; 2-Amino-3-cyano-5-[2-(3',4',5'-trimethoxyphenyl)ethyl]-4-methylthiophene; 2-Amino-4-methyl-5-phenethyl-thiophene-3-carbonitrile; 2-amino-5-[2-(3,4-dichlorophenyl)ethyl]-4-methyl-thiophene-3-carbonitrile; optionally in combination with one or more pharmaceutically acceptable excipients.

15. A process for preparing a compound of formula I, comprising the steps of:
    (a) reaction of an enolizable compound (aldehyde or ketone), sulfur and an active methylene containing a cyano group under Gewald conditions;
    (b) protection of the 5-amino group as phthalimide via reaction with phthalic anhydride in acidic conditions, and further transformations at the 2-position of the thiophene via first bromination to afford the 2-bromo or 2-bromomethyl derivatives; and then nucleophilic substitution with the aromatic, heterocyclic or lipophilic side chain; or standard Sonogashira cross-coupling reaction with the aromatic, heterocyclic or lipophilic side chain; and
    (c) deprotection of the phthalimide function by hydrazine or methylhydrazine to liberate the 5-aminothiophene.

16. A compound selected from the group consisting of:
methyl 2-amino-5-propyl-thiophene-3-carboxylate; methyl 2-amino-5-(3-chloropropyl)thiophene-3-carboxylate; methyl 2-amino-5-butyl-thiophene-3-carboxylate; methyl 2-amino-5-pentyl-thiophene-3-carboxylate; methyl 2-amino-5-hexyl-thiophene-3-carboxylate; methyl 2-amino-5-heptyl-thiophene-3-carboxylate; methyl 2-amino-5-octyl-thiophene-3-carboxylate; methyl 2-amino-5-(1,5-dimethylhex-4-enyl)thiophene-3-carboxylate; 2-amino-5-non-8-enyl-thiophene-3-carbonitrile; methyl 2-amino-4-methyl-5-octyl-thiophene-3-carboxylate; methyl 2-amino-5-nonyl-thiophene-3-carboxylate; methyl 2-amino-5-decyl-thiophene-3-carboxylate; methyl 2-amino-5-dodecyl-thiophene-3-carboxylate; methyl 2-amino-5-tridecyl-thiophene-3-carboxylate; methyl 2-amino-5-tetradecyl-thiophene-3-carboxylate; methyl 2-amino-5-pentadecyl-thiophene-3-carboxylate; methyl 2-amino-5-hexadecyl-thiophene-3-carboxylate; methyl 2-amino-5-(butylthiomethyl)thiophene-3-carboxylate; methyl 2-amino-5-(pentylthiomethyl)thiophene-3-carboxylate; methyl 2-amino-5-(isopentylthiomethyl)thiophene-3-carboxylate; methyl 2-amino-5-(hexylthiomethyl)thiophene-3-carboxylate; methyl 2-amino-5-(heptylthiomethyl)thiophene-3-carboxylate; methyl 2-amino-5-(octylthiomethyl)thiophene-3-carboxylate; methyl 2-amino-5-(cyclopentylthiomethyl)thiophene-3-carboxylate; methyl 2-amino-5-(cyclohexylthiomethyl)thiophene-3-carboxylate; methyl 2-amino-5-(phenylthiomethyl)thiophene-3-carboxylate; methyl 2-amino-5-(p-tolylthiomethyl)thiophene-3-carboxylate; methyl 2-amino-5-(o-tolylthiomethyl)thiophene-3-carboxylate; methyl 2-amino-5-(m-tolylthiomethyl)thiophene-3-carboxylate; methyl 2-amino-5-[(2-aminophenyl)thiomethyl]thiophene-3-carboxylate; methyl 2-amino-5-[(4-methoxyphenyl)thiomethyl]thiophene-3-carboxylate; methyl 2-amino-5-[(2-methoxyphenyl)thiomethyl]thiophene-3-carboxylate; methyl 2-amino-5-[(2-methoxycarbonylphenyl)thiomethyl]thiophene-3-carboxylate; 3-((5-amino-4-(methoxycarbonyl)thiophen-2-yl)methylthio)benzoic acid; methyl 2-amino-5-[(4-fluorophenyl)thiomethyl]thiophene-3-carboxylate; methyl 2-amino-5-[(4-chlorophenyl)thiomethyl]thiophene-3-carboxylate; methyl 2-amino-5-[(4-nitrophenyl)thiomethyl]thiophene-3-carboxylate; methyl 2-amino-5-[(4-ethylphenyl)thiomethyl]thiophene-3-carboxylate; methyl 2-amino-5-[(4-isopropylphenyl)thiomethyl]thiophene-3-carboxylate; methyl 2-amino-5-[(4-methoxyphenyl)methylthiomethyl]thiophene-3-carboxylate; methyl 2-amino-5-[(phenyl)methylthiomethyl]thiophene-3-carboxylate; methyl 2-amino-5-(phenethylthiomethyl)thiophene-3-carboxylate; methyl 2-amino-5-[(biphenyl-4-yl)thiomethyl]thiophene-3-carboxylate; methyl 2-amino-5-(2-naphthylthiomethyl)thiophene-3-carboxylate; methyl 2-amino-5-(4-pyridylthiomethyl)thiophene-3-carboxylate; methyl 2-amino-5-(2-thienylmethylthiomethyl)thiophene-3-carboxylate; methyl 2-amino-5-(2-furylmethylthiomethyl)thiophene-3-carboxylate; methyl 2-amino-5-(3-cyclohexylthiopropyl)thiophene-3-carboxylate; methyl 2-amino-5-[3-(4-methoxyphenyl)thiopropyl]thiophene-3-carboxylate.

17. A method of prevention or treatment of cancer in a subject, comprising the administration of a therapeutically effective amount of a compound according to claim 16, optionally in combination with one or more pharmaceutically acceptable excipients.

18. The compound according to claim 1, wherein the compound has general formula Ia:

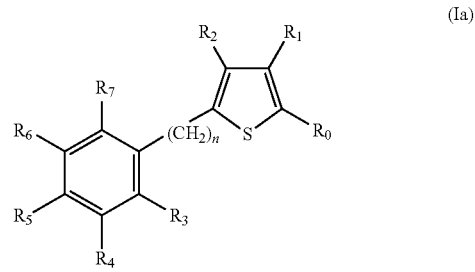

(Ia)

wherein $R^0$, $R^1$ $R^2$ and n are as defined in claim 1;
$R^3$, $R^4$, $R^5$, $R^6$ and $R^7$ are independently selected from the group consisting of hydrogen; $C_{1-7}$ alkyl; $C_{1-7}$ alkoxy; halogen; amino; and hydroxyl; and wherein said alkyl is optionally substituted with one or more substituents selected from the group consisting of halogen, nitro, hydroxyl, sulfhydryl, amino, and azido.

19. The compound according to claim 1, wherein the compound has general formula Ib:

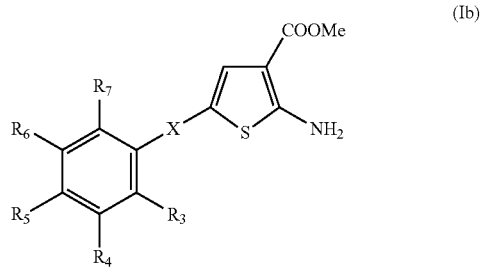

(Ib)

wherein X is as defined in claim 1; and
$R^3$, $R^4$, $R^5$, $R^6$ and $R^7$ are independently selected from the group consisting of hydrogen; $C_{1-7}$ alkyl; $C_{1-7}$ alkoxy; halogen; amino; and hydroxyl; and wherein said alkyl is optionally substituted with one or more substituents selected from the group consisting of halogen, nitro, hydroxyl, sulfhydryl, amino, and azido.

20. The compound according to claim 1, wherein $R^1$ is a carboxymethyl or carboxyethyl group.

21. The method according to claim 14, wherein said cancer is a lymphoma, liver cancer of prostate cancer.

22. The method according to claim 21, wherein said lymphoma is a T-cell lymphoma.

23. The method according to claim 14, wherein said subject is a human.

24. The compound according to claim 1, wherein A is $C_{1-7}$ alkyl substituted with hydroxyl, amino or sulfhydryl.

* * * * *